(12) United States Patent
Furness, III et al.

(10) Patent No.: US 8,081,304 B2
(45) Date of Patent: Dec. 20, 2011

(54) METHOD, APPARATUS, AND ARTICLE TO FACILITATE EVALUATION OF OBJECTS USING ELECTROMAGNETIC ENERGY

(75) Inventors: Thomas A. Furness, III, Seattle, WA (US); Brian T. Schowengerdt, Seattle, WA (US); Ross D. Melville, Issaquah, WA (US); Nicholas E. Walker, Springfield, OR (US); Bradley E. Sparks, Mercer Island, WA (US)

(73) Assignee: Visualant, Inc., Seattle, WA (US)

( * ) Notice: Subject to any disclaimer, the term of this patent is extended or adjusted under 35 U.S.C. 154(b) by 1093 days.

(21) Appl. No.: 11/831,717

(22) Filed: Jul. 31, 2007

(65) Prior Publication Data

US 2009/0112101 A1 Apr. 30, 2009

Related U.S. Application Data

(60) Provisional application No. 60/834,589, filed on Jul. 31, 2006, provisional application No. 60/871,639, filed on Dec. 22, 2006, provisional application No. 60/883,312, filed on Jan. 3, 2007, provisional application No. 60/890,446, filed on Feb. 16, 2007.

(51) Int. Cl.
*G06K 9/74* (2006.01)
(52) U.S. Cl. ......................................................... 356/71
(58) Field of Classification Search ...................... 356/71
See application file for complete search history.

(56) References Cited

U.S. PATENT DOCUMENTS

| | | | |
|---|---|---|---|
| 3,499,158 A | 3/1970 | Lavine et al. | 250/217 |
| 3,582,659 A | 6/1971 | Dekker | 250/214 R |
| 3,679,449 A | 7/1972 | Nagot et al. | 117/1 |
| 3,822,098 A | 7/1974 | Rudder et al. | 356/209 |
| 3,867,039 A | 2/1975 | Nelson | 356/178 |
| 3,922,090 A | 11/1975 | Fain | 356/71 |
| 3,942,185 A | 3/1976 | Lebailly | 357/17 |
| 3,994,590 A | 11/1976 | Di Martini et al. | 356/178 |
| 4,082,188 A | 4/1978 | Grimmell et al. | 209/73 |
| 4,098,940 A | 7/1978 | Groh et al. | 428/218 |
| 4,120,445 A | 10/1978 | Carrier et al. | 229/53 |
| 4,183,989 A | 1/1980 | Tooth | 428/195 |
| 4,241,738 A | 12/1980 | Lübbers et al. | 128/666 |

(Continued)

FOREIGN PATENT DOCUMENTS

WO 91/05459 5/1991

(Continued)

OTHER PUBLICATIONS

CRi Nuance Multispectral Imaging System, URL=http://www.cri-inc.com/products/nuance.asp, download date Jan. 30, 2007, 2 pages.

(Continued)

*Primary Examiner* — Michael P Stafira
(74) *Attorney, Agent, or Firm* — Seed IP Law Group PLLC

(57) ABSTRACT

Spectral information may be employed in process control and/or quality control of goods and articles. Spectral information may be employed in process control and/or quality control of media, for example financial instruments, identity documents, legal documents, medical documents, financial transaction cards, and/or other media, fluids for example lubricants, fuels, coolants, or other materials that flow, and in machinery, for example vehicles, motors, generators, compressors, presses, drills and/or supply systems. Spectral information may be employed in identifying biological tissue and/or facilitating diagnosis based on biological tissue.

22 Claims, 39 Drawing Sheets

U.S. PATENT DOCUMENTS

| | | | |
|---|---|---|---|
| 4,277,514 A | 7/1981 | Sugiura et al. | 427/1 |
| 4,325,981 A | 4/1982 | Sugiura et al. | 427/7 |
| 4,652,913 A | 3/1987 | Saitoh et al. | 358/75 |
| 4,678,338 A | 7/1987 | Kitta et al. | 356/402 |
| 4,830,501 A | 5/1989 | Terashita | 356/402 |
| 4,921,278 A | 5/1990 | Shiang et al. | 283/87 |
| 4,952,061 A | 8/1990 | Edgar | 356/407 |
| 5,137,364 A | 8/1992 | McCarthy | 356/402 |
| 5,325,167 A | 6/1994 | Melen | 356/71 |
| 5,377,000 A | 12/1994 | Berends | 356/73 |
| 5,619,326 A | 4/1997 | Takamatsu et al. | |
| 5,844,680 A | 12/1998 | Sperling | 356/303 |
| 5,933,244 A | 8/1999 | Kiritchenko | 356/402 |
| 5,966,217 A | 10/1999 | Roe et al. | 356/402 |
| 6,020,583 A | 2/2000 | Walowit et al. | 250/226 |
| 6,035,246 A | 3/2000 | Wagner | 700/266 |
| 6,038,024 A | 3/2000 | Berner | 356/324 |
| 6,054,021 A | 4/2000 | Kurrle et al. | 162/140 |
| 6,165,609 A | 12/2000 | Curatolo | 428/343 |
| 6,172,745 B1 * | 1/2001 | Voser et al. | 356/71 |
| 6,176,522 B1 | 1/2001 | Jackson | 283/91 |
| 6,255,948 B1 | 7/2001 | Wolpert et al. | 340/572.8 |
| 6,384,918 B1 | 5/2002 | Hubble, III et al. | 356/402 |
| 6,421,553 B1 | 7/2002 | Costa et al. | 600/476 |
| 6,449,045 B1 | 9/2002 | Mestha | 356/402 |
| 6,556,932 B1 | 4/2003 | Mestha et al. | 702/76 |
| 6,560,546 B1 | 5/2003 | Shenk et al. | 702/30 |
| 6,584,435 B2 | 6/2003 | Mestha et al. | 702/196 |
| 6,621,576 B2 | 9/2003 | Tandon et al. | 356/320 |
| 6,633,382 B2 | 10/2003 | Hubble, III et al. | 356/402 |
| 6,639,699 B2 | 10/2003 | Matsuyama | 359/35 |
| 6,690,465 B2 | 2/2004 | Shimizu et al. | 356/326 |
| 6,718,046 B2 | 4/2004 | Reed et al. | 382/100 |
| 6,721,440 B2 | 4/2004 | Reed et al. | 382/100 |
| 6,721,629 B2 | 4/2004 | Wendling et al. | 700/279 |
| 6,724,912 B1 | 4/2004 | Carr et al. | 382/100 |
| 6,731,785 B1 | 5/2004 | Mennie et al. | 382/135 |
| 6,744,909 B1 | 6/2004 | Kostrzewski et al. | 382/115 |
| 6,748,533 B1 | 6/2004 | Wu et al. | 713/176 |
| 6,757,406 B2 | 6/2004 | Rhoads | 382/100 |
| 6,763,124 B2 | 7/2004 | Alattar et al. | 382/100 |
| 6,782,115 B2 | 8/2004 | Decker et al. | 382/100 |
| 6,788,800 B1 | 9/2004 | Carr et al. | 382/100 |
| 6,798,517 B2 | 9/2004 | Wagner et al. | 356/406 |
| 6,804,377 B2 | 10/2004 | Reed et al. | 382/100 |
| 6,888,633 B2 | 5/2005 | Vander Jagt et al. | 356/407 |
| 6,930,773 B2 | 8/2005 | Cronin et al. | 356/300 |
| 6,937,323 B2 | 8/2005 | Worthington et al. | 356/73 |
| 6,968,337 B2 | 11/2005 | Wold | 707/100 |
| 6,992,775 B2 | 1/2006 | Soliz et al. | 356/456 |
| 6,993,535 B2 | 1/2006 | Bolle et al. | 707/104 |
| 6,995,839 B1 | 2/2006 | Shapiro | 356/301 |
| 6,996,478 B2 | 2/2006 | Sunshine et al. | 702/22 |
| 7,001,038 B2 | 2/2006 | Bock et al. | 362/125 |
| 7,003,132 B2 | 2/2006 | Rhoads | 382/100 |
| 7,003,141 B1 | 2/2006 | Lichtermann et al. | 382/124 |
| 7,005,661 B2 | 2/2006 | Yamaguchi et al. | 250/559.16 |
| 7,006,204 B2 | 2/2006 | Coombs et al. | 356/71 |
| 7,008,795 B2 | 3/2006 | Yerazunis et al. | 436/164 |
| 7,012,695 B2 | 3/2006 | Maier et al. | 356/453 |
| 7,016,717 B2 | 3/2006 | Demos et al. | 600/473 |
| 7,018,204 B2 | 3/2006 | Jung et al. | 433/26 |
| 7,023,545 B2 | 4/2006 | Slater | 356/326 |
| 7,026,600 B2 | 4/2006 | Jamieson et al. | 250/221 |
| 7,027,134 B1 | 4/2006 | Garcia-Rubio et al. | 356/39 |
| 7,027,165 B2 | 4/2006 | De Haas et al. | 356/600 |
| 7,027,619 B2 | 4/2006 | Pavlidis et al. | 382/115 |
| 7,031,555 B2 | 4/2006 | Troyanker | 382/305 |
| 7,032,988 B2 | 4/2006 | Darby et al. | 347/14 |
| 7,035,873 B2 | 4/2006 | Weare | 707/104.1 |
| 7,038,766 B2 | 5/2006 | Kerns et al. | 356/71 |
| 7,041,362 B2 | 5/2006 | Barbera-Guillem | 428/206 |
| 7,044,386 B2 | 5/2006 | Berson | 235/491 |
| 7,046,346 B2 | 5/2006 | Premjeyanth et al. | 356/71 |
| 7,046,842 B2 | 5/2006 | Lin et al. | 382/165 |
| 7,049,597 B2 | 5/2006 | Bodkin | 250/353 |
| 7,052,730 B2 | 5/2006 | Patel et al. | 427/7 |
| 7,052,920 B2 | 5/2006 | Ushio et al. | 438/14 |
| 7,058,200 B2 | 6/2006 | Donescu et al. | 382/100 |
| 7,061,652 B2 | 6/2006 | Kurita et al. | 358/3.28 |
| 7,063,260 B2 | 6/2006 | Mossberg et al. | 235/454 |
| 7,170,606 B2 | 1/2007 | Yerazunis | 356/432 |
| 7,171,680 B2 | 1/2007 | Lange | |
| 7,259,853 B2 | 8/2007 | Hubble, III et al. | 356/402 |
| 7,307,752 B1 | 12/2007 | Mestha et al. | 358/1.9 |
| 7,383,261 B2 | 6/2008 | Mestha et al. | 707/7 |
| 2002/0009213 A1 | 1/2002 | Rowe et al. | |
| 2002/0012447 A1 | 1/2002 | Amidror et al. | 382/100 |
| 2002/0146146 A1 | 10/2002 | Miolla et al. | 382/100 |
| 2002/0176600 A1 | 11/2002 | Rhoads et al. | 382/100 |
| 2003/0031347 A1 | 2/2003 | Wang | |
| 2003/0063772 A1 | 4/2003 | Smith et al. | 382/100 |
| 2003/0095726 A1 | 5/2003 | Kia et al. | 382/313 |
| 2003/0142314 A1 | 7/2003 | Hubble, III et al. | 356/402 |
| 2003/0151611 A1 | 8/2003 | Turpin et al. | 345/589 |
| 2003/0152274 A1 | 8/2003 | McGrew | 382/210 |
| 2003/0156752 A1 | 8/2003 | Turpin et al. | 382/162 |
| 2003/0158617 A1 | 8/2003 | Turpin et al. | 700/97 |
| 2003/0158788 A1 | 8/2003 | Turpin et al. | 705/26 |
| 2003/0174882 A1 | 9/2003 | Turpin et al. | 382/162 |
| 2003/0210805 A1 | 11/2003 | Lofgren et al. | 382/100 |
| 2004/0005086 A1 | 1/2004 | Wolff et al. | 382/118 |
| 2004/0071311 A1 | 4/2004 | Choi et al. | 382/100 |
| 2004/0071366 A1 | 4/2004 | Zhang et al. | 382/284 |
| 2004/0091131 A1 | 5/2004 | Honsinger et al. | 382/100 |
| 2004/0091153 A1 | 5/2004 | Nakano et al. | 382/228 |
| 2004/0101158 A1 | 5/2004 | Butler | 382/100 |
| 2004/0101159 A1 | 5/2004 | Butler | 382/100 |
| 2004/0101168 A1 | 5/2004 | Kostrzewski et al. | 382/115 |
| 2004/0105569 A1 | 6/2004 | Sharma et al. | 382/100 |
| 2006/0059013 A1 | 3/2006 | Lowe | 705/2 |
| 2006/0161788 A1 | 7/2006 | Turpin et al. | |
| 2007/0078610 A1 | 4/2007 | Adams et al. | 702/28 |
| 2008/0133389 A1 | 6/2008 | Schowengerdt et al. | |

FOREIGN PATENT DOCUMENTS

| | | |
|---|---|---|
| WO | 03/069884 | 8/2003 |
| WO | 2006050367 A2 | 5/2006 |
| WO | 2008016590 A2 | 2/2008 |

OTHER PUBLICATIONS

CRi Products Components, URL=http://www.cri-inc.com/products/components.asp, download date Jan. 30, 2007, 5 pages.

Furness III et al., "Method, Apparatus, and Article to Facilitate Evaluation of Objects Using Electromagnetic Energy," U.S. Appl. No. 60/834,589, filed Jul. 31, 2006, 135 pages.

Furness III et al., "Method, Apparatus, and Article to Facilitate Evaluation of Objects Using Electromagnetic Energy," U.S. Appl. No. 60/871,639, filed Dec. 22, 2006, 140 pages.

Furness III et al., "Method, Apparatus, and Article to Facilitate Evaluation of Objects Using Electromagnetic Energy," U.S. Appl. No. 60/883,312, filed Jan. 3, 2007, 147 pages.

Furness III et al., "Method, Apparatus, and Article to Facilitate Evaluation of Objects Using Electromagnetic Energy," U.S. Appl. No. 60/890,446, filed Feb. 16, 2007, 155 pages.

International Search Report, mailed Jun. 21, 2007, for PCT/US2005/039495, 1 page.

International Search Report, mailed Jul. 23, 2008, for PCT/US2007/017082, 1 page.

Schowengerdt et al., "System and Method of Evaluating an Object Using Electromagnetic Energy," U.S. Appl. No. 60/820,938, filed Jul. 31, 2006, 69 pages.

Schowengerdt et al., "Method, Apparatus, and Article to Facilitate Distributed Evaluation of Objects Using Electromagnetic Energy," U.S. Appl. No. 60/834,662, filed Jul. 31, 2006, 96 pages.

Schowengerdt, B., "Brief Technical Description of the Cyclops Spectral Analysis and Authentication System," Visualant Inc. memorandum, not disclosed prior to Dec. 22, 2006, 2 pages.

Schowengerdt et al., "Method, Apparatus, and Article to Facilitate Distributed Evaluation of Objects Using Electromagnetic Energy," Office Action mailed Jan. 21, 2010 for U.S. Appl. No. 11/831,662, 21 pages.

Schowengerdt et al., "Method, Apparatus, and Article to Facilitate Distributed Evaluation of Objects Using Electromagnetic Energy," Amendment filed Apr. 26, 2010 for U.S. Appl. No. 11/831,662, 41 pages.

Schowengerdt et al., "System and Method of Evaluating an Object Using Electromagnetic Energy," U.S. Appl. No. 12/375,814, filed Jan. 30, 2009, 69 pages.

Schowengerdt et al., "System and Method of Evaluating an Object Using Electromagnetic Energy," Preliminary Amendment filed Jan. 30, 2009 for U.S. Appl. No. 12/375,814, 14 pages.

Thomas, R., "A Beginners Guide to ICP-MS—Part V: The Ion Focusing System," Spectrospcopy 16(9):38-44, Sep. 2001. (Blank pages appear to be intentional).

Turpin, K., "Full Color Spectrum Object Authentication Methods and Systems," U.S. Appl. No. 60/623,881, filed Nov. 1, 2004, 114 pages.

Turpin et al., "Full Color Spectrum Object Authentication Methods and Systems," U.S. Appl. No. 60/732,163, filed Oct. 31, 2005, 198 pages.

Turpin et al., "Full Color Spectrum Object Authentication Methods and Systems," U.S. Appl. No. 11/264,626, filed Nov. 1, 2005, 46 pages.

Turpin et al., "Full Color Spectrum Object Authentication Methods and Systems," Preliminary Amendment filed Jul. 27, 2006 for U.S. Appl. No. 11/264,626, 3 pages.

Turpin et al., "Full Color Spectrum Object Authentication Methods and Systems," Office Action mailed May 4, 2007 for U.S. Appl. No. 11/264,626, 9 pages.

"Color Technology Beyond the Visible Spectrum Creating Solutions for Product Authentication: Extraordinary Investment Opportunity & 12 Month Roadmap," Visualant Inc., Seattle, Washington, Nov. 17, 2006, 10 pages.

Written Opinion, mailed Jun. 21, 2007, for PCT/US2005/039495, 5 pages.

Written Opinion, mailed Jul. 23, 2008, for PCT/US2007/017082, 3 pages.

Schowengerdt et al., "Method, Apparatus, and Article to Facilitate Distributed Evaluation of Objects Using Electromagnetic Energy," Office Action mailed Jul. 8, 2010 for U.S. Appl. No. 11/831,662, 11 pages.

Vrhel, "An LED based spectrophotometric instrument," *Color Imaging: Device-Independent Color, Color Hardcopy, and Graphic Arts IV, Proceedings of the SPIE* 3648:226-236, Jan. 1999.

\* cited by examiner

| OBJECT | TYPE | EMISSION SPECTRUM (nm) | CURRENT LEVEL (ma) | TEMP. (°C) | SENSOR SENSITIVITY | REFERENCE RESPONSE |
|---|---|---|---|---|---|---|
| 6778342 | HANDBAG | 224a | 1 228a | 32 | | |
| ⋮ | ⋮ | ⋮ | ⋮ | ⋮ | ⋮ | ⋮ |
| 6778342 | HANDBAG | | 1 | 40 | | |
| 6778342 | HANDBAG | 224b | 2 228b | 32 | | |
| ⋮ | ⋮ | ⋮ | ⋮ | ⋮ | ⋮ | ⋮ |
| 6778342 | HANDBAG | 224c | 3 228c | 40 | | |
| 6778342 | HANDBAG | 224d | 1 | 32 | | |
| ⋮ | ⋮ | ⋮ | ⋮ | ⋮ | ⋮ | ⋮ |
| 6778342 | HANDBAG | 224e | 3 | 40 | | |
| 1123407 | CURRENCY | | 1 | 32 | | |
| ⋮ | ⋮ | ⋮ | ⋮ | ⋮ | ⋮ | ⋮ |
| 1123407 | CURRENCY | | 3 | 40 | | |
| 0078406 | RETINAL TISSUE | | 1 | 37 | | |
| ⋮ | ⋮ | ⋮ | ⋮ | ⋮ | ⋮ | ⋮ |
| 0078406 | RETINAL TISSUE | | 4 | 40 | | |
| 2277603 | CURED RUBBER | | 1 | 180 | | |
| ⋮ | ⋮ | ⋮ | ⋮ | ⋮ | ⋮ | ⋮ |
| 2277603 | CURED RUBBER | | 4 | 180 | | |
| ⋮ | ⋮ | ⋮ | ⋮ | ⋮ | ⋮ | ⋮ |
| 8763244 | HOMOGENIZED MILK | | 2 | 4 | | |
| ⋮ | ⋮ | ⋮ | ⋮ | ⋮ | ⋮ | ⋮ |
| 8763244 | HOMOGENIZED MILK | | 2 | 35 | | |
| ⋮ | ⋮ | ⋮ | ⋮ | ⋮ | ⋮ | ⋮ |
| 8763244 | HOMOGENIZED MILK | | 2 | 35 | | |
| ⋮ | ⋮ | ⋮ | ⋮ | ⋮ | ⋮ | ⋮ |

┌─572
| SEQUENTIALLY ILLUMINATE AT LEAST A PORTION OF THE OBJECT BEING MANUFACTURED WITH ELECTROMAGNETIC ENERGY FROM BANDS WITHIN A VISIBLE PORTION, AN INFRARED PORTION OR AN ULTRAVIOLET PORTION OF THE ELECTROMAGNETIC SPECTRUM |

┌─578
| SELECTIVELY TURN RESPECTIVE ONES OF A PLURALITY OF SOURCES ON AND OFF IN AN ORDER DEFINED BY THE SEQUENCE |

┌─582
| SELECTIVELY APPLY CURRENT TO RESPECTIVE ONES OF THE SOURCES IN THE ORDER DEFINED BY THE SEQUENCE |

┌─588
| SELECTIVELY APPLY CURRENT AT A PLURALITY OF DIFFERENT LEVELS TO RESPECTIVE ONES OF THE SOURCES (E.G., LEDS) WHERE THE ORDER AND THE LEVEL ARE DEFINED BY THE SEQUENCE |

*FIG. 16*

```
                                                           ┌─ 1000
                                                          /
                                                    ┌─ 1002
                                                   /
┌─────────────────────────────────────────────────────────┐
│ SEQUENTIALLY ILLUMINATE AT LEAST THE FIRST PORTION OF THE│
│ BIOLOGICAL TISSUE BEING EVALUATED WITH ELECTROMAGNETIC   │
│ ENERGY FROM BANDS WITHIN A VISIBLE PORTION, AN INFRARED  │
│ PORTION OR AN ULTRAVIOLET PORTION OF THE ELECTROMAGNETIC │
│ SPECTRUM                                                 │
└─────────────────────────────────────────────────────────┘
```

*FIG. 25*

```
                                          ┌─ 1006
                                         /
                                    ┌─ 1008
                                   /
┌──────────────────────────────────────────────────────┐
│ SELECTIVELY TURN RESPECTIVE ONES OF A PLURALITY OF   │
│ SOURCES ON AND OFF IN AN ORDER DEFINED BY THE SEQUENCE│
└──────────────────────────────────────────────────────┘
```

*FIG. 26*

```
                                          ┌─ 1012
                                         /
                                    ┌─ 1014
                                   /
┌──────────────────────────────────────────────────────┐
│ SELECTIVELY APPLY CURRENT TO RESPECTIVE ONES OF THE  │
│ SOURCES IN THE ORDER DEFINED BY THE SEQUENCE         │
└──────────────────────────────────────────────────────┘
```

*FIG. 27*

```
                                          ┌─ 1018
                                         /
                                    ┌─ 1020
                                   /
┌──────────────────────────────────────────────────────┐
│ SELECTIVELY APPLY CURRENT AT A PLURALITY OF DIFFERENT│
│ LEVELS TO RESPECTIVE ONES OF THE SOURCES (E.G., LEDS),│
│ WHERE THE ORDER AND THE LEVEL ARE DEFINED BY THE     │
│ SEQUENCE                                             │
└──────────────────────────────────────────────────────┘
```

*FIG. 28*

```
                                          ┌─ 1024
                                         /
                                    ┌─ 1026
                                   /
┌──────────────────────────────────────────────────────┐
│ CLASSIFY THE PORTION OF BIOLOGICAL TISSUE            │
└──────────────────────────────────────────────────────┘
```

SEQUENTIALLY ILLUMINATE AT LEAST THE FIRST PORTION OF THE MEDIUM BEING EVALUATED WITH ELECTROMAGNETIC ENERGY FROM BANDS WITHIN A VISIBLE PORTION, AN INFRARED PORTION OR AN ULTRAVIOLET PORTION OF THE ELECTROMAGNETIC SPECTRUM

SELECTIVELY TURN RESPECTIVE ONES OF A PLURALITY OF SOURCES ON AND OFF IN AN ORDER DEFINED BY THE SEQUENCE

SELECTIVELY APPLY CURRENT TO RESPECTIVE ONES OF THE SOURCES IN THE ORDER DEFINED BY THE SEQUENCE

SELECTIVELY APPLY CURRENT AT A PLURALITY OF DIFFERENT LEVELS TO RESPECTIVE ONES OF THE SOURCES (*E.G.*, LEDS) WHERE THE ORDER AND THE LEVEL ARE DEFINED BY THE SEQUENCE

CLASSIFY THE MEDIUM AS A MEDIA TYPE BASED AT LEAST IN PART ON THE COMPARISON

COMPARE THE MEASURED RESPONSES TO A SET OF REFERENCE RESPONSES TO ILLUMINATION OF A REFERENCE SPECIMEN OF A REFERENCE MEDIUM

COMPARE THE MEASURED RESPONSES TO A SET OF REFERENCE RESPONSES TO ILLUMINATION OF THE MEDIUM DURING A PREVIOUS PERIOD THAT OCCURRED BEFORE THE FIRST PERIOD

SEQUENTIALLY ILLUMINATE AT LEAST A FIRST PORTION OF A FINANCIAL INSTRUMENT (*E.G.*, A CHECK, A BOND, A MONEY ORDER OR A SECURITY)

*FIG. 47*

```
                                                              ┌─1498
                                                             /─1500
┌─────────────────────────────────────────────────────────────┐
│ SEQUENTIALLY ILLUMINATE AT LEAST A FIRST PORTION OF AN IDENTITY │
│ DOCUMENT (E.G., A PASSPORT, AN IDENTITY CARD, A DRIVER'S LICENSE, │
│                   OR A BIRTH CERTIFICATE)                   │
└─────────────────────────────────────────────────────────────┘
```

*FIG. 48*

```
                                                              /─1504
                                                             /─1506
┌─────────────────────────────────────────────────────────────┐
│  SEQUENTIALLY ILLUMINATE AT LEAST A FIRST PORTION BEARING A │
│  LIKENESS OF AN INDIVIDUAL IDENTIFIED BY AN IDENTITY DOCUMENT│
└─────────────────────────────────────────────────────────────┘
```

*FIG. 49*

```
                                                              /─1510
                                                             /─1512
┌─────────────────────────────────────────────────────────────┐
│   SEQUENTIALLY ILLUMINATE AT LEAST A FIRST PORTION OF A LEGAL│
│   DOCUMENT (E.G., A LICENSE, A PERMIT, AN ASSIGNMENT, A DEED, A│
│   WILL, A DECLARATION, AN OATH, AN AGREEMENT, A PLEADING, OR A│
│                           MOTION)                           │
└─────────────────────────────────────────────────────────────┘
```

*FIG. 50*

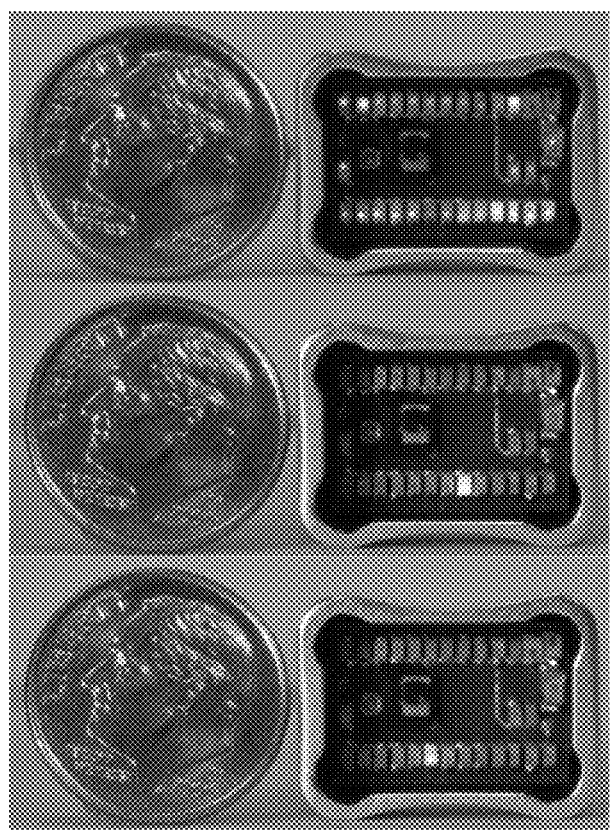
FIG. 52
FIG. 53
FIG. 54
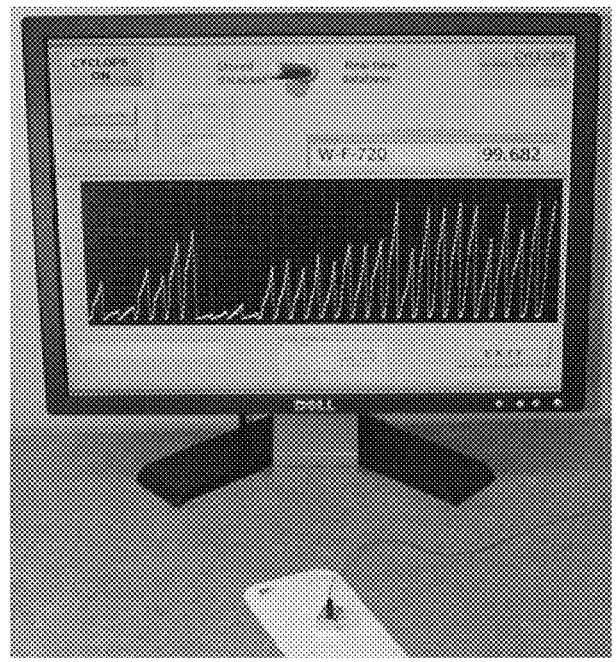
FIG. 55

US 8,081,304 B2

METHOD, APPARATUS, AND ARTICLE TO FACILITATE EVALUATION OF OBJECTS USING ELECTROMAGNETIC ENERGY

CROSS-REFERENCE TO RELATED APPLICATION

This application claims benefit under 35 U.S.C. §119(e) to U.S. Provisional Patent Application Nos. 60/890,446, filed Feb. 16, 2007; 60/883,312, filed Jan. 3, 2007; 60/871,639, filed Dec. 22, 2006; and 60/834,589, filed Jul. 31, 2006.

BACKGROUND

1. Field

This disclosure generally relates to evaluation systems, and more particularly to systems that evaluate characteristics of an object using electromagnetic energy.

2. Description of the Related Art

There are a number of proposed systems that employ spectral analysis of light received from a sample to recognize the sample.

US Patent Application Publication 2006-0161788 A1 describes full color spectrum object authentication methods and systems. In particular, a spectrum measuring device measures a region of respective sampled objects to produce spectral content information that identifies the sampled objects. The spectrum measuring device includes a plurality of individual sensors, which preferably includes specialized narrow band near-infrared and near-ultraviolet sensors, for example photodiodes or photomultipliers. Computers employ spectral analysis software to generate a unique measured pattern, which is then compared with reference patterns stored in a database. The spectral analysis software may be remotely located on a server accessible by the computers. The spectral analysis is preferably performed using XYZ color space modeling, although other color space models may be employed. The region being sampled may be varied to prevent third parties from easily anticipating the location. Samples may be take from multiple regions to insure accuracy.

U.S. Pat. No. 5,844,680 is directed to a device and process for measuring and analyzing spectral radiation, in particular for measuring and analyzing color characteristics. In particular, a number of radiation sources are provided in combination with a sensor for detecting radiation within a desired wavelength range. The radiation sources have spectral characteristics that are linearly independent from one another, but overlap so that in combination, the radiation sources generate radiation over the entire desired wavelength range. Alternatively, a single radiation source is provided that generates radiation over the entire desired wavelength range, in combination with a plurality of sensors that have spectral sensing characteristics that are linearly independent from one another, but overlap the entire desired wavelength range. A control unit stores a number of calibration functions with linearly independent spectral characteristics.

The patents and other publications directed to the field of object authentication and/or object identification are too numerous to describe. The above described publication and patent are only representative.

BRIEF SUMMARY

It may be useful to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object. In order to uniquely identify a large number of objects, it may be useful to collect a large number of distinct reference responses from one or more reference objects. This may be difficult to do with fixed illumination. This may also be difficult to do when sensing at a limited number of bands. It may also be useful to separate hardware and/or software functions into separate systems that may be remote to one another. Such may reduce costs and/or permit the use of hardware or software that could not otherwise be financially justified. It may also be useful to apply the object evaluation to specific applications, for example: manufacturing process control, quality assurance, media authentication, biological tissue recognition, identification, verification, authentication, classification, and/or diagnostics.

In one aspect, a method of method of facilitating manufacturing of objects can be summarized as during a first period, sequentially illuminating at least a first portion of an object being manufactured with a plurality of bands of electromagnetic energy in a first sequence; during the first period, measuring a plurality of responses to the illumination from at least the first portion of the object being manufactured; comparing the measured responses of the first period to a first set of reference responses to illumination of a reference specimen of an object; and determining whether at least a portion of the manufacturing process is complete based at least in part on the comparison of the measured responses of the first period to the first set of reference responses.

In another aspect, a method of facilitating quality control for manufactured objects can be summarized as during a first period, sequentially illuminating at least a first portion of an object being evaluated with a plurality of bands of electromagnetic energy; during the first period, measuring a plurality of responses to the illumination from at least the first portion of the object being evaluated; comparing the measured responses of the first period to a set of reference responses to illumination of a reference specimen of an object; and determining whether the object being evaluated is acceptable at least partially based on the comparison.

In yet another aspect, a method of evaluating biological tissue can be summarized as during a first period, sequentially illuminating at least a first portion of a biological tissue being evaluated with a plurality of bands of electromagnetic energy in a first sequence; during the first period, measuring a plurality of responses to the illumination from at least the first portion of the biological tissue being evaluated; comparing the measured responses of the first period to a first set of reference responses to illumination of a reference specimen of biological tissue; and identifying the portion of biological tissue based at least in part on the comparison of the measured responses of the first period to the first set of reference responses.

In still another aspect, a method of method of facilitating diagnosis using biological tissues can be summarized as during a first period, sequentially illuminating at least a first portion of a biological tissue with a plurality of bands of electromagnetic energy in a first sequence; during the first period, measuring a plurality of responses to the illumination from at least the first portion of the biological tissue; comparing the measured responses of the first period to a first set of reference responses to illumination of a reference specimen of biological tissue; and diagnosing at least the first portion of biological tissue based at least in part on the comparison of the measured responses of the first period to the first set of reference responses.

In yet still another aspect, a method of verification can be summarized as during a first period, sequentially illuminating at least a first portion of a medium being evaluated with a plurality of bands of electromagnetic energy in a first sequence; during the first period, measuring a plurality of responses to the illumination from at least the first portion of the medium being evaluated that is indicative of both a portion of content and a portion of material of the medium being evaluated; comparing the measured responses of the first period to a first set of reference responses; and determining whether the medium is authenticate based at least in part on the comparison of the measured responses of the medium being evaluated to the first set of reference responses.

In a further aspect, a system useful in manufacturing of objects can be summarized as means for sequentially illuminating at least a first portion of an object being manufactured with a plurality of bands of electromagnetic energy in a sequence that may be varied from time-to-time; means for measuring a plurality of responses to the illumination from at least the first portion of the object being manufactured during the illumination; and means for determining whether at least a portion of the manufacturing process is complete based at least in part on a comparison of the measured responses to a set of reference responses and based on the sequence of illumination.

In yet a further aspect, a system useful in evaluating manufactured objects can be summarized as means for sequentially illuminating at least a first portion of an object being evaluated with a plurality of bands of electromagnetic energy in a sequence that may be varied from time-to-time; means for measuring a plurality of responses to the illumination from at least the first portion of the object being evaluated; and means for determining whether the object being evaluated is acceptable at least partially based on a comparison of the measured responses to a set of reference responses and based on the sequence of illumination.

In still a further aspect, a system useful in evaluating biological tissue can be summarized as means for sequentially illuminating at least a first portion of a first portion of a biological tissue with a plurality of bands of electromagnetic energy in a sequence that may be varied from time-to-time; means for measuring a plurality of responses to the illumination from at least the first portion of the biological tissue being evaluated; and means for identifying the biological tissue based at least in part on a comparison of the measured responses to a set of reference responses and based on the sequence of illumination.

In yet still a further aspect, a system useful in evaluating biological tissue can be summarized as means for sequentially illuminating at least a first portion of a first portion of a biological tissue with a plurality of bands of electromagnetic energy in a sequence that may be varied from time-to-time; means for measuring a plurality of responses to the illumination from at least the first portion of the biological tissue being evaluated; and means for diagnosing at least the first portion of biological tissue based at least in part on a comparison of the measured responses to a set of reference responses and based on the sequence of illumination.

In even still a further aspect, a system useful in verification can be summarized as means for sequentially illuminating at least a first portion of a medium being evaluated with a plurality of bands of electromagnetic energy in a sequence that may be varied from time-to-time; means for measuring a plurality of responses to the illumination from at least the first portion of the medium being evaluated; and means for determining whether the medium is authenticate based at least in part on a comparison of the measured responses to a set of reference responses and based on the sequence of illumination.

In yet even still a further aspect, a method of inspecting manufactured objects for deterioration includes during a first period, sequentially illuminating at least a first portion of an object being manufactured with a plurality of bands of electromagnetic energy in a first sequence; during the first period, measuring a plurality of responses to the illumination from at least the first portion of the object being manufactured; comparing the measured responses of the first period to a first set of reference responses to illumination of a reference specimen of an object; and determining whether the manufactured object has deteriorated beyond an acceptable amount based at least in part on the comparison of the measured responses of the first period to the first set of reference responses. The reference responses may be indicative of a product or material that has not deteriorated beyond the acceptable amount or that has deteriorated beyond the acceptable amount. Deterioration may be related to fatigue, cracking, stress or strain, for example such as is associated with cyclic loading. Deterioration may be related to environmental factors, for example ultraviolet radiation, wind, temperature fluctuations, freezing, high temperatures, moisture, lightening strikes, etc. Deterioration beyond and acceptable amount may indicate that the product be removed from service or operation, or may indicate a need for repair or replacement. An entire surface may be inspected, or portions of a surface known or suspected of being susceptible to deterioration may be inspected. Inspection may be routine and periodic or may occur on an ad hoc basis.

In yet even further aspects, systems and methods allow the monitoring of the quality or health of goods, products or other materials, and/or with equipment that employ or supply such materials. For example, the quality or health of materials supplied to machinery may be monitored. Such may be done with, or without the removal of samples. Materials may include liquids or other materials that flow, such as gels or particles (e.g., grain, powder, slurry, etc.) Materials may for example, take the form of lubricants, fuels, and/or coolants. Monitoring the condition of materials may not only supply information about the material itself, but may also provide information about the condition of the machinery (e.g., temperature, alignment, wear) and/or system supplying the materials (e.g., condition of filter).

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 6 is a schematic diagram of a data structure of reference data stored in a computer-readable memory, according to one illustrated embodiment.

FIG. 13 is a flow diagram showing a method of operating a test device to sample an object during manufacture, according to one illustrated embodiment.

FIG. 14 is a flow diagram showing a method of operating a test device to sample an object during manufacture, according to another illustrated embodiment.

FIG. 15 is a flow diagram showing a method of operating a test device to sample an object during manufacture, according to still another illustrated embodiment.

FIG. 16 is a flow diagram showing a method of operating a test device to sample an object during manufacturer, according to a further illustrated embodiment.

FIG. 25 is a flow diagram showing a method of operating a test device to sample a biological tissue for identification, according one illustrated embodiment.

FIG. 26 is a flow diagram showing a method of operating a test device to sample a biological tissue for identification, according to another illustrated embodiment.

FIG. 27 is a flow diagram showing a method of operating a test device to sample biological tissue for identification, according to yet another illustrated embodiment.

FIG. 28 is a flow diagram showing a method of operating a test device to sample biological tissue for identification, according to still another illustrated embodiment.

FIG. 29 is a flow diagram showing a method of operating a test device to sample biological tissue for identification, according to a further illustrated embodiment.

FIG. 40 is a flow diagram showing a method of operating a test device to sample a medium, according to one illustrated embodiment.

FIG. 41 is a flow diagram showing a method of operating a test device to sample a medium, according to another illustrated embodiment.

FIG. 42 is a flow diagram showing a method of operating a test device to sample a medium, according to yet another illustrated embodiment.

FIG. 43 is a flow diagram showing a method of operating a test device to sample a medium, according to a further illustrated embodiment.

FIG. 44 is a flow diagram showing a method of operating a test device and/or computing system of an evaluation system to classify objects, useful with some of the previous methods, according to one illustrated embodiment.

FIG. 45 is a flow diagram showing a method of operating a test device and/or computing system of an evaluation system to authenticate a medium being evaluated being a copy of an original medium, which may be useful with at least some of the previous methods, according to one illustrated embodiment.

FIG. 46 is a flow diagram showing a method of operating a test device and/or computing system of an evaluation system to authenticate a medium being evaluated being an original medium, which may be useful with at least some of the previous methods, according to one illustrated embodiment.

FIG. 47 is a flow diagram showing a method of operating a test device to sample a portion of a financial instrument, according to one illustrated embodiment.

FIG. 48 is a flow diagram showing a method of operating a test device to sample a portion of an identity document, according to one illustrated embodiment.

FIG. 49 is a flow diagram showing a method of operating a test device to sample a portion of a document bearing a likeness of an individual, according to one illustrated embodiment.

FIG. 50 is a flow diagram showing a method of operating a test device to sample a portion of a legal document, according to one illustrated embodiment.

FIG. 52 shows a test device according to one illustrated embodiment, positioned next to a dime to illustrate a possible size of the test device, and with all sources simultaneously illuminated to better illustrate the various wavelengths of the sources.

FIG. 53 shows the test device of FIG. 52 with one source illuminated during operation.

FIG. 54 shows the test device of FIG. 52 with another source illuminated during operation.

FIG. 55 shows a monitor and displaying a screen of a user interface, according to an illustrated embodiment.

DETAILED DESCRIPTION

Figure 1:
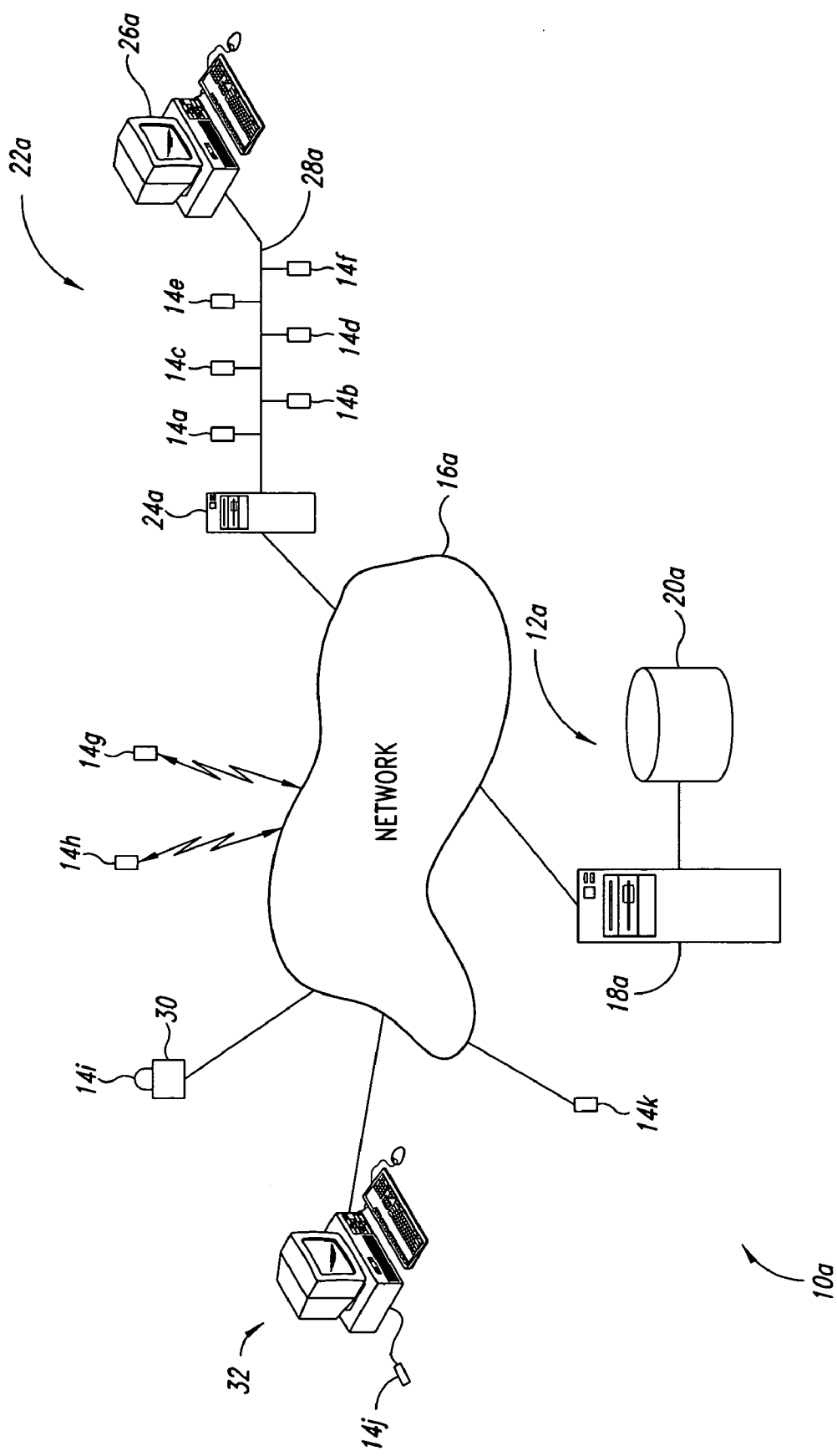
FIG. 1 is a schematic diagram of an object evaluation system including a host system and a plurality of remote test devices, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems, networks, servers, microprocessors, memories, buses, and sources of electromagnetic energy have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

The ability to recognize, identify, verify, authenticate and/or classify objects has numerous commercial applications.

It may be useful to determine whether an object being evaluated is identical to a previously evaluated object; in other words determine whether an object being sampled is the exact same object as a reference object. Alternatively, it may be useful to determine whether an object being evaluated is similar to a reference object; in other words determine whether an object being sampled is a facsimile of the reference object.

For example, it may be useful to determine whether a manufactured object is identical to a previously evaluated manufactured object. Such may be useful in authenticating goods, and deterring counterfeiting or gray marketing of goods. For example, it may also be useful to determine whether other objects, such as paintings or other works of art are identical to a previously sampled work of art. For example, it may be useful to determine whether an object being manufactured is similar to a previously evaluated object. Such may be useful in manufacturing process control and/or quality control.

For example, it may be useful to determine whether a medium is identical to a previously evaluated medium. For example, it may be useful to determine whether a medium is similar to a previously evaluated medium.

For example, it may be useful to determine whether a medium such as a document is identical to a previously evaluated document. For example, it may be useful to determine whether a medium such as a document is similar to a previously evaluated document. Such may be useful in recognizing, identifying, verifying, authenticating and/or classifying financial instruments such as currency, checks, bonds, money orders, and/or securities. Such may also be useful in recognizing, identifying, verifying, authenticating and/or classifying identification documents, such as passports, identity cards (e.g., national, state, provincial, military, employer, school, organization), driver's licenses, and/or birth or naturalization certificates. Such may also be useful in recognizing, identifying, verifying, authenticating and/or classifying legal documents such as licenses, permits, assignments, deeds, wills, declarations, oaths, agreements, pleadings, or motions. Such may be useful in recognizing, identifying, verifying, authenticating and/or classifying medical related documents, such as medical records, medical data, medical reports, and/or medical images (e.g., X-Ray, CAT scan, MRI, tomography, etc.).

For example, it may also be useful to determine whether a medium such as a financial transaction card is identical to a previously evaluated financial transaction cards. For example, it may be useful to determine whether medium such as a financial transaction card is similar to a previously evaluated financial transaction card. Such may be useful in deterring fraud and/or misuse of documents and other media. Such may be useful in recognizing, identifying, verifying, authenticating and/or classifying financial instruments such as credit cards, debit cards, and/or gift cards.

Also for example, it may be useful to determine whether a piece of biological tissue from a subject is identical to a previously evaluated piece of tissue. Also for example, it may be useful to determine whether a piece of biological tissue from a subject is similar to a previously evaluated piece of tissue. Such may also be useful in recognizing, identifying, verifying, authenticating, classifying, and/or diagnosing biological tissue, such as bodily tissue including retinal tissue, skin, blood, bone, hair, organs, etc. For example, such may be used to identify a subject from which the biological tissue was obtained. Also for example, such may be used to assess a condition of the biological tissue or subject from which the biological tissue was obtained. For example, the biological tissue being evaluated may be compared to normal and/or abnormal reference biological tissue specimens, which may be used for diagnosing a condition or characteristic.

It may be particularly useful where the above may occur based on the natural conditions or attributes of the object, media, or biological tissue, without the need to apply dedicated indicia such as serial numbers, machine-readable symbols (e.g., barcode symbols, area or matrix code symbols, stack code symbols), and/or radio frequency identification (RFID tags). Such dedicated data carriers may, in some embodiments, provide additional information regarding the object.

All of the above may, or may not, employ additional information about the object to facilitate the process. Additional information may include one or more measurable or observable physical characteristics of the object, media or biological tissue, for example, height, weight, age, hair or eye color, gender, location, type, size, denomination, serial numbers, security features, name, type, serial numbers, date of issue, color, etc. Such additional information may be employed to confirm a match, or to reduce the number of reference responses for comparison with a test response.

The ability to perform such in a network environment may provide a variety of distinct advantages. For example, such may make possible low cost end user test devices, which share or gain remote access to higher cost computing hardware and software. Such may allow the costs of the computing hardware and software to be shared over a variety of end users or financial entities. Such may also allow for "centralization" of relatively higher cost computing hardware and software, perhaps permitting use of high speed super-computers that could not otherwise be financially justified for individual end users or small groups of end users. Such also may allow for "decentralization" of low cost sampling or test devices. Such may also allow for light weight and/or low power consuming test devices. Such may additionally or alternatively permit the upgrade of previously distributed test devices. Such may also permit the distribution of work load. Such may also facilitate the backing up of data, and provide for redundancy. Other advantages will be apparent from the teachings herein.

FIG. 1 shows an object evaluation system 10a including one or more host systems 12a and a number of test devices 14a-14j (collectively 14) communicatively coupled to the host system 12a via one or more networks 16a. One or more of the test devices 14 may be remotely located with respect to the host system 12a.

The host system 12 may include one or more computing systems 18a and one or more storage devices or databases 20a. The computing system 18a may take any of a variety of forms, for example, personal computers, mini-computers, work stations, or main frame computers. The computing system 18a may, for example, take the form of a server computer executing server software. The storage or database 20a can take a variety of forms, including one or more hard disks or RAID drives, CD/ROMs, or other mass storage devices.

As discussed in detail below, the test devices 14 are operable to sequentially illuminate an object with a number of bands of electromagnetic energy. The test devices 14 are also operable to detect, measure or otherwise capture electromagnetic energy reflected, emitted, fluoresced, refracted, diffracted or otherwise transmitted, or otherwise returned from the object in response to the illumination. As used herein and in the claims, the terms illuminate, illuminates, illumination, and variations of such terms mean to expose to or reveal by the use of electromagnetic energy or electromagnetic radiation, whether in the visible portion of the electromagnetic spectrum, the optical portion (e.g., visible, near-infrared, near-ultraviolet), or other portions (e.g., far-infrared, far-ultraviolet, microwave, X-ray, etc.).

The network 16a can take a variety of forms, for example one or more local area networks (LANs), wide area networks (WANs), wireless LANs (WLANs), and/or wireless WANs (WWANs). The network 16a may employ packet switching or any other type of transmission protocol. The network 16a may, for example, take the form of the Internet or Worldwide Web portion of the Internet. The network 16a may take the form of public switched telephone network (PSTN) or any combination of the above, or other networks.

A number of the test devices 14a-14f may be logically or physically coupled as a test device system 22a. The test device system 22a may, for example, be associated with a single financial entity such as a business (e.g., corporation, partnership, sole proprietorship, limited liability company), a division of a business, a non-profit, a government (e.g., federal, state or provincial, county or parish, city or town), or division of a government (e.g., agency, department).

The test device system 22a may include one or more server computer systems 24a, and/or one or more personal computing systems 26a, all coupled by a network 28a. The network 28a may take the form of one or more local area networks (LAN) or wide area networks (WAN) and may or may not include wired or wireless access. The network 28a may take the form of an intranet, being restricted to a company or other financial entity. The test device system 22 may, for example, be affiliated with a particular company or financial entity.

A number of the test devices 14g-14h may be wirelessly coupled to the network 16a. One or more of the remote test devices 14i may be coupled to the network 16a via a cradle or other receiver 30. One or more of the test devices 14j may be coupled to the network 16a via a conventional communications interface, for example a USB port of a conventional computing system 32. One or more of the remote test devices 14k may be coupled to the network 16a via a wired connection. For example, the test device 14k may include an integrated phone modem allowing the test device 14k to call into the network 16a.

Figure 2:
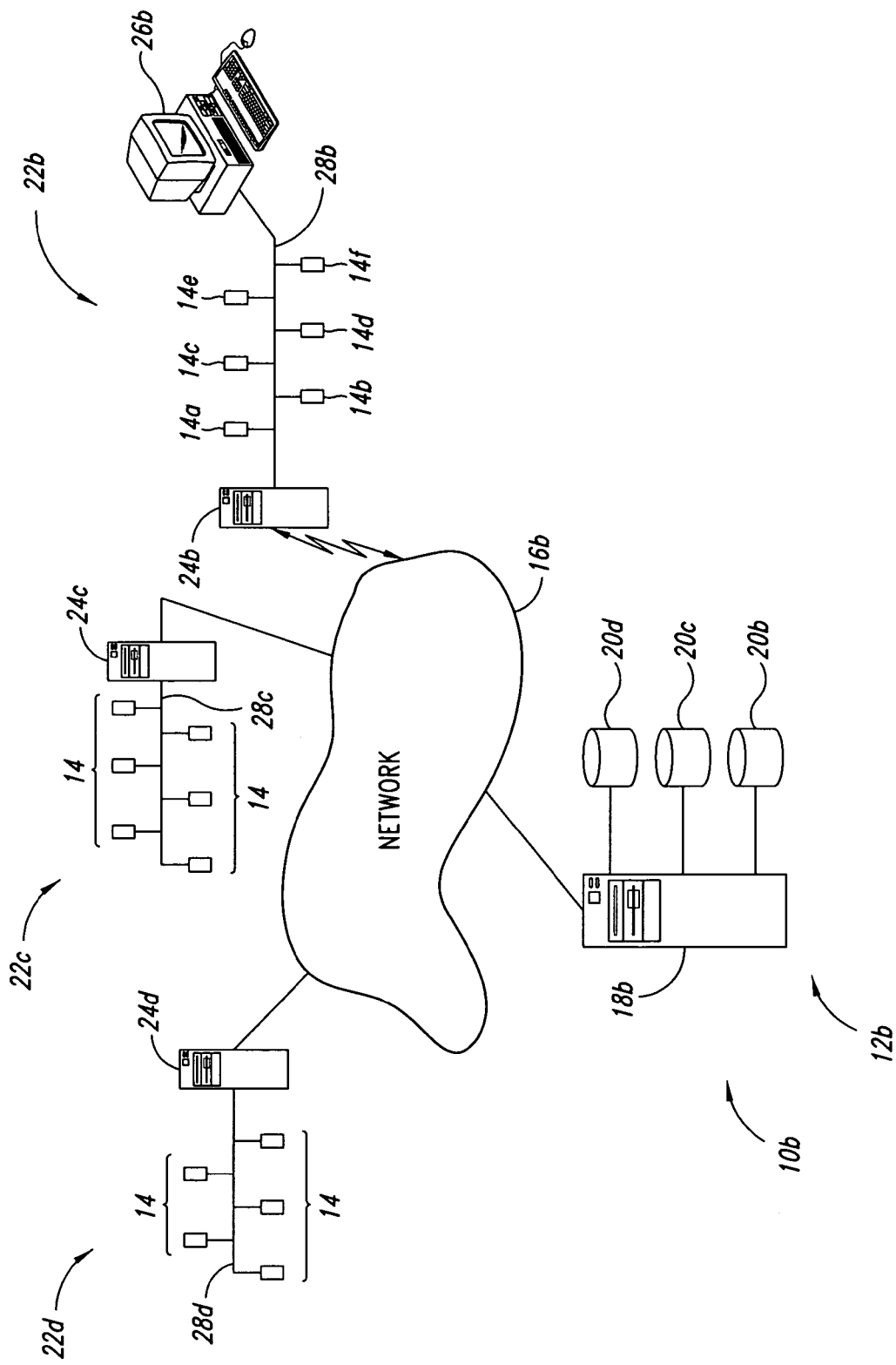
FIG. 2 is a schematic diagram of an object evaluation system including a host system with a plurality of databases associated with respective financial entities, and a plurality of remote test systems, according to another illustrated embodiment.

FIG. 2 shows an object evaluation system 10b according to another illustrated embodiment.

The object evaluation system 10b includes a number of distinct test device systems 22b-22d (collectively 22). The test device systems 22b-22d employ respective networking systems, for example, server computing systems 24b-24d and networks 28b-28d, respectively, to provide communication with the test devices 14. The test device systems 22b-22d may be similar to, or different from, the test device system 22a (FIG. 1) Each of the test device systems 22b-22d may, for example, be associated with a single financial entity such as a business (e.g., corporation, partnership, sole proprietorship, limited liability company), a division of a business, a non-profit, a government (e.g., federal, state or provincial, county or parish, city or town), or division of a government (e.g., agency, department). Some of the test device systems 22c-22d may include a wired connection to the network 16a, while other of the test device systems 22b may include a wireless connection to the network 16a.

The object evaluation system 10b includes one or more host systems 12b. The host system 12b includes one or more computing systems 18b, and a number of distinct storage or databases 20b-20d each associated with a respective financial entity or a respective one of the test device systems 22b-22d, respectively. The computing systems 18b are communicatively coupled to the test device systems 22b-22d via the network 16b.

Figure 3:
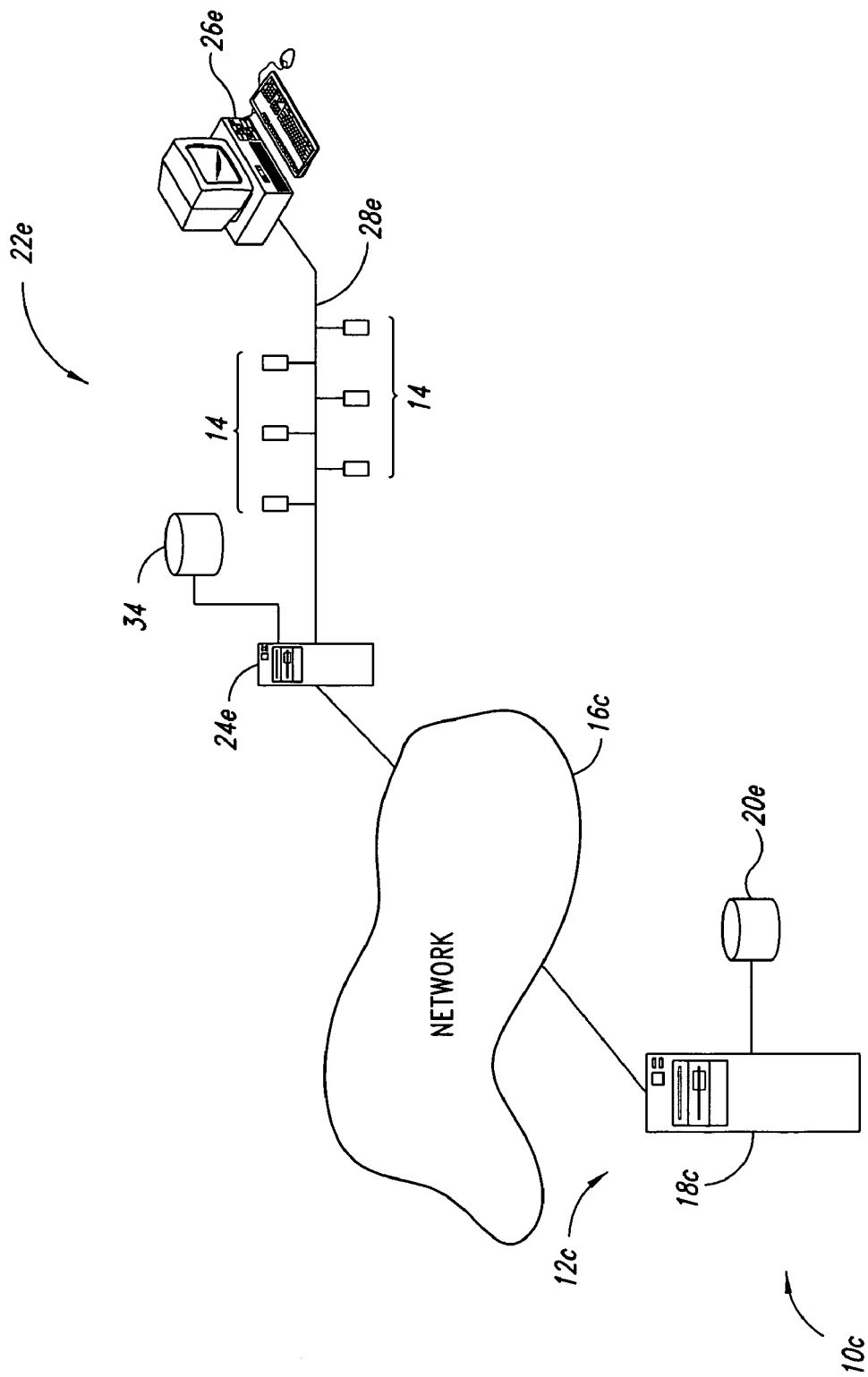
FIG. 3 is a schematic diagram of an object evaluation system including a host system and a test system remotely located from the host system and associated with a financial entity including a respective database, according to another illustrated embodiment.

FIG. 3 shows an object evaluation system 10c according to another illustrated embodiment.

The object evaluation system 10c includes one or more test device systems 22e. The test device system 22e includes one or more computing systems such as server computing system 24e and personal computing system 26e. The test device system 22e also includes a number of test devices 14 communicatively coupled via a network 28e. The network 28e may take a variety of forms including LANs, WANs, WLANs, WWANs, PSTN, to name a few. The test device system 22e further includes a proprietary storage or database 34. The proprietary storage or database 34 may contain executable modules and/or data. For example, the storage or database 34 may contain proprietary reference data that is specific to a financial entity which owns, operates, leases or controls the test device system 22e.

The object evaluation system 10c also includes host system 12c comprising one or more computing systems 18c and storage or databases 20e. The host system 12c is communicatively coupled to a test device system 24e via a network 16c.

Figure 4:
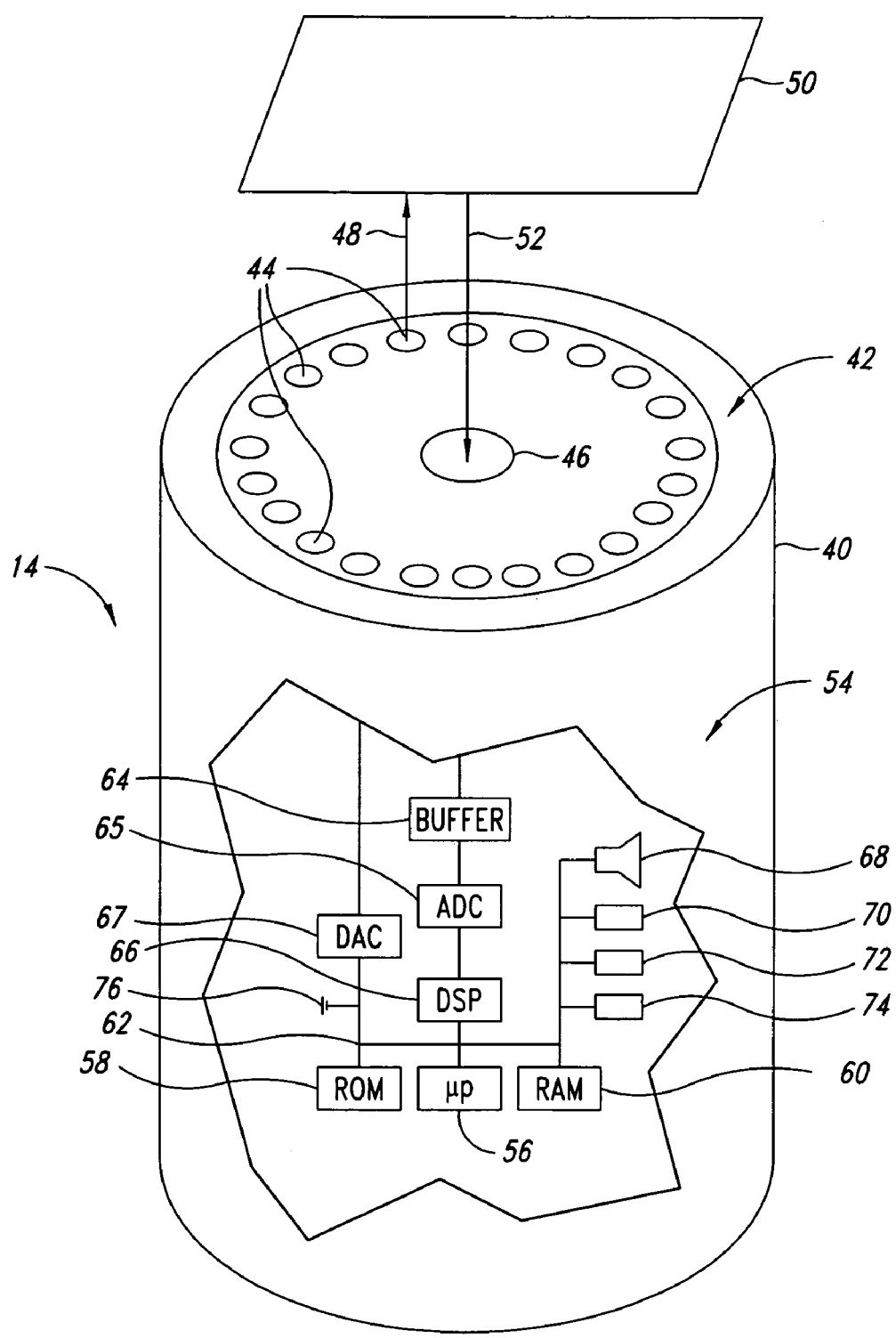
FIG. 4 is a partially cutaway isometric view of a test device illuminating an object, according to one illustrated embodiment.

FIG. 4 shows a test device 14 according to one illustrated embodiment.

The test device 14 may include a housing 40 with an opening or window 42 proximate one end thereof. The test device 14 may include one or more sources 44 (only three called out in FIG. 4) operable to emit electromagnetic energy. While a plurality of sources 44 are illustrated, some embodiments may employ a single source 44. The test device 14 may also include one or more sensors 46 configured and positioned to receive electromagnetic energy returned 52 from the object 50.

The sources 44 may take a variety of forms which are operable to emit electromagnetic energy. The sources 44 may, for example, take the form of one or more light emitting diodes (LEDs). Alternatively, or additionally, the sources 44 may take the form of one or more lasers, for example one or more laser diodes. The lasers may, or may not, be tunable lasers. Alternatively, or additionally, the sources 44 may take the form of one or more incandescent sources such as conventional or halogen light bulbs. Alternatively, or additionally, the sources 44 may take the form of one or more organic LEDs (OLEDs, also referred to in the relevant art as "electronic paper"), which may advantageously be formed on a flexible substrate.

One, more or all of the sources 44 may be operable to emit in part or all of an "optical" portion of the electromagnetic spectrum, including the (human) visible portion, near infrared portion and/or or near ultraviolet portions of the electromagnetic spectrum. Additionally, or alternatively, the sources 44 may be operable to emit electromagnetic energy other portions of the electromagnetic spectrum, for example the infrared, ultraviolet and/or microwave portions.

In some embodiments, at least some of the sources 44 are operable to emit in or at a different band than other of the sources 44. For example, one or more sources 44 may emit in a band centered around 450 nm, while one or more of the sources 44 may emit in a band centered around 500 nm, while a further source or sources emit in a band centered around 550 nm. In some embodiments, each source 44 emits in a band centered around a respective frequency or wavelength, different than each of the other sources 44. Using sources 44 with different band centers advantageously maximizes the number of distinct samples that may be captured from a fixed number of sources 44. This may be particularly advantageous where the test device 14 is relatively small, and has limited space or footprint for the sources 44.

The distribution of spectral content for each source 44 may vary as a function of drive level (e.g., current, voltage, duty cycle), temperature, and other environmental factors, depending on the specific source 44. Such variation may be advantageously actively employed to operate one or more of the physical sources 44 as a plurality of "logical sources," each of the logical sources operable to provide a respective emission spectra from a respective physical source 44. Thus, for example, the center of the band of emission for each source 44 may vary according to a drive level and/or temperature. For example, the center of the band of emission for LEDs will vary with drive current or temperature. One way the spectral content can vary is that the peak wavelength can shift.

However, the width of the band, the skew of the distribution, the kurtosis, etc., can also vary. Such variations may be also be advantageously employed to operate the physical sources 44 as a plurality of logical sources. Thus, even if the peak wavelength were to remain constant, the changes in bandwidth, skew, kurtosis, and any other change in the spectrum can provide useful variations in the operation of the test device 14. Likewise, the center of the band of emission may be varied for tunable lasers. Varying the center of emission bands for one or more sources 44 advantageously maximizes the number of samples that may be captured from a fixed number of sources 44. Again, this may be particularly advantageous where the test device 14 is relatively small, and has limited space or footprint for the sources 44.

A field of emission of one or more sources 44 may be movable with respect to the housing 40. For example, one or more sources 44 may be movable mounted with respect to the housing 40, such as mounted for translation along one or more axes, and/or mounted for rotation or oscillation about one or more axes. Alternatively, or additionally, the test device 14 may include one or more elements operable to deflect or otherwise position the emitted electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, for example permanent magnets or electromagnets such as those associated with cathode ray tubes and/or mass spectrometers.

The sensor 46 can take a variety of forms suitable for sensing or responding to electromagnetic energy. For example, the sensor 46 may take the form of one or more photodiodes (e.g., germanium photodiodes, silicon photodiodes). Alternatively, or additionally, the sensor 46 may take the form of one or more photomultiplier tubes. Alternatively, or additionally, the sensor 46 may take the form of one or more CMOS image sensors. Alternatively, or additionally, the sensor 46 may take the form of one or more charge coupled devices (CCDs). Alternatively, or additionally the sensor 46 may take the form of one or more micro-channel plates. Other forms of electromagnetic sensors may be employed, which are suitable to detect the wavelengths expected to be returned in response to the particular illumination and properties of the object being illuminated.

The sensor 46 may be formed as individual elements, one-dimensional array of elements and/or two-dimensional array of elements. For example, the sensor 46 may be formed by one germanium photodiode and one silicon photodiode, each having differing spectral sensitivities. The test device 14 may employ a number of photodiodes with identical spectral sensitivities, with different colored filters (e.g., gel filters, dichroic filters, thin-film filters, etc) over the photodiodes to change their spectral sensitivity. This may provide a simple, low-cost approach for creating a set of sensors with different spectral sensitivities, particularly since germanium photodiodes are currently significantly more expensive that silicon photodiodes. Also for example, the sensor 46 may be formed from one CCD array (one-dimensional or two-dimensional) and one or more photodiodes (e.g., germanium photodiodes and/or silicon photodiodes). For example, the sensor 46 may be formed as a one- or two-dimensional array of photodiodes. A two-dimensional array of photodiodes enables very fast capture rate (i.e., camera speed) and may be particularly suited to use in assembly lines or high speed sorting operations. For example, the sensor 46 may be formed as a one- or two-dimensional array of photomultipliers. Combinations of the above elements may also be employed.

In some embodiments, the sensor 46 may be a broadband sensor sensitive or responsive over a broad band of wavelengths of electromagnetic energy. In some embodiments, the sensor 46 may be a narrowband sensor sensitive or responsive over a narrow band of wavelengths of electromagnetic energy. In some embodiments, the sensor 46 may take the form of several sensor elements, as least some of the sensor elements sensitive or responsive to one narrow band of wavelengths, while other sensor elements are sensitive or responsive to a different narrow band of wavelengths. This approach may advantageously increase the number of samples that may be acquired using a fixed number of sources. In such embodiments the narrow bands may, or may not, overlap.

A field of view of the sensor 46 or one or more elements of the sensor 46 may be movable with respect to the housing 40. For example, one or more elements of the sensor 46 may be movable mounted with respect to the housing 40, such as mounted for translation along one or more axes, and/or mounted for rotation or oscillation about one or more axes. Alternatively, or additionally, the test device 14 may include one or more elements operable to deflect or otherwise position the returned electromagnetic energy. The elements may, for example, include one or more optical elements, for example lens assemblies, mirrors, prisms, diffraction gratings, etc. For example, the optical elements may include an oscillating mirror, rotating polygonal mirror or prism, or MEMS micro-mirror that oscillates about one or more axes. The elements may, for example, include one or more other elements, example permanent magnets or electromagnets such as those associated with cathode ray tubes and/or mass spectrometers.

In some embodiments, the source 44 may also serve as the sensor 46. For example, an LED may be operated to emit electromagnetic energy at one time, and detect returned electromagnetic energy at another time. For example, the LED may be switched from operating as a source to operating as a detector by reverse biasing the LED. Also for example, an LED may be operated to emit electromagnetic energy at one time, and detect returned electromagnetic energy at the same time.

The test device 14 includes a control subsystem 54. The control subsystem 54 may include a microprocessor 56 and computer-readable media, for example one or more memories such as read only memory (ROM) 58 and random access memory (RAM) 60. One or more buses may couple the ROM 58 and RAM 60 to the microprocessor 56. The buses 62 may take a variety of forms including an instruction bus, data bus, other communications bus and/or power bus. The nonvolatile ROM 58 may store instructions and/or data for controlling the test device 14. The volatile RAM 60 may store instructions and/or data for use during operation of the test device 14.

The control subsystem 54 may optionally include a buffer 64 to buffer information received from the sensor 46. The control subsystem 54 may further optionally include a digital signal processor (DSP) 66 processor coupled to process information received from the sensor 46 via the buffer 64. The control subsystem 54 may further optionally include an analog to digital converter (ADC) 65 and/or digital to analog converter (DAC) 67. An ADC 65 may, for example, be used for converting analog photodiode responses into digital data for further analysis and/or transmission. A DAC 67 may, for example, be used for converting digital computer commands into analog LED current levels. The control subsystem 54 may additionally or alternatively optionally include an analog signal processor, which may be particularly useful where the sensor takes the form of one or more photodiodes.

The control subsystem 54 may include a user interface including one or more user interface devices. For example, the control subsystem 54 may include one or more speakers or microphones 68. Also for example, the control subsystem 54 may include and/or one or more visual indicators 70, such as one or more LEDs, liquid crystal displays (LCD), or other visual indicator. The LCD may, for example, take the form of a touch sensitive LCD, which displays a graphical user interface, operable by the user of the test device 14. Additionally, or alternatively, the control subsystem 54 may include one or more user operable input elements 74, such as switches or keys. The input elements 74 may include a switch for turning the test device ON and OFF. Additionally, or alternatively, the input elements 74 may include one or more switches or keys for controlling the operation of the test device 14, for example, downloading or uploading data or instructions to, or from the test device.

The control subsystem 54 may further include one more communication ports 72, for example, a USB port, infrared transceiver, or RF transceiver. Such may allow the transmission of data, instructions and/or results, to or from the test device 14.

The test device 14 may also include a power source 76. The power source may take the form of a portable power source, for example one or more batteries, fuel cells, and/or super- or ultra-capacitors. Additionally, or alternatively, the power source 76 may take the form of a fixed power source, such as a cable plugged into a port of a computer or a conventional electrical receptacle (e.g., wall outlet).

The microprocessor 56 employs instructions and or data from the ROM 58 and RAM 60 in controlling operation of the test device 14. For example, the microprocessor 56 operates the sources 44 in one or more sequences. The sequences determine an order in which the sources 44 are turned On and Off. The sequences may also indicate an ordered pattern of drive levels (e.g., current levels, voltage levels, duty cycles) for the sources 44. Thus, for example, a microprocessor 56 may cause the application of different drive levels to respective ones of the sources 44 to cause the sources 44 to emit in distinct bands of the electromagnetic spectrum. The DSP 66 and/or microprocessor 56 may process information generated by the sensor 46, which is indicative of the response by at least a portion of the object 50 to illumination by the sources 44. The information at any given time may be indicative of the response by the object 50 to illumination by one or more of the sources 44. Thus, the information over a period of time may be indicative of the responses by the object 50 to sequential illumination by each of a plurality of the sources 44, where each of the emission spectra of each of the sources 44 has a different center, bandwidth and/or other more complex differences in spectral content, such as those described above (e.g., width of the band, the skew of the distribution, the kurtosis, etc.).

Computing Systems

Figure 5:
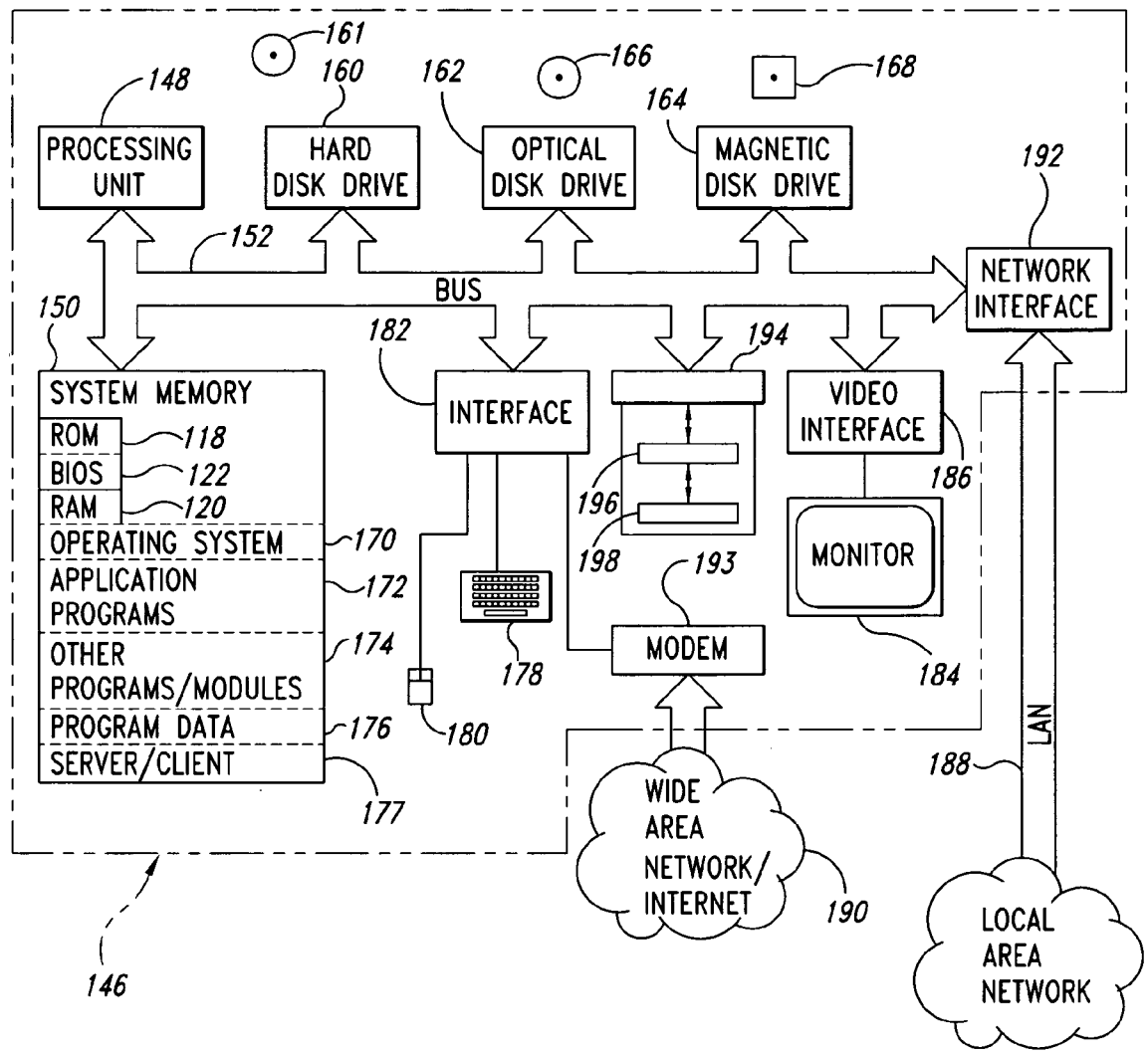
FIG. 5 is a functional block diagram of a computing system suitable for use as the host system of FIGS. 1-3 or other computing system, according to one illustrated embodiment.

FIG. 5 shows a conventional personal computer referred to herein as computing system 146 that may be appropriately configured to function as either the computing system 18 of the host system 12 (FIG. 1-3), the personal computing system 26 of the test device system 22, and/or conventional computing system 32.

The computing system 146 includes a processing unit 148, a system memory 150 and a system bus 152 that couples various system components including the system memory 150 to the processing unit 148. The processing unit 148 may be any logical processing unit, such as one or more central processing units (CPUs), digital signal processors (DSPs), application-specific integrated circuits (ASICs), field programmable gate arrays (FPGAs), etc. Unless described otherwise, the construction and operation of the various blocks shown in FIG. 5 are of conventional design. As a result, such blocks need not be described in further detail herein, as they will be understood by those skilled in the relevant art.

The system bus 152 can employ any known bus structures or architectures, including a memory bus with memory controller, a peripheral bus, and/or a local bus. The system memory 150 includes ROM 154 and RAM 156. A basic input/output system ("BIOS") 158, which can form part of the ROM 154, contains basic routines that help transfer information between elements within the computing system 146, such as during startup.

The computing system 146 also includes one or more spinning media memories such as a hard disk drive 160 for reading from and writing to a hard disk 161, and an optical disk drive 162 and a magnetic disk drive 164 for reading from and writing to removable optical disks 166 and magnetic disks 168, respectively. The optical disk 166 can be a CD-ROM, while the magnetic disk 168 can be a magnetic floppy disk or diskette. The hard disk drive 160, optical disk drive 162 and magnetic disk drive 164 communicate with the processing unit 148 via the bus 152. The hard disk drive 160, optical disk drive 162 and magnetic disk drive 164 may include interfaces or controllers coupled between such drives and the bus 152, as is known by those skilled in the relevant art, for example via an IDE (i.e., Integrated Drive Electronics) interface. The drives 160, 162 and 164, and their associated computer-readable media 161, 166 and 168, provide nonvolatile storage of computer-readable instructions, data structures, program modules and other data for the computing system 146. Although the depicted computing system 146 employs hard disk 161, optical disk 166 and magnetic disk 168, those skilled in the relevant art will appreciate that other types of spinning media memory computer-readable media may be employed, such as digital video disks ("DVDs"), Bernoulli cartridges, etc. Those skilled in the relevant art will also appreciate that other types of computer-readable media that can store data accessible by a computer may be employed, for example, non-spinning media memories such as magnetic cassettes, flash memory cards, RAMs, ROMs, smart cards, etc.

Program modules can be stored in the system memory 150, such as an operating system 170, one or more application programs 172, other programs or modules 174, and program data 176. The applications programs 172 may include one or more programs for: locating test devices 14, downloading instructions such as executable modules to test devices 14, uploading responses to illumination from test devices 14, selecting appropriate test sequences, analyzing results of the test sequences, and delivering the analysis to the test devices 14. The system memory 150 also includes one or more communications programs 177 for permitting the computing system 146 to access and exchange data with sources such as websites of the Internet, corporate intranets, or other networks, as well as other server applications on server computers. The communications program 177 may take the form of one or more server programs. Alternatively, or additionally, the communications program may take the form of one or more browser programs. The communications program 177 may be markup language based, such as hypertext markup language ("HTML"), Extensible Markup Language (XML) or Wireless Markup Language (WML), and operate with markup languages that use syntactically delimited characters added to the data of a document to represent the structure of the document. A number of Web clients or browsers are commercially available such as NETSCAPE NAVIGATOR® from America Online, and INTERNET EXPLORER® available from Microsoft Corporation of Redmond Wash.

While shown in FIG. 5 as being stored in the system memory 150, the operating system 170, application programs 172, other program modules 174, program data 176 and communications program 177 can be stored on the hard disk 161 of the hard disk drive 160, the optical disk 166 of the optical disk drive 162 and/or the magnetic disk 168 of the magnetic disk drive 164.

A user can enter commands and information to the computing system 146 through input devices such as a keyboard 178 and a pointing device such as a mouse 180. Other input devices can include a microphone, joystick, game pad, scanner, button, key, microphone with voice recognition software, etc. These and other input devices are connected to the processing unit 148 through an interface 182 such as a serial port interface that couples to the bus 152, although other interfaces such as a parallel port, a game port or a universal serial bus ("USB") can be used. A monitor 184 or other display devices may be coupled to the bus 152 via video interface 186, such as a video adapter. The computing system 146 can include other output devices such as speakers, printers, etc.

The computing system 146 can operate in a networked environment 10 (FIGS. 1-3) using logical connections to one or more remote computers. The computing system 146 may employ any known means of communication, such as through a local area network ("LAN") 188 or a wide area network ("WAN") or the Internet 190. Such networking environments are well known in enterprise-wide computer networks, intranets, extranets, and the Internet.

When used in a LAN networking environment, the computing system 146 is connected to the LAN 188 through an adapter or network interface 192 (communicatively linked to the bus 152). When used in a WAN networking environment, the computing system 146 often includes a modem 193 or other device for establishing communications over the WAN/Internet 190. The modem 193 is shown in FIG. 5 as communicatively linked between the interface 182 and the WAN/Internet 190. In a networked environment, program modules, application programs, or data, or portions thereof, can be stored in a server computer (not shown). Those skilled in the relevant art will readily recognize that the network connections shown in FIG. 5 are only some examples of establishing communications links between computers, and other communications links may be used, including wireless links.

The computing system 146 may include one or more interfaces such as slot 194 to allow the addition of devices 196, 198 either internally or externally to the computing system 146. For example, suitable interfaces may include ISA (i.e., Industry Standard Architecture), IDE, PCI (i.e., Personal Computer Interface) and/or AGP (i.e., Advance Graphics Processor) slot connectors for option cards, serial and/or parallel ports, USB ports (i.e., Universal Serial Bus), audio input/output (i.e., I/O) and MIDI/joystick connectors, and/or slots for memory.

The term "computer-readable medium" as used herein refers to any medium that participates in providing instructions to processing unit 148 for execution. Such a medium may take many forms, including but not limited to, non-volatile media, volatile media, and transmission media. Non-volatile media includes, for example, hard, optical or magnetic disks 161, 166, 168, respectively. Volatile media includes dynamic memory, such as system memory 150. Transmission media includes coaxial cables, copper wire and fiber optics, including the wires that comprise system bus 152. Transmission media can also take the form of acoustic or light waves, such as those generated during radio wave and infrared data communications.

Common forms of computer-readable media include, for example, floppy disk, flexible disk, hard disk, magnetic tape, or any other magnetic medium, CD-ROM, any other optical medium, punch cards, paper tape, any other physical medium with patterns of holes, RAM, PROM, EPROM, EEPROM, FLASH memory, any other memory chip or cartridge, a carrier wave as described herein, or any other medium from which a computer can read.

Various forms of computer readable media may be involved in carrying one or more sequences of one or more instructions to processing unit 148 for execution. For example, the instructions may initially be carried on a magnetic disk of a remote computer. The remote computer can load the instructions into its dynamic memory and send the instructions over a telephone line using a modem. A modem 193 local to computer system 146 can receive the data on the telephone line and use an infrared transmitter to convert the data to an infrared signal. An infrared detector coupled to the system bus 152 can receive the data carried in the infrared signal and place the data on system bus 152. The system bus 152 carries the data to system memory 150, from which processing unit 148 retrieves and executes the instructions. The instructions received by system memory 150 may optionally be stored on a storage device either before or after execution by processing unit 148.

FIG. 6 shows a data structure 200 which may be stored in one of the storage media or databases 161, 166, 168 (FIG. 5), 20, 34 (FIGS. 1-3), 58, 60 (FIG. 4), according to one illustrated embodiment.

The data structure 200 stores reference responses 202 (only one called out, illustrated in column 204) for various objects 50 (FIG. 4) identified by object identifiers 206 (only one called out, illustrated in column 208).

The data structure 200 may store a reference response 202 for a variety of objects 50, for example a specific handbag or type of handbag 210. The data structure 200 may store reference responses for media, for example: identification documents such as passports, identity cards (e.g., national, state, provincial, military, employer, school, organization), driver's licenses, and/or birth or naturalization certificates; financial documents such as currency 212, checks, bonds, and/or securities; and/or legal documents such as licenses, permits, assignments, deeds, wills, declarations, oaths, agreements, pleadings, or motions. The data structure 200 may also store reference responses 202 for tissue 214, for example, reference responses that identify (e.g., unique individual) or characterize (e.g., normal, abnormal) bodily tissue such as retinal tissue or blood. The data structure 200 may additionally, or alternatively, store data corresponding to a manufacturing process, such as reference responses for various processing steps for curing rubber 216. The data structure 200 may additionally, or alternatively, store data related to quality control, for example, reference responses for properly homogenized milk 218.

The data structure 200 may include an object type identifier 220 (only one called out in FIG. 6, illustrated in column 222). The object type identifier may provide a general and/or specific description of the type of object (e.g., handbag, currency, U.S. Ten Dollar Note, retinal tissue, semiconductor circuit masking operation, etc.). Additionally, or alternatively, the object type identifier 220 may provide broad and/or specific description of the physical characteristics of the object type (e.g., paper, MYLAR®, canvas, A4, serial number, leather, green, 36° C., 5 foot and 11 inches, 160 pounds, brown hair, etc.).

For each object 50, the data structure 200 may store reference responses 202 corresponding to respective physical and or logical sources 44 (FIG. 4) or the respective emission spectra for sources 44. For example, the data structure 200 stores reference responses 202 for a number of sources 44 or respective emission spectra 224a-224e (collectively 224) for the handbag 210. The emission spectra 224 may be represented in a variety of ways, for example as one-dimensional or multi-dimensional functions or waveforms or as individual values indicative of one or more characteristics, for example peak wavelength or primary band.

The data structure 200 may store reference responses 202 at a variety of drive levels for each of the sources 44. For example, the data structure 200 may store reference responses 202 at current levels 228a-228c (only three called out in FIG. 6, collectively 228, illustrated in column 230). While the reference responses 202 are illustrated as one-dimensional functions or waveforms, the reference responses may take any of a variety of forms. For example, in some embodiments each of the reference responses 202 with take the form of a single value or number for a given object, source, drive-level and/or temperature combination. In other embodiments, each of the reference responses 202 may take the form of a multi-dimensional function or waveform (e.g., two, three or greater dimensions). Such may be suitable where, for example, the sensor 46 takes the form of a CCD array, rather than a photodiode.

Additionally, the data structure 200 may include reference responses 202 where the source 44 and/or sensor 46 is at a variety of temperatures 232a, 232b (only two called out in FIG. 6, illustrated in column 234). This allows for variance in emission spectra and/or reception to be accounted for in the data structure 200. Thus, identification of a source 44, a driving level 228 and/or a temperature may allow selection of an appropriate reference response 202 for use in analyzing test data measured or determined by the test device 14, as further explained below.

Additionally, or alternatively, the data structure 200 may include reference responses 202 for a variety of sensor sensitivities 236a, 236b (only two called out in FIG. 6, illustrated in column 238). This allows for variance in sensitivity of various sensors 46 to be accounted for in the data structure 200. Thus, identification of a sensor 46 may allow selection of an appropriate reference response 202 for use in analyzing test data measured or determined by the test device 14, as further explained below.

The data structure 200 may additionally include location or position information that identifies a location or position on the reference object from which the reference response was taken and/or the positions of the sources(s) 44 and/or sensor (s) 46 relative to the reference object. Reference responses from multiple locations on a reference object may be stored in the data structure 200. Varying the location of testing or sampling may further contribute to the inherent encryption associated with varying the sequence.

FIGS. 7-51 show methods of operating the host evaluation system 12 (FIGS. 1-3), computing system 18 and/or test device 14, according to various embodiments.

Figure 7:
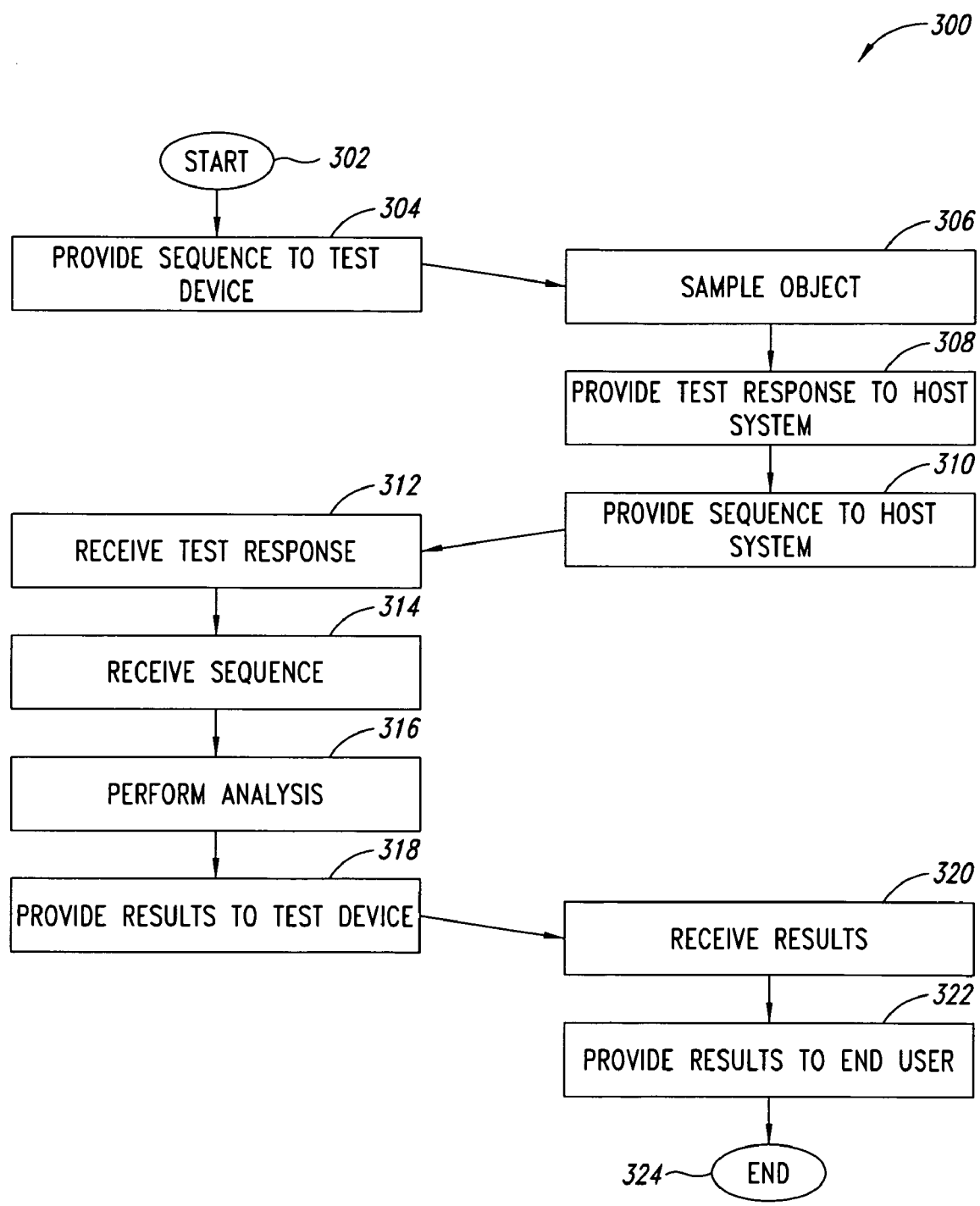
FIG. 7 is a flow diagram showing a method of operating a computing system and a test device remotely located with respect to the host system, the method employing both inherent and conventional encryption techniques to operate in a secure manner, according to one illustrated embodiment.

FIG. 7 shows a method 300 of operating the computing system 18 (FIGS. 1-3) of the host system 12 and test device 14, according to one illustrated embodiment. FIG. 7 generally illustrates operations of the computing system 18 of the host evaluation system 12 in a column on the left side of the Figure, while operations of the test device 14 are generally illustrated in a column on the right side of the figures. The flow of operation is generally illustrated by vertically extending arrows. The flow of data between the computing system 18 or host evaluation system 12 and the test device 14 is generally illustrated by arrows extending between the right and left columns of FIG. 7.

The method 300 starts at 302. For example, the method 300 may start in response to activation of the computing system 18 and/or test device 14. Alternatively the method 300 may start in response to a user input, receipt of data or instructions, or receipt of a signal from a sensor.

Optionally at 304, the computing system 18 provides a sequence to the test device 14. The sequence defines an order of activation for the sources 44, and may optionally define a sequence of drive levels and/or temperatures for respective ones of the sources 44 within the sequence. In some embodiments, the sequence can be varied periodically. In other embodiments, the sequence may be varied randomly. In further embodiments, the sequence may be varied with each iteration. In still other embodiments, the sequence may be varied based on a time which may reflect the current date. The sequence may be generated using a random number generator (RNG), may be selected from a set of sequences stored in the memory or database, and/or generated based at least in part on a current time which may reflect a current date.

Varying the sequence may advantageously provide a level of security, introducing an inherent encryption. of the signals indicative of the test responses and/or the results. The variation makes it difficult for someone to determine or fake test responses for a given object since the test response varies based on the particular illumination sequence employed. Additionally, the differences in sources 44 (e.g., LED composition), between test devices 14, creates a unique signature for responses taken from each test device 14. A knowledge of this unique signature may be used in calibration for decoding the test response provided by the specific test device 14, so it can also be considered an inherent form of encryption. Inherent encryption may be particularly advantageous where security is a concern, for example where identity documents are being authenticated, where financial instruments are being authenticated, wherein medical documents are being authenticated, or where goods are being authenticated to detect forgeries. As noted, the sequence may be varied randomly, periodically, based on time and/or date, or on demand. This inherent variation may be bolstered by more conventional encryption, for example public/private key encryption, for example RSA encryption. Thus, the test response may be encrypted using conventional encryption techniques. Additionally, or alternatively, the sequence may be encrypted using conventional encryption techniques. Additionally, or alternatively, if the sequence is transmitted, it may be transmitted separately from the test results, reducing the likelihood of interception of both. It should be noted that even if both the sequence and resulting test response were intercepted, such information would have limited value since the sequence would or could soon be changed. Such is discussed in more detail in commonly assigned U.S. provisional patent application 60/834,662, filed Jul. 31, 2006 using Express Mail No. EV448396842US.

At 306, the test device 14 samples an object 50. The test device samples the object by sequentially illuminating the object with a number of bands of electromagnetic energy. The test device 14 further samples the object by measuring or otherwise determining a response by the object 50 to the illumination. In particular, the sensor 46 (FIG. 4) captures electromagnetic energy returned from the object 50 being subjected to the test. The returned electromagnetic energy may take the form of electromagnetic energy reflected, fluoresced, or otherwise returned from the object 50. The returned electromagnetic energy is the response by the object 50 to the particular illumination during the relevant period.

At 308, the test device 14 provides a signal indicative of the response or captured electromagnetic energy to the computing system 18 of the host system 12. Some embodiments may perform analysis of the response at the test device 14, rendering 308 optional.

Optionally at 310, the test device 14 provides the sequence to the computing system 18 of the host system 12. This may be particularly useful where the computing system 18 did not provide the sequence to the test device 14 or where the test device 14 and computing system 18 are not otherwise synchronized. For example, this may be particularly useful where the test device 14 employs one or more sequences that are stored or preconfigured at the test device 14. Providing of the sequence may be omitted, for example, where the computing system 18 provides the sequence, hence the sequence is known to the computing system. In such situations, the test device 14 may nevertheless provide the sequence to the computing system 18, which may serve as a confirmation or may reduce the amount of computational overhead that would otherwise be required to track relationships between test devices 14 and sequences. In some embodiments, the test device 14 may provide the sequence along (e.g., in the same communications or packet) with the test response. Some embodiments may provide the sequence separately from the test response, which may increase the security of communications since two separate messages would need to be intercepted and related to one another.

Optionally at 312, the computing system 18 receives the test response. Optionally at 314, the computing system 18 receives the sequence.

Optionally at 316, the computing system 18 performs an analysis on the test response based on the sequence. The computing system 18 or test device 14 may perform calibration on the test response and/or expected or reference responses as part of the analysis or prior to the analysis. The calibration may be based on a variety of factors or parameters. For example, the calibration may be based on a temperature at which the source 44 and/or sensor 46 is operating or expected to be operating. For example, where the sources 44 are LEDs, variations in emission spectra based on temperature may be accommodated. Also for example, the calibration may be based on the properties of specific sources 44. For example, where the sources 44 are LEDs variations in emission spectra based on manufacturing differences between specific sources 44 may be accommodated. For example, variations between different manufactures, different batches of sources 44 by the same manufacturer, or even between individual sources 44 in the same manufacturing batch may be accommodated.

Optionally at 318, the computing system 18 provides results to the test device 14. As noted above, some embodiments may perform the analysis at the test device 14 rendering 312, 314, 316 and 318 optional.

Optionally at 320, the test device 14 receives the results from the computing system 18. At 322, the test device 14 provides results to the end user, for example, via one or more elements 68, 70 of the user interface.

The method 300 terminates at 324. In some embodiments, the method 300 would return control back to 302, in lieu of terminating at 324. For example, some embodiments may attempt to find matches for more than one sequence, at more than one location, and/or at more than one viewpoint or angle. In other embodiments the method 300 may operate as separate processes or threads, in parallel or concurrently with one another.

Figure 8:
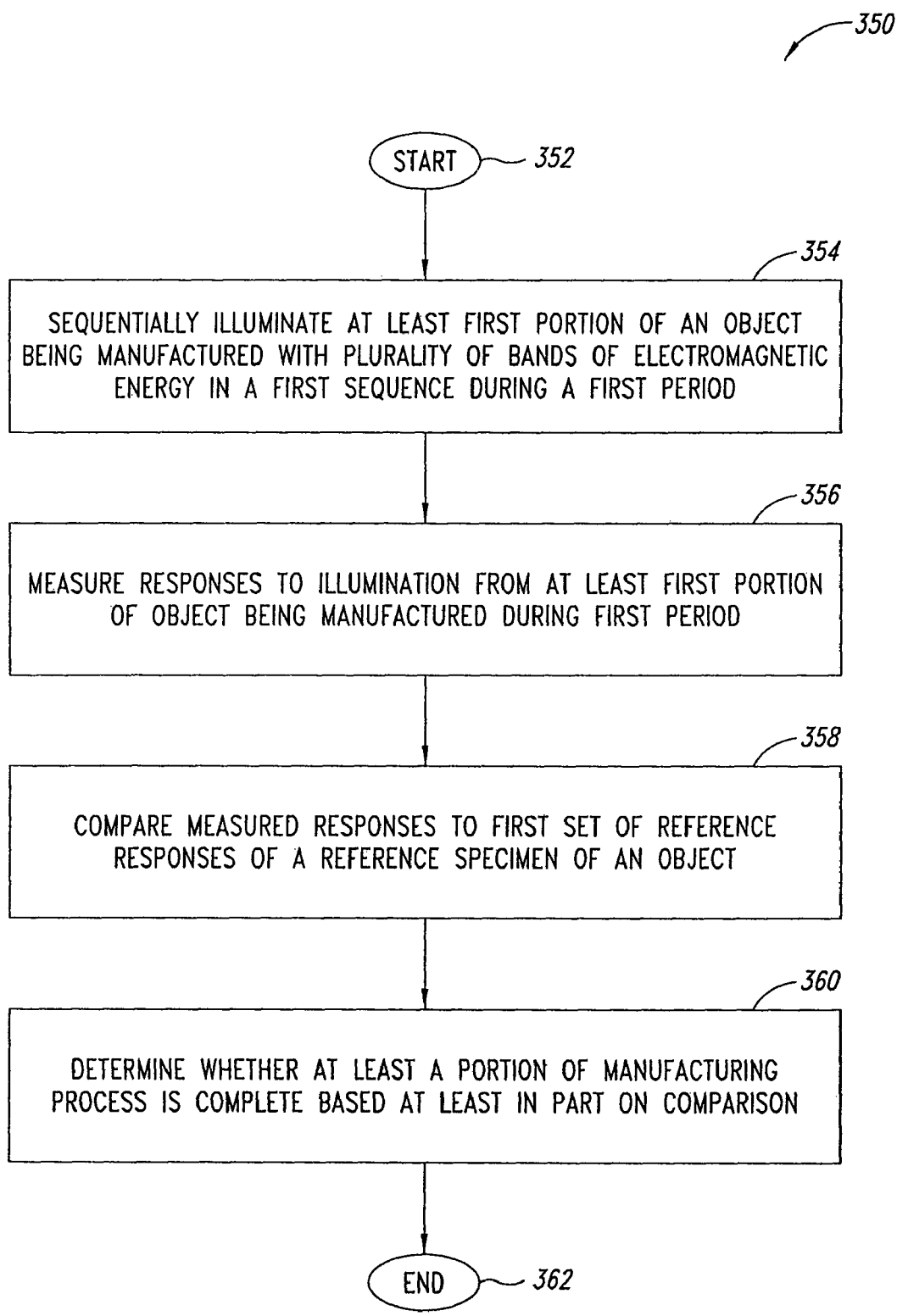
FIG. 8 is a flow diagram showing a method of operating a test device and/or a computing system of an evaluation system useful in controlling a manufacturing process, according to one illustrated embodiment.

FIG. 8 shows a method 350 of operating the test device 14 and/or computing system 18, according to one illustrated embodiment. The method 350 may be useful in manufacturing an object 50.

The method 350 starts at 352. For example, the method 350 may start in response to the activation or powering of the computing device 18 or test device 14. Alternatively, the method 350 may start in response to a user input, receipt of data or instructions, or receipt of a signal from a sensor.

At 354, the test device 14 sequentially illuminates at least the first portion of an object 50 being manufactured with a plurality of bands of electromagnetic energy, in a first sequence during a first period. At 356, the sensor 46 measures responses to the illumination from at least the first portion of the object during the first period.

At 358, the test device 14 or computing system 18 compares measured or test responses to the first set of reference responses 202 (FIG. 6) of a reference specimen of an object. The reference responses 202 may be part of the reference data may be provided from one or more of the test devices 14 or computers 26, 32 associated with equipment for capturing the reference data. The reference data may include reference responses 202 which may take the form of responses by reference objects to defined illumination. For example, reference responses 202 may take the form of signals indicative of electromagnetic energy received from an object 50 in response to illumination with a known bandwidth of electromagnetic energy, by a known source 44, at a known drive level (e.g., current, voltage, duty cycle) and/or known temperature.

In some embodiments, the measured or test response is compared to reference responses 202 until a match within some defined threshold is found. The threshold may be preset or may be determined during operation, and may or may not be user configurable. In other embodiments, the measured or test response is compared to all reference responses in the set of reference responses. In such embodiments, all matches within a defined threshold may be identified and reported to the end user. Alternatively, only the best or closest matching response or responses may be identified and reported to the end user. Such may include one or more indications of confidence in the match, such as a confidence level that indicates a degree of matching. The confidence level may be represented in a variety of ways, for example as a percentage of discrepancies detected or how many standard deviations the match is from being an identical match. Alternatively, the confidence level may indicate the number of times a match with a threshold was found. For example, if a match was found in response to more than one sequence, at more than one location, and/or at more than one viewpoint or angle.

At 360, the test device 14 or computing system 18 determines whether at least a portion of the manufacturing process is complete based at least in part on the comparison. For example, an object 50 may have a particular spectral response to a sequence of illumination at a particular point in the manufacturing process (e.g., baking, cooking, curing, annealing, polishing, etching, depositing, machining, etc.). Completion of the portion of the manufacturing process may be determined to be complete once the object 50 produces the desired spectral response.

The method 350 terminates at 362. In some embodiments, the method 350 would return control back to 352, in lieu of terminating at 362. In other embodiments, the method 350 may operate as separate processes or threads, in parallel or concurrently with one another.

Figure 9:
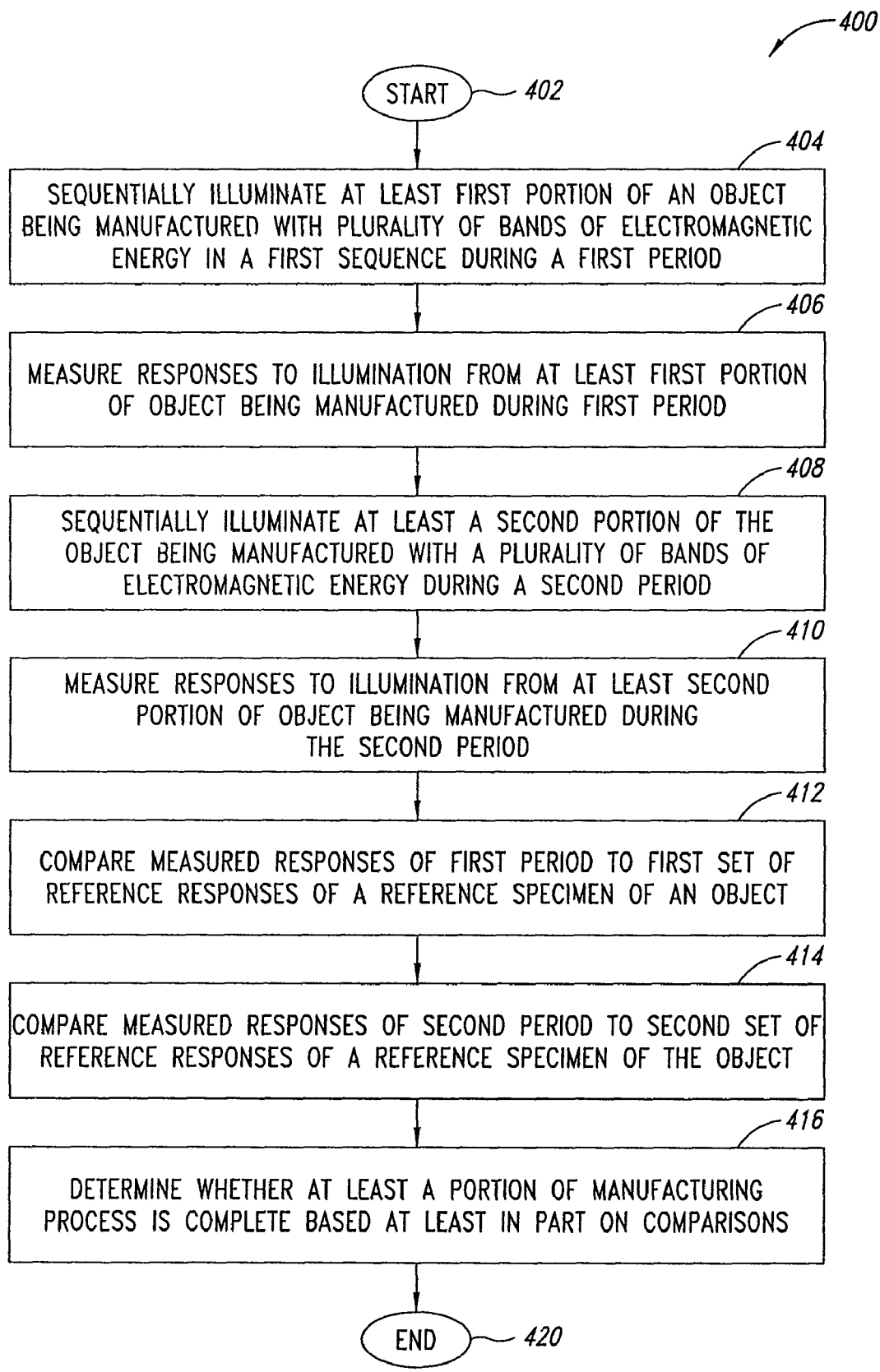
FIG. 9 is a flow diagram showing a method of operating a test device and/or a computing system of an evaluation system useful in controlling a manufacturing process, according to another illustrated embodiment.

FIG. 9 shows a method 400 of operating the test device 14 and/or computing system 18, according to another illustrated embodiment. The method 400 may be used in manufacturing an object 50.

The method 400 starts at 402. For example, the method 400 may start in response to the activation or powering of the test device 14 or computing system 18. Alternatively, the method 400 may start in response to a user input, receipt of data or instructions, or receipt of a signal from a sensor.

At 404, the test device 14 sequentially illuminates at least a first portion of an object 50 being manufactured with a plurality of bands of electromagnetic radiation, in a first sequence during a first period. At 406, the sensor 46 (FIG. 4) measures responses to the illumination from at least the first portion of the object 50 during the first period. At 408, the test device 14 sequentially illuminates at least the second portion of the object 50 being manufactured with a plurality of bands of electromagnetic energy, during a second period. At 410, the sensor 46 measures a plurality of responses to the illumination from at least the second portion of the object 50 being manufactured, during the second period.

At 412, the test device 14 or computing system 18 compares the measured or test responses to a first set of reference responses of a reference specimen of an object. At 414, the test device 14 or computing system 18 compares measured or test responses of the second period to a second set of reference responses to illumination of the reference specimen of the object. At 416, the test device 14 or computing system 18 determines whether at least a portion of the manufacturing process is complete, based at least in part on the comparisons. Sampling at two or more different locations on the object 50 may produce more reliable results than sampling at a single location.

The method 400 terminates at 420. In some embodiments, the method 400 would return control back to 402, in lieu of terminating at 420. In other embodiments, the method 400 may operate as separate processes or threads, in parallel or concurrently with one another.

Figure 10:
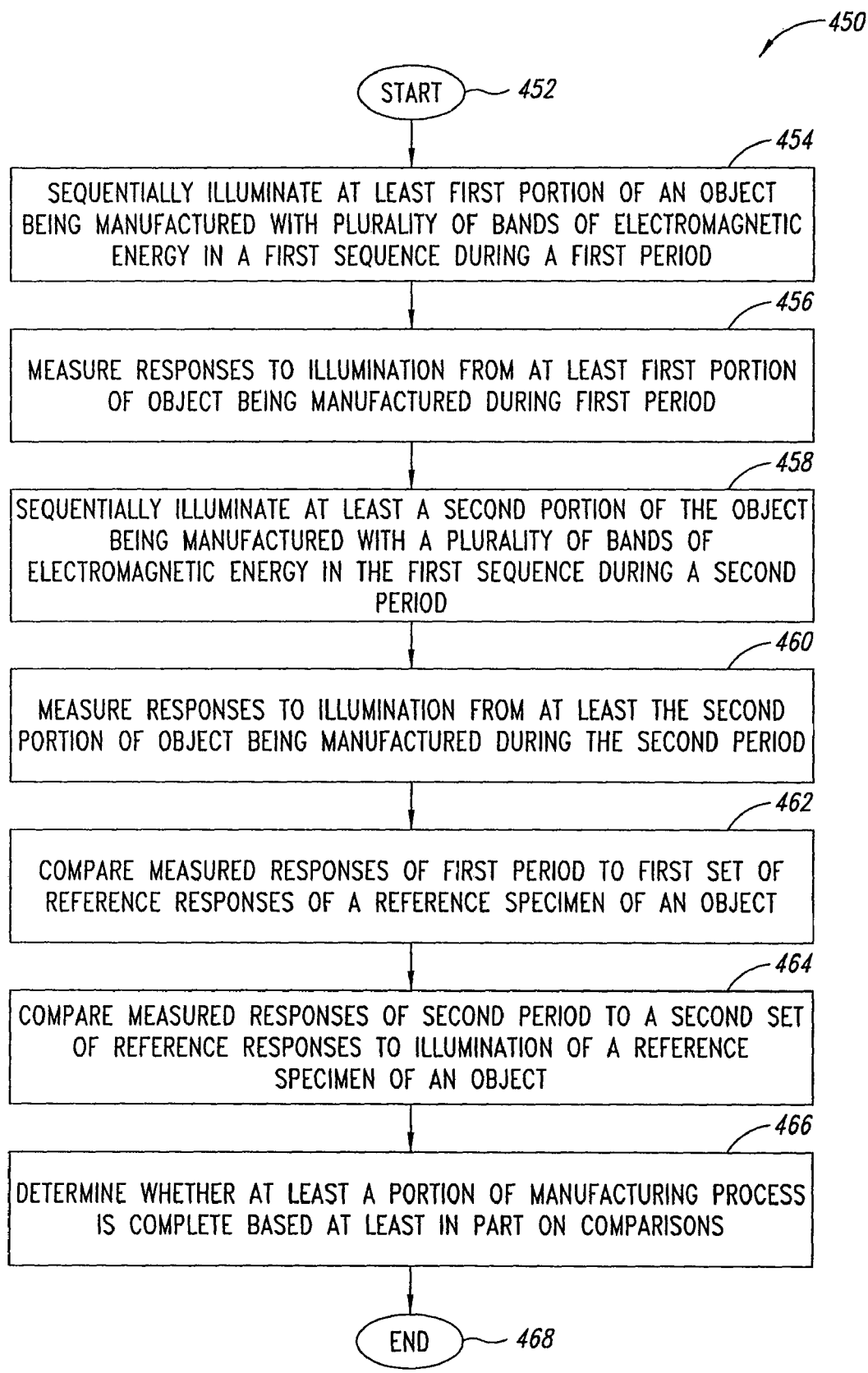
FIG. 10 is a flow diagram showing a method of operating a test device and/or a computing system of an evaluation system useful in controlling a manufacturing process, according to yet another illustrated embodiment.

FIG. 10 shows a method 450 of operating the test device 14 and/or computing device 18, according to another illustrated embodiment. The method 450 may be useful in the manufacture of an object 50.

The method 450 starts at 452. For example, the method 450 may start in response to activation or powering of the test device 14 or computing system 18. Alternatively, the method 450 may start in response to a user input, receipt of data or instructions, or receipt of a signal from a sensor.

At 454, the test device 14 sequentially illuminates at least a first portion of an object 50 being manufactured with a plurality of bands of electromagnetic energy, in a first sequence during a first period. At 456, the sensor 46 (FIG. 4) measures responses to the illumination from at least the first portion of the object during the first period. At 458, the test device 14 sequentially illuminates at least the second portion of the object 50 being manufactured with a plurality of bands of electromagnetic energy, in the first sequence during a second period. At 460, the sensor 46 measures responses to the illumination from at least the second portion of the object 50 being manufactured during the second period.

At 462, the test device 14 or computing system 18 compares the measured or test responses to the first set of reference responses of a reference specimen of an object. At 464, the test device 14 or computing system 18 compares measured or test responses of the second period to a second set of reference responses of the reference specimen of the object. At 466, the test device 14 or computing system 18 determines whether at least a portion of the manufacturing process is complete, based at least in part on the comparisons. Sampling at different times may facilitate or implement a feedback process, timely terminating the portion of the manufacturing process to prevent the manufacturing process from over processing the object 50. Additionally, sampling at different times may produce more reliable results, for example, requiring two or more matches before terminating the portion of the manufacturing process.

The method 450 terminates at 468. In some embodiments, the method 450 would return control back to 452, in lieu of terminating at 468. In other embodiments, the method 450 may operate as separate processes or threads, in parallel or concurrently with one another.

Figure 11:
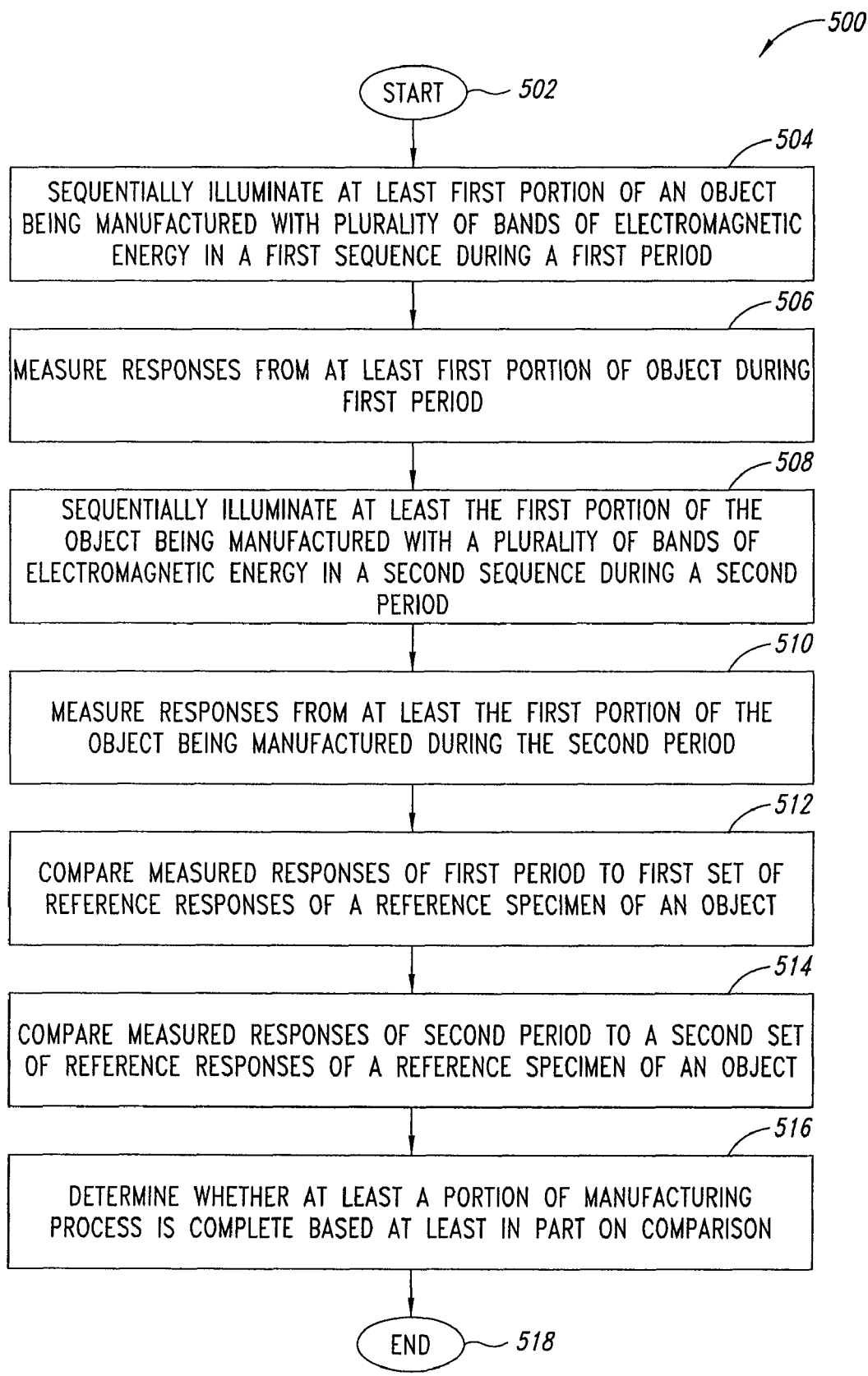
FIG. 11 is a flow diagram showing a method of operating a test device and/or a computing system of an evaluation system useful in controlling a manufacturing process, according to still another illustrated embodiment.

FIG. 11 shows a method 500 of operating the test device 14 and/or computing system 18, according to another illustrated embodiment. The method 500 may be useful in the manufacturing of an object 50.

The method 500 starts at 502. For example, the method 500 may start in response to activation or powering of the test device 14 and/or computing system 18. Alternatively, the method 500 may start in response to a user input, receipt of data or instructions, or receipt of a signal from a sensor.

At 504, the test device 14 sequentially illuminates at least the first portion of an object 50 being manufactured with a plurality of bands of electromagnetic energy, in a first sequence during a first period. At 506, the sensor 46 (FIG. 4) measures responses from at least the first portion of the object 50 during the first period. At 508, the test device 14 sequentially illuminates at least the first portion of the object 50 being manufactured with a plurality of bands of electromagnetic energy, in a second sequence during a second period. At 510, the sensor 46 measures responses from at least the first portion of the object 50 being manufactured during the second period.

At 512, the test device 14 or computing system 18 compares measured or test responses of the first period to a first set of reference responses of a reference specimen of an object. At 514, the test device 14 or computing system 18 compares the measured or test responses of the second period to a second set of reference responses of the reference specimen of the object. At 516, the test device 14 or computing system 18 determines whether at least a portion of the manufacturing process is complete, based at least in part on the comparisons.

The method 500 terminates at 518. In some embodiments, the method 500 may return control back to 502, in lieu of terminating at 518. In other embodiments, the method 500 may operate as separate processes or threads, in parallel or concurrently with one another.

Figure 12:
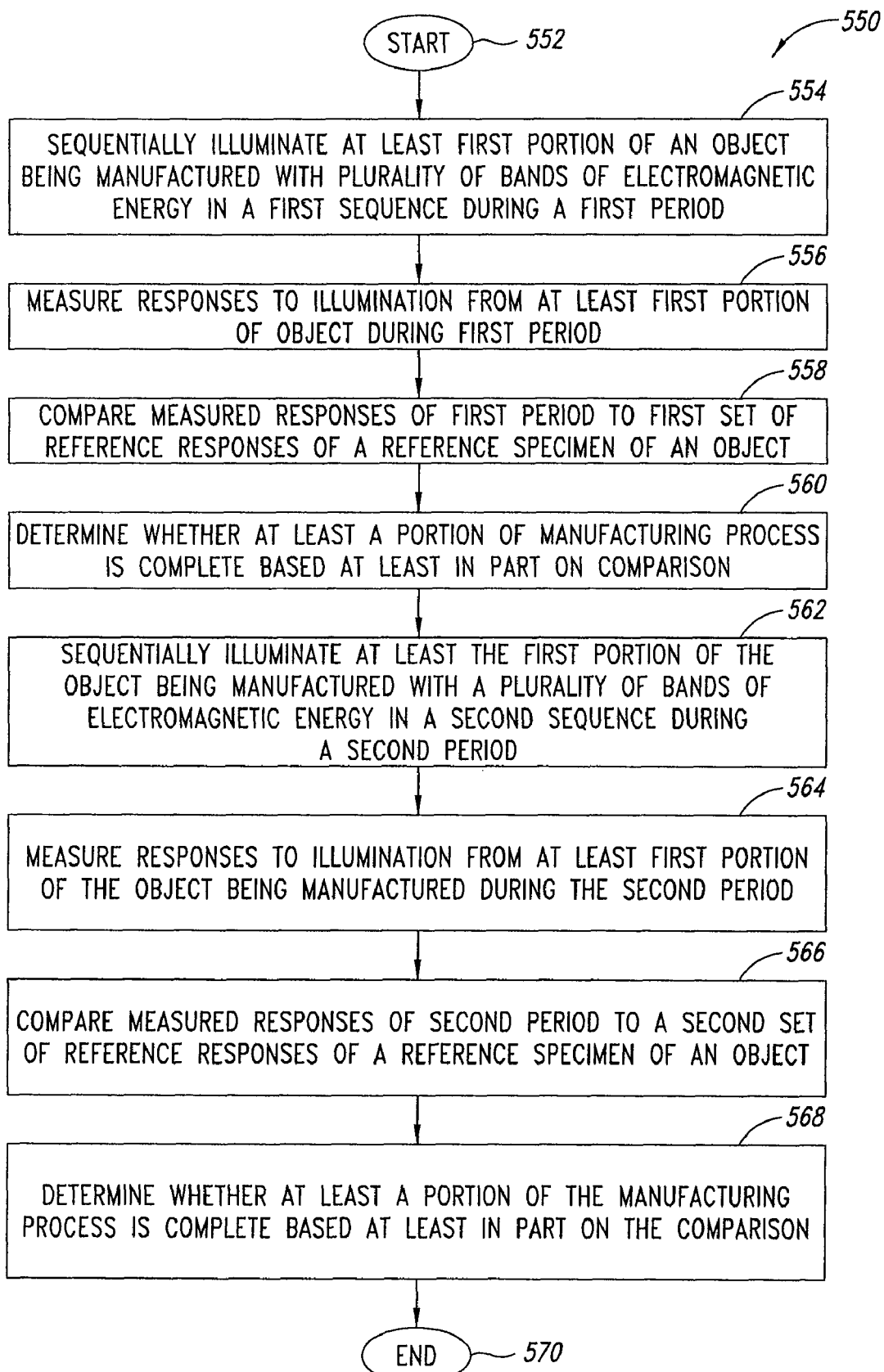
FIG. 12 is a flow diagram showing a method of operating a test device and/or a computing system of an evaluation system useful in controlling a manufacturing process, according to a further illustrated embodiment.

FIG. 12 shows a method 550 of operating the test device 14 and/or computing system 18, according to one illustrated embodiment. The method 550 may be useful in manufacturing of an object 50.

The method 550 starts at 552. For example, the method 550 may start in response to activation or powering of the test device 14 or computing system 18. Alternatively, the method 550 may start in response to a user input, receipt of data or instructions, or receipt of a signal from a sensor.

At 554, the test device 14 sequentially illuminates at least a first portion of an object 50 being manufactured with a plurality of bands of electromagnetic energy, in a first sequence during a first period. At 556, the sensor 46 measures responses to the illumination from at least a first portion of the object 50 during the first period. At 558, the test device 14 or computing system 18 compares the measured or test responses of the first period to a first set of reference responses of a reference specimen of an object 50. At 560, the test device 14 or computing system 18 determines whether at least a portion of the manufacturing process is complete based at least in part on the comparison.

At 562, the test device 14 sequentially illuminates at least the first portion of the object 50 being manufactured with a plurality of bands of electromagnetic energy, in a second sequence during a second period. At 564, the sensor 46 measures responses to the illumination from at least the first portion of the object 50 being manufactured, during the second period. At 566, the test device 14 or computing system 18 compares the measured or test responses of the second period to a second set of reference responses of a reference specimen of the object 50. At 568, the test device 14 or computing system 18 determines whether at least a portion of the manufacturing process is complete, based at least in part on the comparison. As noted above, varying the sequence may enhance security by implementing an inherent encryption process. Employing two or more sequences may produce more reliable results, particularly where the sequences employ different spectral emissions, or may produce different spectral results.

The method 550 terminates at 570. In some embodiments, the method 550 may return control back to 552, in lieu of terminating at 570. In other embodiments, the method 550 may operate as separate processes or threads, in parallel or concurrently with one another.

FIG. 13 shows a method 570 of operating the test device 14, according to one illustrated embodiment.

At 572, the test device 14 sequentially illuminates at least a portion of the object 50 being manufactured with electromagnetic energy from bands within a visible portion, an infrared portion, or an ultraviolet portion of the electromagnetic spectrum. Other embodiments may employ bands from other portions of the electromagnetic spectrum, for example, microwave or X-ray portions. In particular, the control subsystem 54 and/or microprocessor 56 may drive the sources 44 in an order, timing and/or drive level and/or temperature defined by the particular sequence.

FIG. 14 shows a method 576 of operating the test device 14, according to one illustrated embodiment.

At 578, the control subsystem 54 and/or microprocessor 56, selectively activates or turns on respective ones of a plurality of sources 46 in an order defined by the sequence.

FIG. 15 shows a method 580 of operating the test device 14, according to another illustrated embodiment.

At 582, the control subsystem 54 and/or microprocessor 56 selectively applies current to respective ones of the sources 44 in the order defined by the sequence.

FIG. 16 shows a method 586 of operating the test device 14, according to another illustrated embodiment.

At 588, the control subsystem 54 and/or microprocessor 56 selectively applies current at a plurality of different levels to respective ones of the sources 44, where the order and the drive level are defined by the sequence.

Figure 17:
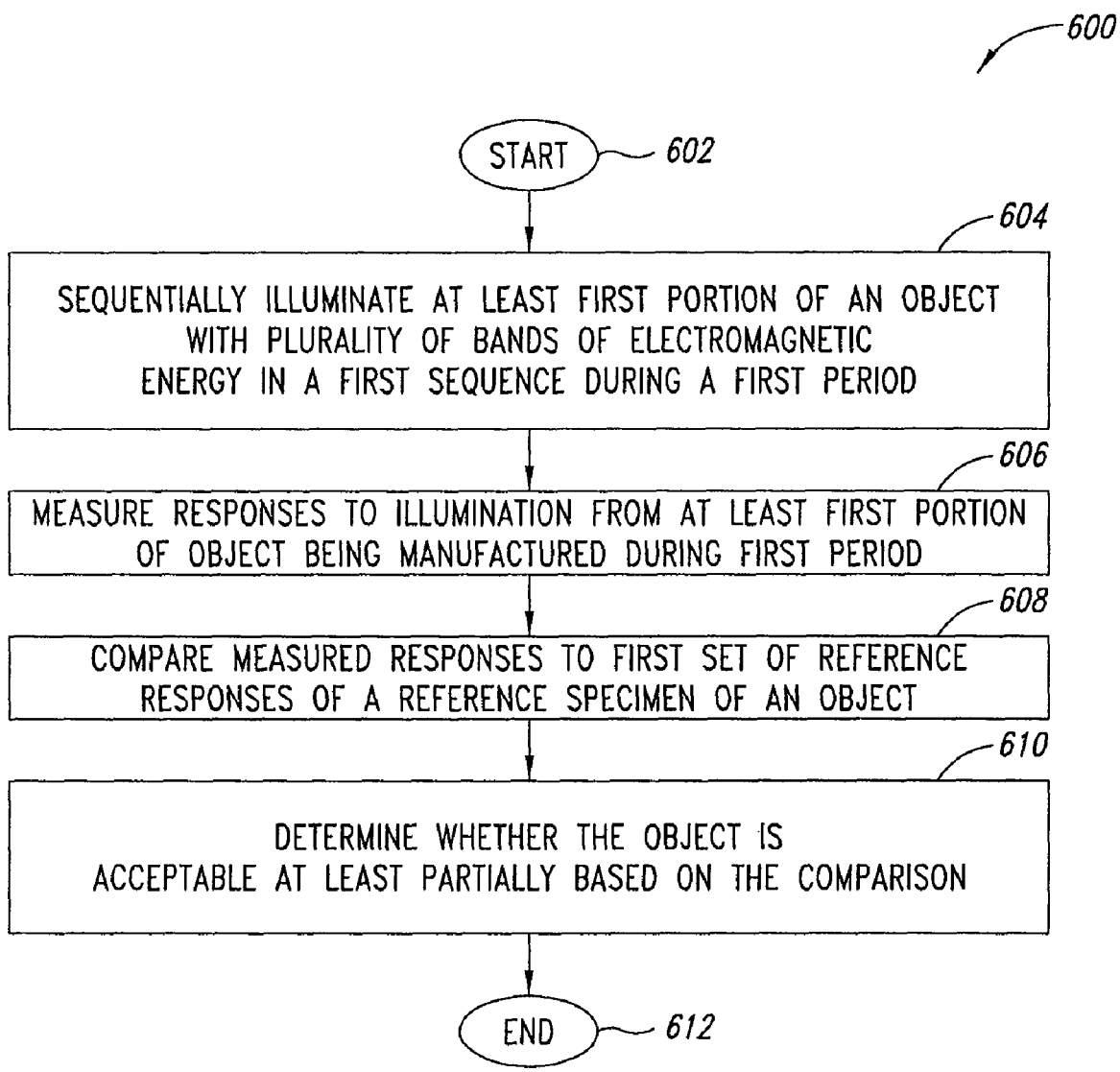
FIG. 17 is a flow diagram showing a method of operating a test device and/or a computing system of an evaluation system useful in implementing quality control with respect to manufactured objects, according to one illustrated embodiment.

FIG. 17 shows a method 600 of operating a test device 14 and/or a computing system 18, according to another illustrated embodiment. The method 600 may be useful in implementing quality control during or after a manufacturing process.

The method 600 starts at 602. For example, the method 600 may start in response to activation or powering of the test device 14 and/or computing system 18. Alternatively, the method 600 may start in response to a user input, receipt of data or instructions, or receipt of a signal from a sensor.

At 604, the test device 14 sequentially illuminates at least a first portion of an object 50 being manufactured with a plurality of bands of electromagnetic energy, in a first sequence during a first period. At 606, the sensor 46 (FIG. 4) of the test device 14 measures responses to the illumination from at least the first portion of the object 50 during the first period.

At 608, the test device 14 and/or computing system 18 compares the measured or test responses to a first set of reference responses of a reference specimen of an object 50. At 610, the test device 14 and/or computing system 18 determines whether the object 50 being manufactured is acceptable at least partially based on the comparison.

The method 600 terminates at 612. In some embodiments, the method 600 may return control back to 602, in lieu of terminating at 612. In other embodiments, the method 600 may operate as separate processes or threads, in parallel or concurrently with one another.

Figure 18:
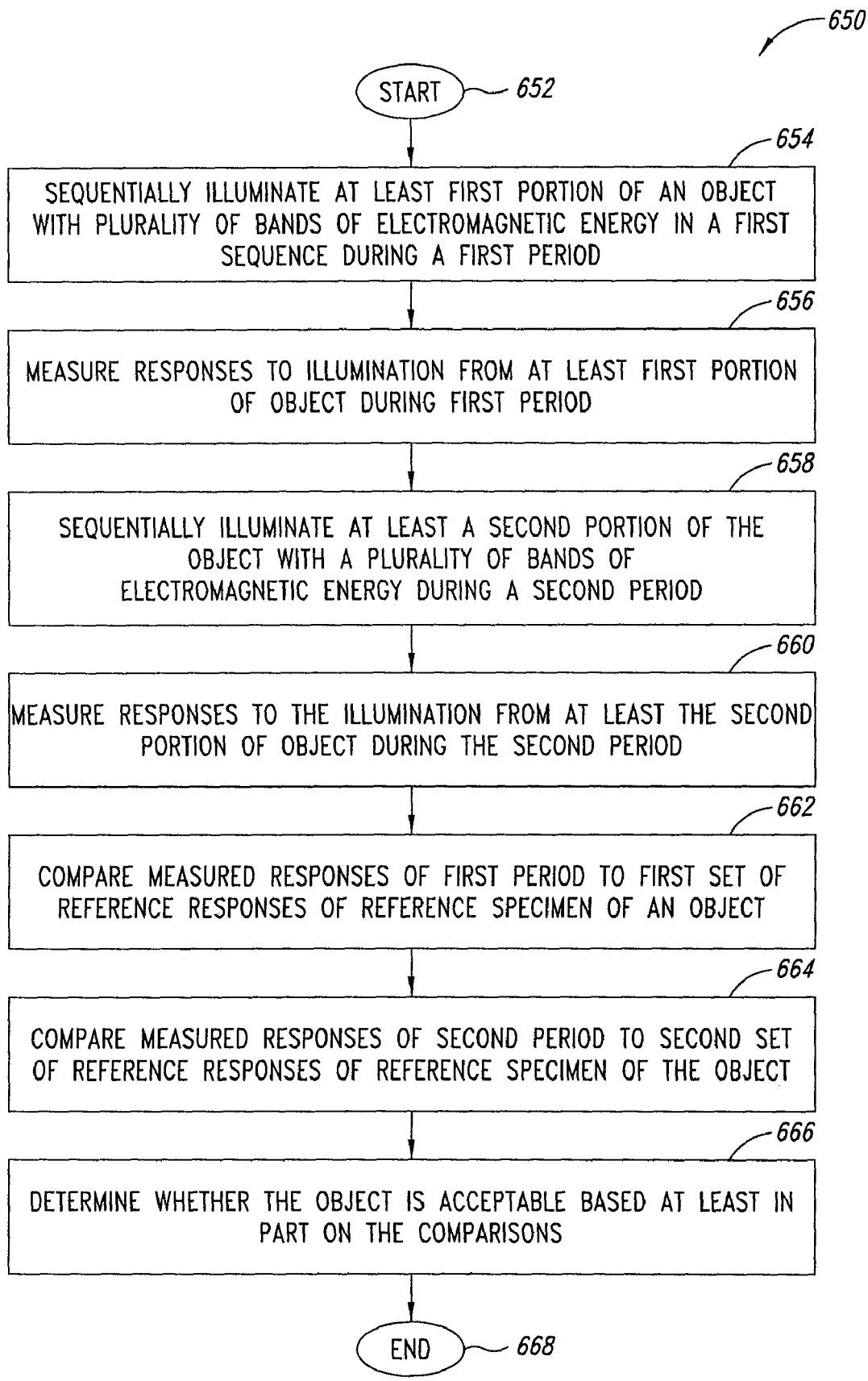
FIG. 18 is a flow diagram showing a method of operating a test device and/or a computing system of an evaluation system useful in implementing quality control with respect to manufactured objects, according to another illustrated embodiment.

FIG. 18 shows a method 650 of operating a test device 14 and/or computing system 18, according to another illustrated embodiment. The method 650 may be useful in implementing quality control during or after a manufacturing process.

The method 650 starts at 652. For example, the method 650 may start in response to activation or powering of the test device 14 and/or computing system 18. Alternatively, the method 650 may start in response to a user input, receipt of data or instructions, or receipt of a signal from a sensor.

At 654, the test device 14 sequentially illuminates at least a first portion of an object 50 being manufactured with a plurality of bands of electromagnetic energy, in a first sequence during a first period. At 656, the sensor 46 of the test device 14 measures responses to the illumination from at least a first portion of the object 50 being manufactured during the first period. At 658, the test device 14 sequentially illuminates at least a second portion of the object 50 being manufactured, with a plurality of bands of electromagnetic energy during a second period. At 660, the sensor 46 of the test device 14 measures responses to the illumination from at least the second portion of the object 50 being manufactured, during the second period.

At 662, the test device 14 and/or computing system 18 compares the measured or test responses of the first period to a first set of reference responses of a reference specimen of an object 50. At 664, the test device 14 and/or computing system 18 compares measured or test responses of the second period to a second set of reference responses of the reference specimen of the object 50. At 666, the test device 14 and/or computing system 18 determines whether at least a portion of the manufacturing process is complete based at least in part on the comparisons.

The method 650 terminates at 668. In some embodiments, the method 650 may return control back to 652, in lieu of terminating at 668. In other embodiments, the method 650 may operate as separate processes or threads, in parallel or concurrently with one another.

Figure 19:
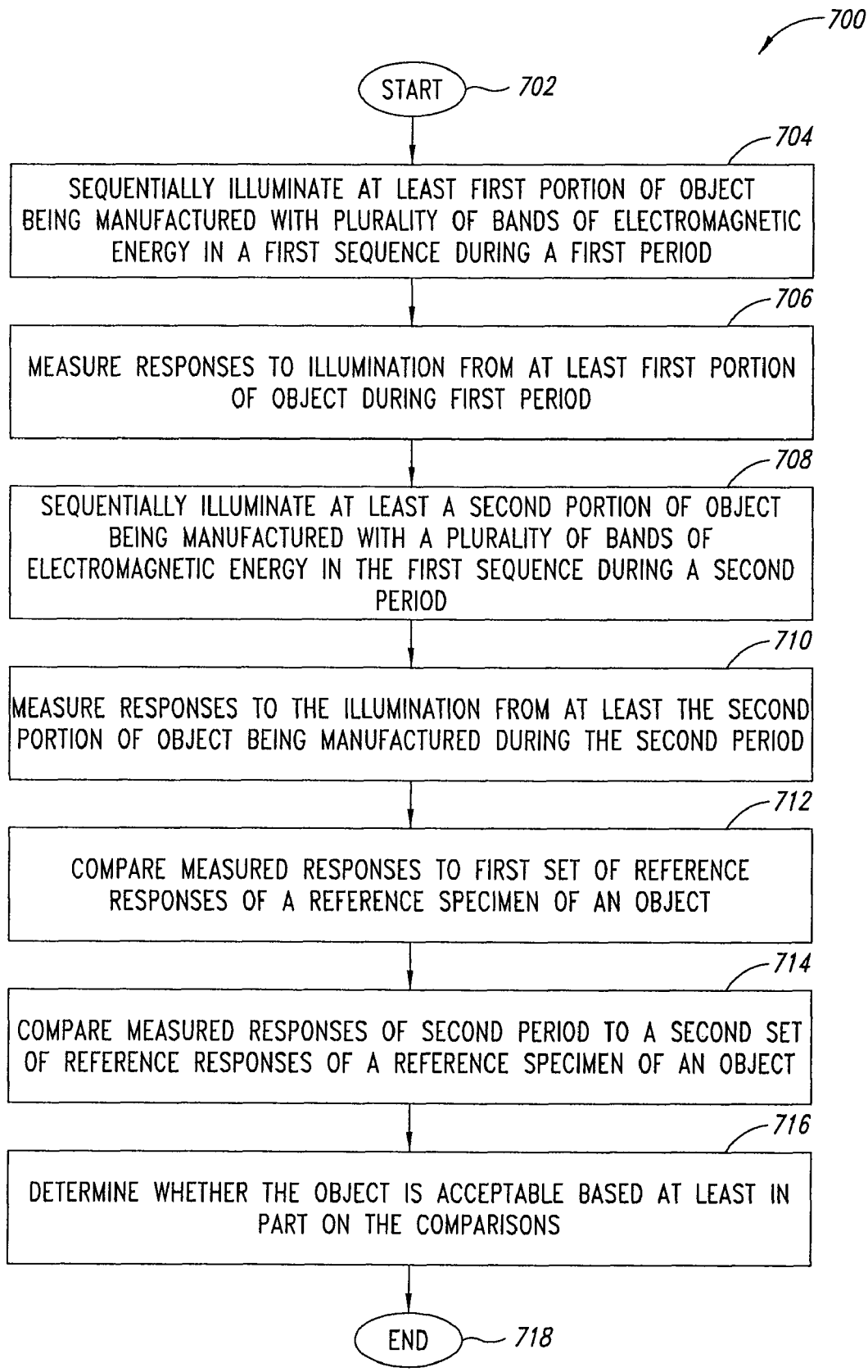
FIG. 19 is a flow diagram showing a method of operating a test device and/or a computing system of an evaluation system useful in implementing quality control with respect to manufactured objects, according to yet another illustrated embodiment.

FIG. 19 shows a method 700 of operating a test device 14 and/or a computing system 18, according to a further illustrated embodiment. The method 700 may be useful in implementing quality control during or after a manufacturing process.

The method 700 starts at 702. For example, the method 700 may start in response to activation or powering of the test device 14 and/or computing system 18. Alternatively, the method 700 may start in response to a user input, receipt of data or instructions, or receipt of a signal from a sensor.

At 704, the test device 14 sequentially illuminates at least a first portion of an object 50 being manufactured with a plurality of bands of electromagnetic energy, in a first sequence during a first period. At 706, the sensor 46 (FIG. 4) of the test device 14 measures responses to the illumination from at least a first portion of the object 50 during the first period. At 708, the test device 14 sequentially illuminates at least a second portion of the object 50 being manufactured with a plurality of bands of electromagnetic energy, in the first sequence during a second period. At 710, the sensor 46 of the test device 14 measures a response to the illumination from at least the second portion of the object 50 being manufactured, during the second period.

At 712, the test device 14 and/or computing system 18 compares the measured or test responses of the first period to a first set of reference responses of a reference specimen of an object 50. At 714, the test device 14 and/or computing system 18 compares the measured or test responses of the second period to a second set of reference responses of the reference specimen of the object 50. At 716, the test device 14 or computing system 18 determines whether at least a portion of the manufacturing process is complete, based at least in part on the comparisons.

The method 700 terminates at 718. In some embodiments, the method 700 may return control back to 702, in lieu of terminating at 718. In other embodiments, the method 700 may operate as separate processes or threads, in parallel or concurrently with one another.

Figure 20:
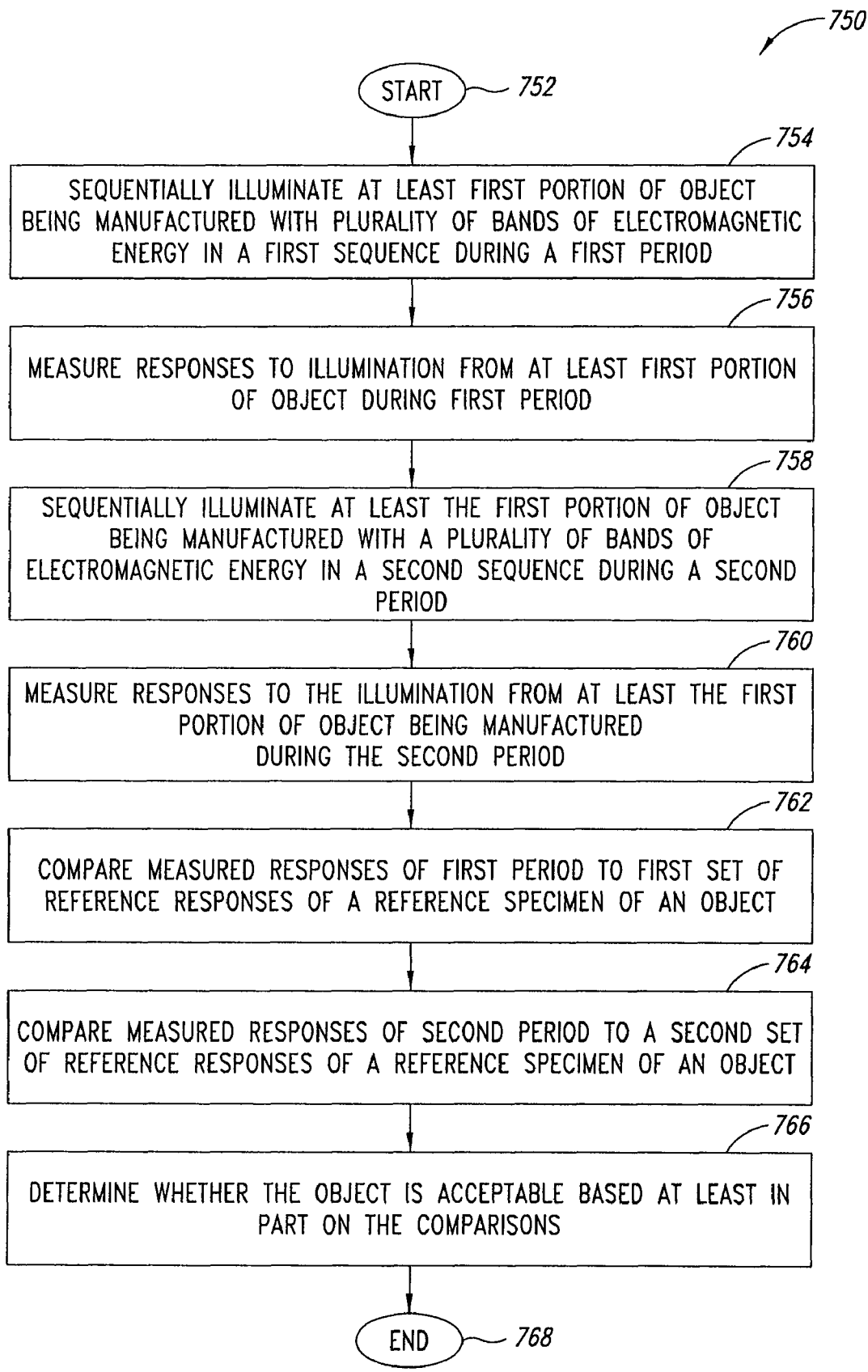
FIG. 20 is a flow diagram showing a method of operating a test device and/or a computing system of an evaluation system useful in implementing quality control with respect to manufactured objects, according to still another illustrated embodiment.

FIG. 20 shows a method 750 of operating a test device 14 and/or a computing system 18, according to still another embodiment. The method 750 may be useful in implementing quality control during or after a manufacturing process.

The method 750 starts at 752. For example, the method 750 may start in response to activation or powering of the test device 14 and/or computing system 18. Alternatively, the method 750 may start in response to a user input, receipt of data or instructions, or receipt of a signal from a sensor.

At 754, the test device 14 sequentially illuminates at least a first portion of an object 50 being manufactured with a plurality of bands of electromagnetic energy, in a first sequence during a first period. At 756, the sensor 46 (FIG. 4) of the test device 14 measures responses to the illumination from at least the first portion of the object 50 during the first period. At 758, the test device 14 sequentially illuminates at least the first portion of the object 50 being manufactured with a plurality of bands of electromagnetic energy, in a second sequence during a second period. At 760, the sensor 46 of the test device 14 measures responses to the illumination from at least the first portion of the object 50 being manufactured, during the second period.

At 762, the test device 14 and/or computing system 18 compares the measured or test responses of the first period to a first set of reference responses of a reference specimen of an object. At 764, the test device 14 and/or computing system 18 compares measured or test responses of the second period to a second set of reference responses of the reference specimen of the object 50. At 766, the test device 14 and/or computing system 18 determines whether at least a portion of the manufacturing process is complete, based at least in part on the comparisons.

The method 750 terminates at 768. In some embodiments, the method 750 may return control back to 752, in lieu of terminating at 768. In other embodiments, the method 750 may operate as separate processes or threads, in parallel or concurrently with one another.

Figure 21:
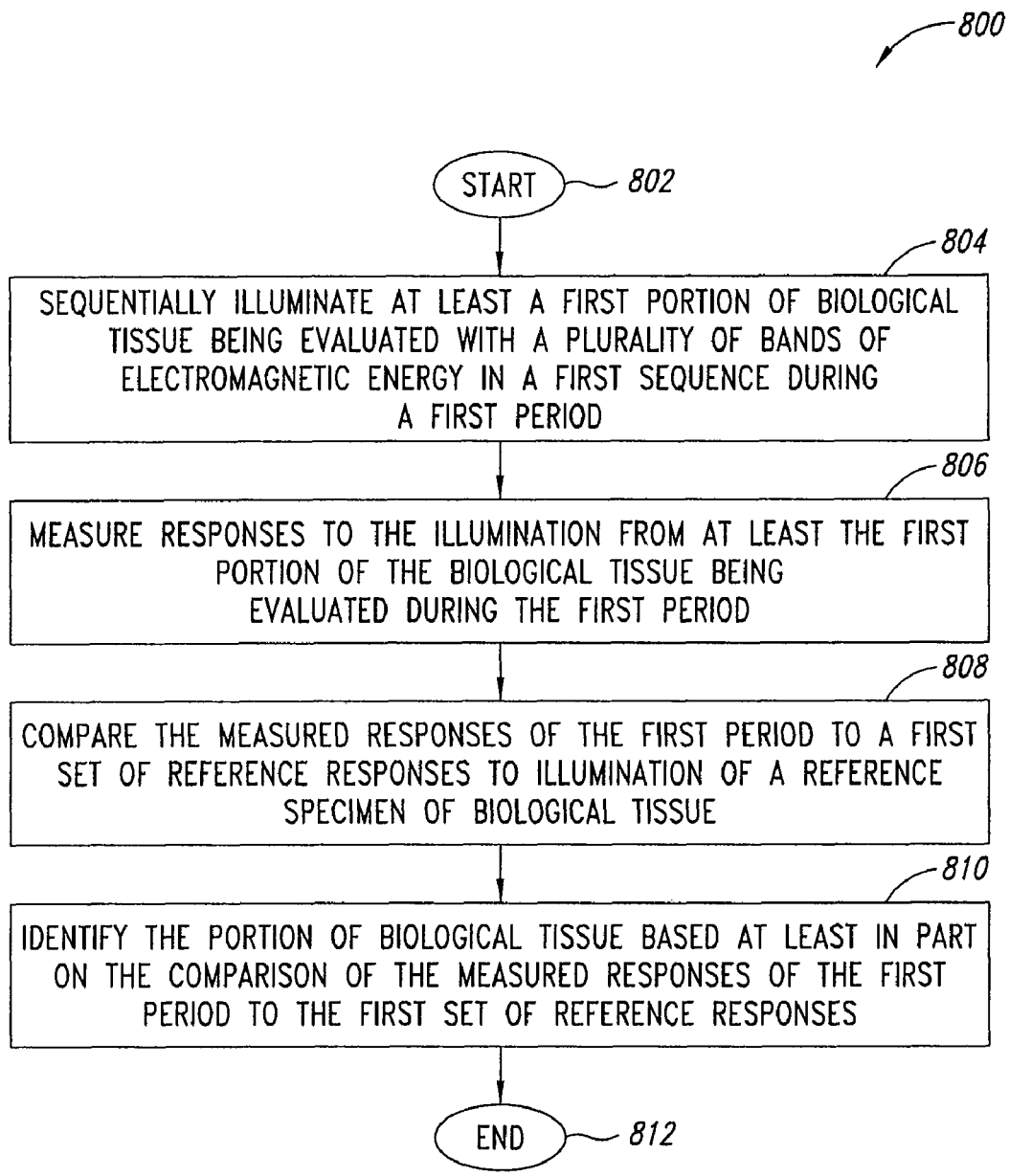
FIG. 21 is a flow diagram showing a method of operating a test device and/or a computing system of an evaluation system useful in identifying biological tissue, according to one illustrated embodiment.

FIG. 21 shows a method 800 of operating a test device 14 and/or a computing system 18, according to one illustrated embodiment. The method 800 may be useful in identifying biological tissue (e.g. retinal tissue, blood, skin, hair, bone, organs, bodily fluids, etc.).

The method 800 starts at 802. For example, the method 800 may start in response to activation or powering of the test device 14 and/or computing system 18. Alternatively, the method 800 may start in response to a user input, receipt of data or instructions, or receipt of a signal from a sensor.

At 804, the test device 14 sequentially illuminates at least a first portion of biological tissue being evaluated with a plurality of bands of electromagnetic energy, in a first sequence during a first period. At 806, the sensor 46 (FIG. 4) of the test device 14 measures responses to the illumination from at least the first portion of the biological tissue being evaluated during the first period.

At 808, the test device 14 and/or computing system 18 compares the measured or test responses of the first period to a first set of reference responses to illumination of a reference specimen of the biological tissue. At 810, the test device 14 and/or computing system 18 identifies the portion of the biological tissue based at least in part on the comparison. For example, the test device 14 or computing system 18 may identify the reference sample based on a match to one or more known reference samples. The identification may be a unique identification or almost unique identification, similar or greater in confidence or probability to that associated with conventional fingerprinting or DNA techniques. For example, identifying a unique individual from which the biological tissue being evaluated derived. Alternatively, the identification may be non-unique identification, providing a group or subset of possible identities for the biological tissue being evaluated. For example, identifying a group or subset of individuals from which the biological tissue being evaluated derived.

The method 800 terminates at 812. In some embodiments, the method 800 may return control back to 802, in lieu of terminating at 812. In other embodiments, the method 800 may operate as separate processes or threads, in parallel or concurrently with one another.

Figure 22:
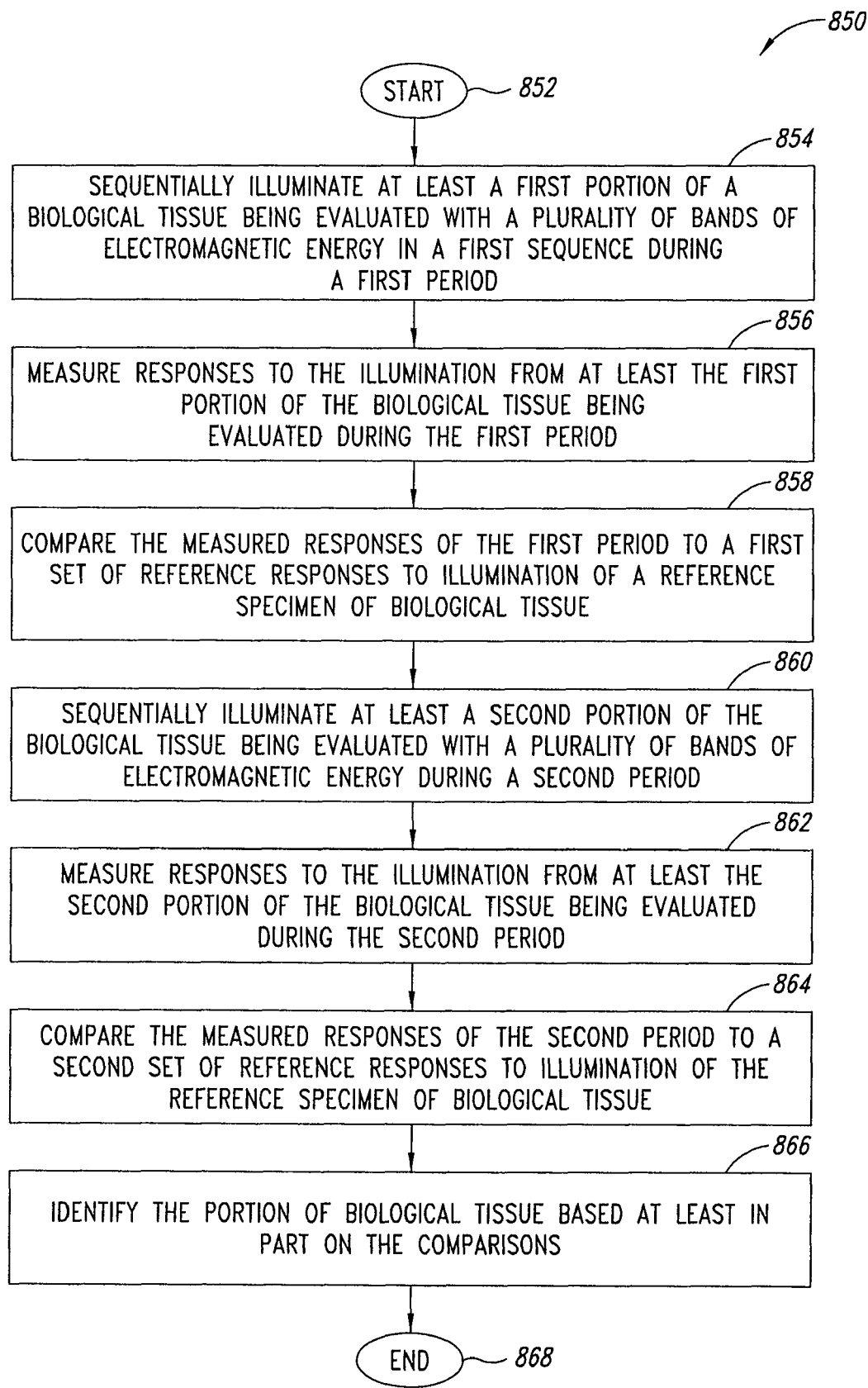
FIG. 22 is a flow diagram showing a method of operating a test device and/or a computing system of an evaluation system useful in identifying biological tissue, according to another illustrated embodiment.

FIG. 22 shows a method 850 of operating a test device 14 and/or a computing system 18, according to a further illustrated embodiment. The method 850 may be useful in identifying biological tissue.

The method 850 starts at 852. For example, the method 850 may start in response to activation or powering of the test device 14 and/or computing system 18. Alternatively, the method 850 may start in response to a user input, receipt of data or instructions, or receipt of a signal from a sensor.

At 854, the test device 14 sequentially illuminates at least a first portion of biological tissue being evaluated with a plurality of bands of electromagnetic energy, in a first sequence during a first period. At 856, the sensor 46 (FIG. 4) of the test device 14 measures responses to the illumination from at least the first portion of the biological tissue being evaluated, during the first period.

At 858, the test device 14 and/or computing system 18 compares the measured or test responses of the first period to a first set of reference responses to illumination of a reference specimen of the biological tissue.

At 860, the test device 14 sequentially illuminates at least the second portion of the biological tissue being evaluated with a plurality of bands of electromagnetic energy, during a second period. At 862, the sensor 46 of the test device 14 measures responses to the illumination from at least the second portion of the biological tissue being evaluated, during the second period.

At 864, the test device 14 and/or computing system 18 compares the measured or test responses of the second period to a second set of reference responses to illumination of the reference specimen of the biological tissue. At 866, the test device 14 and/or computing system 18 identifies the portion of the biological tissue based at least in part on the comparisons. As noted previously, employing samples from two or more portions may increase accuracy of the analysis.

The method 850 terminates at 868. In some embodiments, the method 850 may return control back to 852, in lieu of terminating at 868. In other embodiments, the method 850 may operate as separate processes or threads, in parallel or concurrently with one another.

Figure 23:
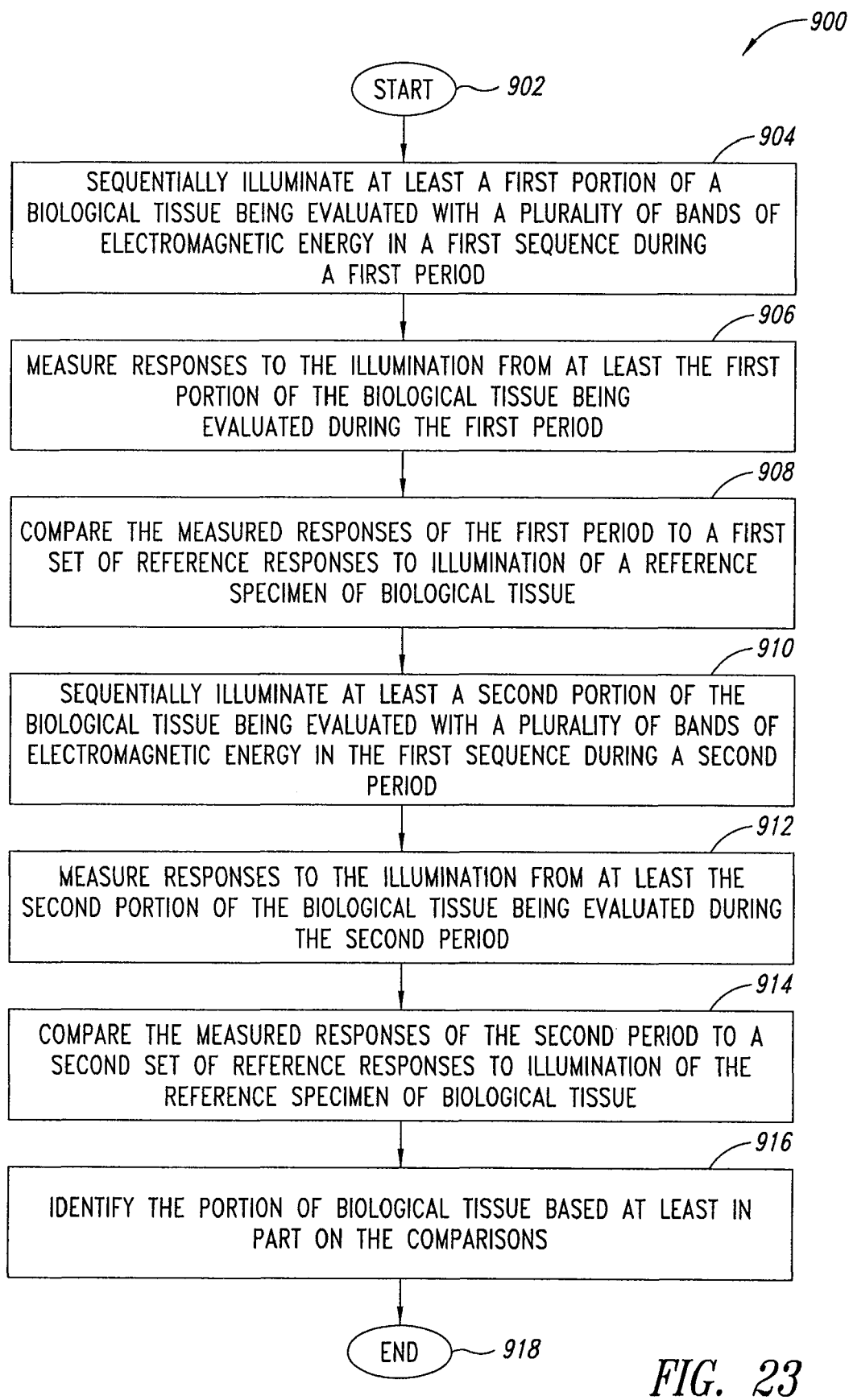
FIG. 23 is a flow diagram showing a method of operating a test device and/or a computing system of an evaluation system useful in identifying biological tissue, according to yet another illustrated embodiment.

FIG. 23 shows a method 900 of operating a test device 14 and/or a computing system 18, according to a yet another illustrated embodiment. The method 900 may be useful in identifying biological tissue.

The method 900 starts at 902. For example, the method 900 may start in response to activation or powering of the test device 14 and/or computing system 18. Alternatively, the method 900 may start in response to a user input, receipt of data or instructions, or receipt of a signal from a sensor.

At 904, the test device 14 sequentially illuminates at least a first portion of biological tissue being evaluated with a plurality of bands of electromagnetic energy, in a first sequence during a first period. At 906, the sensor 46 (FIG. 4) of the test device 14 measures responses to the illumination from at least the first portion of the biological tissue being evaluated during the first period.

At 908, the test device 14 and/or computing system 18 compares the measured or test responses of the first period to a first set of reference responses to illumination of a reference specimen of a biological tissue.

At 910, the test device 14 sequentially illuminates at least a second portion of the biological tissue being evaluated with a plurality of bands of electromagnetic energy, in the first sequence during a second period. At 912, the sensor 46 of the test device 14 measures responses to the illumination from at least the second portion of the biological tissue being evaluated during the second period.

At 914, the test device 14 and/or computing system 18 compares the measured or test responses of the second period to a second set of reference responses to illumination of the reference specimen of the biological tissue. At 916, the test device 14 and/or computing system 18 identifies the portion of biological tissue based at least in part on the comparisons.

The method 900 terminates at 918. In some embodiments, the method 900 may return control back to 902, in lieu of terminating at 918. In other embodiments, the method 900 may operate as separate processes or threads, in parallel or concurrently with one another.

Figure 24:
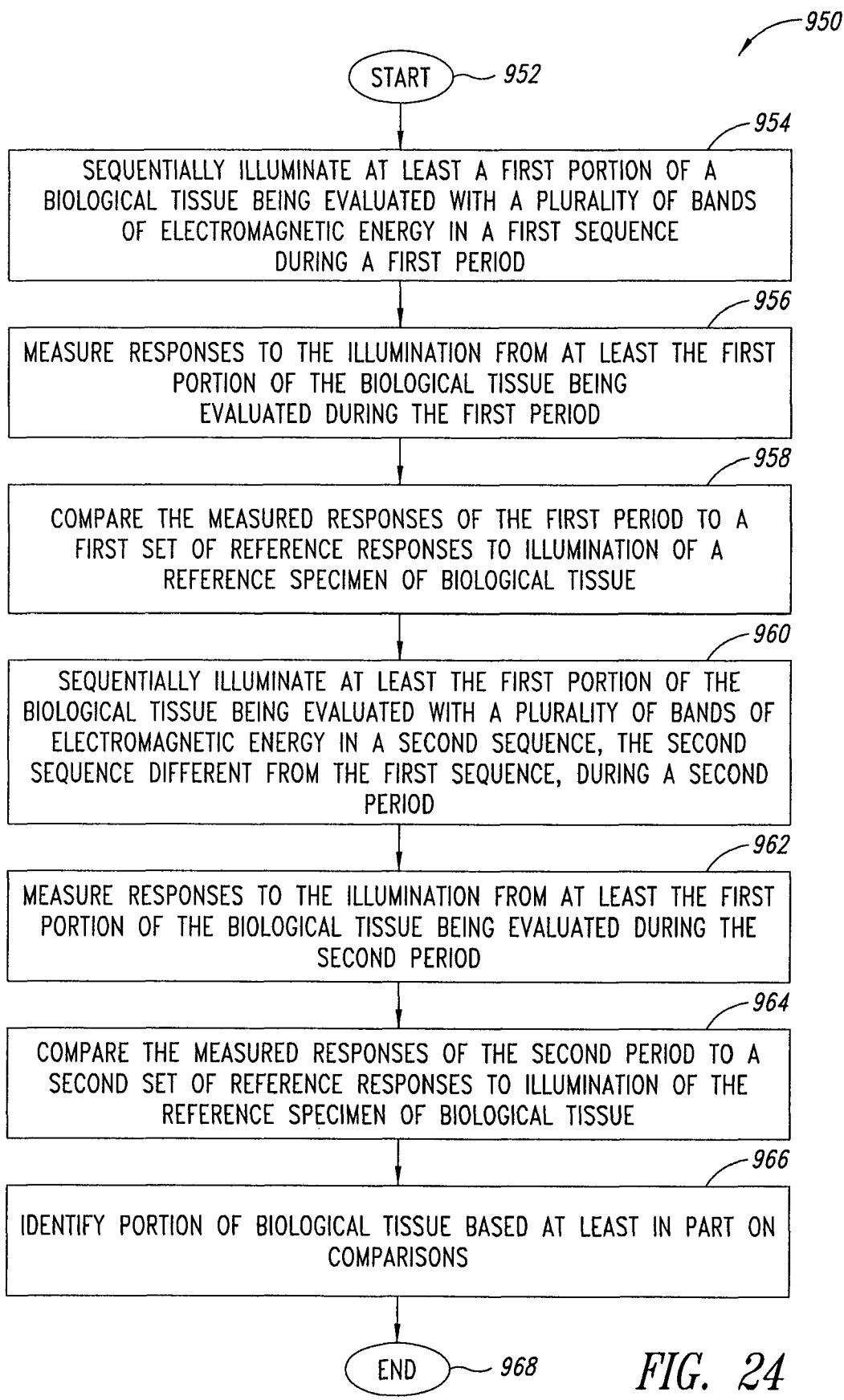
FIG. 24 is a flow diagram showing a method of operating a test device and/or a computing system of an evaluation system useful in identifying biological tissue, according to still another illustrated embodiment.

FIG. 24 shows a method 950 of operating a test device 14 and/or a computing system 18, according to still another illustrated embodiment. The method 950 may be useful in identifying biological tissue.

The method 950 starts at 952. For example, the method 950 may start in response to activation or powering of the test device 14 and/or computing system 18. Alternatively, the method 950 may start in response to a user input, receipt of data or instructions, or receipt of a signal from a sensor.

At 954, the test device 14 sequentially illuminates at least a first portion of a biological tissue being evaluated with a plurality of bands of electromagnetic energy, in a first sequence during a first period. At 956, the sensor 46 (FIG. 4) of the test device 14 measures responses to the illumination from at least the first portion of the biological tissue being evaluated during the first period.

At 958, the test device 14 and/or computing system 18 compares the measured or test responses of the first period to a first set of reference responses to illumination of a reference specimen of the biological tissue.

At 960, the test device 14 sequentially illuminates at least the first portion of the biological tissue being evaluated with a plurality of bands of electromagnetic energy in a second sequence, during a second period, the second sequence different from the first sequence. At 962, the sensor 46 of the test device 14 measures responses to the illumination from at least the first portion of the biological tissue being evaluated during the second period.

At 964, the test device 14 and/or computing system 18 compares the measured or test responses of the second period to a second set of reference responses to illumination of the reference specimen of the biological tissue. At 966, the test device 14 and/or computing system 18 identifies the portion of biological tissue, based at least in part on the comparisons.

The method 950 terminates at 968. In some embodiments, the method 950 may return control back to 952, in lieu of terminating at 968. In other embodiments, the method 950 may operate as separate processes or threads, in parallel or concurrently with one another.

FIG. 25 shows a method 1000 of operating the test device 14, according to one illustrated embodiment.

At 1002, the control subsystem 54 and/or microprocessor 56 (FIG. 4) of the test device 14 sequentially illuminates at least the first portion of the biological tissue being evaluated with electromagnetic energy from bands within a visible portion, an infrared portion, or an ultraviolet portion of the electromagnetic spectrum. Other embodiments may employ bands from other portions of the electromagnetic spectrum, for example, microwave or X-ray portions.

FIG. 26 shows a method 1006 of operating the test device 14 according to another illustrated embodiment.

At 1008, the control subsystem 54 and/or microprocessor 56 (FIG. 4) of the test device 14 selectively turns respective ones of a plurality of sources 44 On and Off, in an order defined by the sequence to illuminate the biological tissue.

FIG. 27 shows a method 1012 of operating the test device 14, according to yet another illustrated embodiment.

At 1014, the control subsystem 54 and/or microprocessor 56 (FIG. 4) of the test device 14 selectively applies current to respective ones of the sources 44 in the order defined by the sequence to illuminate the biological tissue.

FIG. 28 shows a method 1018 of operating the test device 14, according to still another illustrated embodiment.

At 1020, the control subsystem 54 and/or microprocessor 56 (FIG. 4) of the test device 14 selectively applies current at a plurality of different drive levels to respective ones of the sources 44, where the order and the drive level are defined by the sequence, to illuminate the biological tissue.

FIG. 29 shows a method 1024 of operating the test device 14 and/or computing system 18, according to a further illustrated embodiment. The method may be used with any of the methods of FIGS. 21-24.

At 1026, the test device 14 and/or computing system 18 classifies the portion of biological tissue. The test device 14 and/or computing system 18 may classify the biological tissue by finding matches to reference responses of reference specimens of reference biological tissue. For example, the test device 14 and/or computing system 18 may find a match with a spectral response from a normal reference specimen or may find a match with a spectral response of one or more abnormal specimens. For example, the test device 14 and/or computing system 18 may find a match with a spectral response from a reference specimen that represents one or more known physical characteristics, such a species, gender, blood type, organ, etc.

Figure 30:
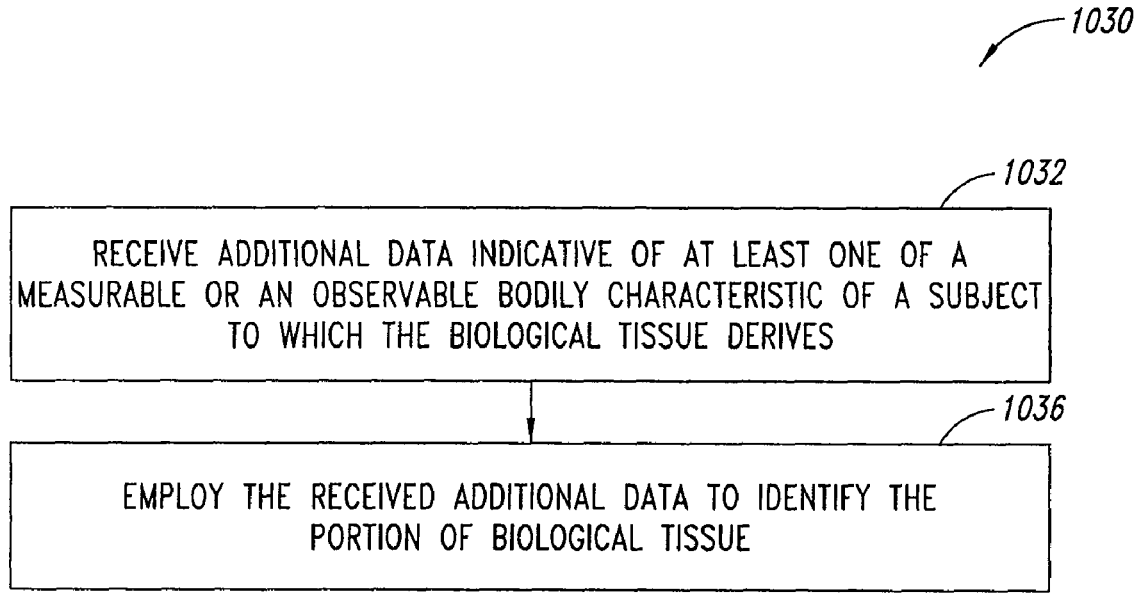
FIG. 30 is a flow diagram showing a method of operating a test device and/or computing system of an evaluation system with additional data that may be useful with at least some of the previous methods, according to one illustrated embodiment.

FIG. 30 shows a method 1030 of operating the test device 14 and/or computing system 18, according to a further illustrated embodiment. The method 1030 may be used with any of the methods of FIGS. 1-24.

At 1032, the test device 14 and/or computing system 18 receives additional data indicative of at least one of a measurable or an observable bodily characteristic of a subject to which the biological tissue derives. At 1036, the test device 14 and/or computing system 18 employs the received additional data to identify the portion of biological tissue. For example, the test device 14 or computing system 18 may employ the additional data to increase a confidence level in a match, or to find a closest match. Also for example, the test device 14 or computing system 18 may alternatively, or additionally employ the additional data to or to reduce the number of reference samples to which the measured or test response will be compared. This may advantageously reduce processing time and use of computational resources.

Figure 31:
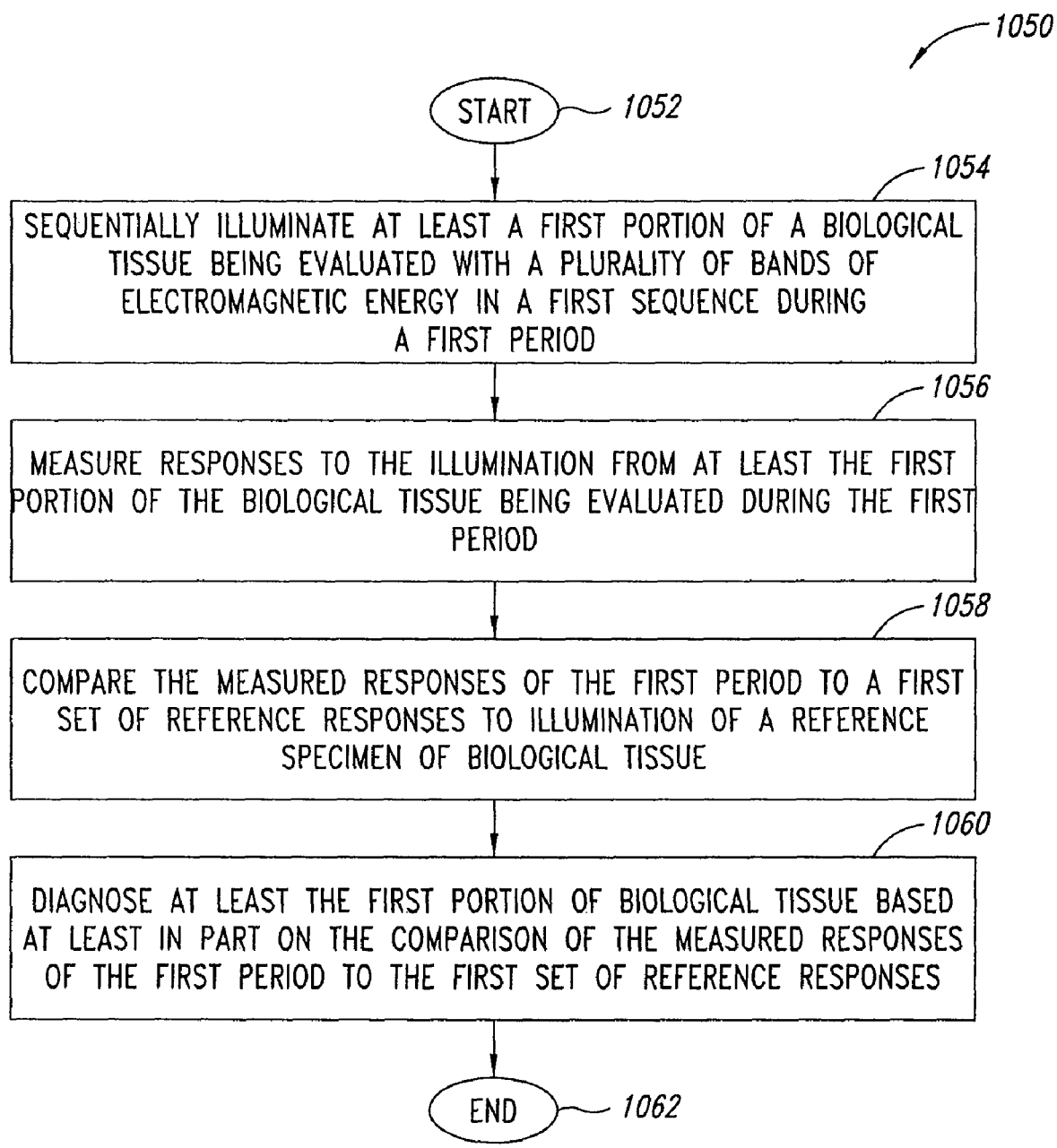
FIG. 31 is a flow diagram showing a method of operating a test device and/or computing system of an evaluation system to perform or facilitate diagnosis based on biological tissue, according to one illustrated embodiment.

FIG. 31 shows a method 1050 of operating the test device 14 and/or computing system 18, according to one illustrated embodiment. The method 1050 may be useful in diagnosing based on a biological tissue sample or specimen.

The method 1050 starts at 1052. For example, the method 1050 may start in response to activation or powering of the test device 14 and/or computing system 18. Alternatively, the method 1050 may start in response to a user input, receipt of data or instructions, or receipt of a signal from a sensor.

At 1054, the test device 14 sequentially illuminates at least a first portion of biological tissue being evaluated with a plurality of bands of electromagnetic energy, in a first sequence during a first period. At 1056, the sensor 46 of the test device 14 measures responses to the illumination from at least the first portion of the biological tissue being evaluated, during the first period.

At 1058, the test device 14 and/or computing system 18 compares the measured or test responses of the first period to a first set of reference responses to illumination of a reference specimen of the biological tissue.

At 1060, the test device 14 and/or computing system 18 diagnoses at least the first portion of biological tissue based at least in part on the comparison of the measured responses to the set of reference responses. For example, the test device 14 and/or computing system 18 may find a match with a spectral response from one or more abnormal specimens which represent or are otherwise associated with known or unknown conditions, diseases, or pathologies. For example, a spectral response of a biopsy may be compared with spectral responses of various abnormal tissues, for example various tumors, carcinomas or malignancies. Also for example, a spectral response of a biopsy may be compared with spectral responses of various abnormal tissues, for example various diseased organs, such as livers. For example, a spectral response of a bodily fluid may be compared with spectral responses of bodily fluids having known characteristics. For instance, a spectral response of blood from a subject may be compared with spectral responses of reference blood samples with known characteristics (e.g., blood sugar levels). Such may allow the monitoring of blood sugar, useful in a variety of circumstances, for instance in monitoring diabetics. In some embodiments, the monitoring may be non-invasive, for example illuminating the blood through the skin. Such may advantageously reduce or eliminate discomfort, thereby increasing compliance with monitoring regimes. Such may also advantageously reduce the risk of infection. Such non-invasive monitoring may employ wavelengths of electromagnetic energy that penetrate at least some layers of skin. Such testing may advantageously be in vivo, allowing real time results from actual subjects. Such may advantageously eliminate the need for additional equipment (e.g., sample or specimen holders, needles, etc.) which may require sterilization and/or special disposal procedures.

The method 1050 terminates at 1062. In some embodiments, the method 1050 may return control back to 1052, in lieu of terminating at 1062. In other embodiments, the method 1050 may operate as separate processes or threads, in parallel or concurrently with one another.

Figure 32:
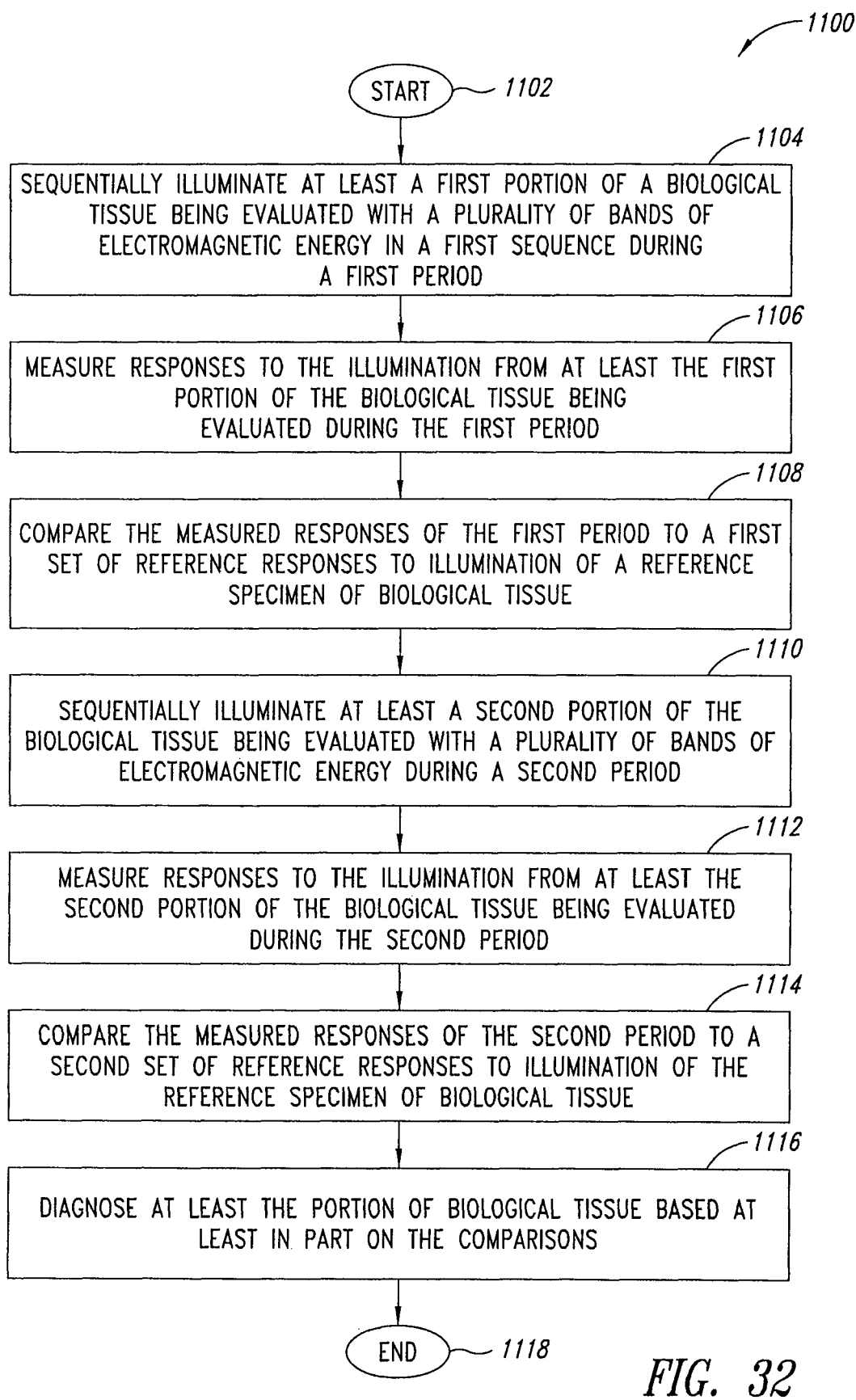
FIG. 32 is a flow diagram showing a method of operating a test device and/or computing system of an evaluation system to perform or facilitate diagnosis based on biological tissue, according to another illustrated embodiment.

FIG. 32 shows a method 1100 of operating a test device 14 and/or computing system 18, according to another illustrated embodiment. The method 1100 may be useful in diagnosing based on a biological tissue sample or specimen.

The method 1100 starts at 1102. For example, the method 1100 may start in response to activation or powering of the test device 14 and/or computing system 18. Alternatively, the method 1100 may start in response to a user input, receipt of data or instructions, or receipt of a signal from a sensor.

At 1104, the test device 14 sequentially illuminates at least a first portion of a biological tissue being evaluated with a plurality of bands of electromagnetic energy, in a first sequence during a first period. At 1106, the sensor 46 (FIG. 4) of the test device 14 measures responses to the illumination from at least the first portion of the biological tissue being evaluated during the first period.

At 1108, the test device 14 and/or computing system 18 compares the measured or test responses of the first period to a first set of reference responses to illumination of a reference specimen of the biological tissue.

At 1110, the test device 14 sequentially illuminates at least the second portion of the biological tissue being evaluated with a plurality of bands of electromagnetic energy, during a second period. At 1112, the sensor 46 of the test device 14 measures responses to the illumination from at least the second portion of the biological tissue being evaluated, during the second period.

At 1114, the test device 14 and/or computing system 18 compares the measured or test responses of the second period to a second set of reference responses to illumination of the reference specimen of the biological tissue. At 1116, the test device 14 and/or computing system 18 diagnoses the portion of the biological tissue, based at least in part on the comparisons.

The method 1100 terminates at 1118. In some embodiments, the method 1100 may return control back to 1102, in lieu of terminating at 1118. In other embodiments, the method 1100 may operate as separate processes or threads, in parallel or concurrently with one another.

Figure 33:
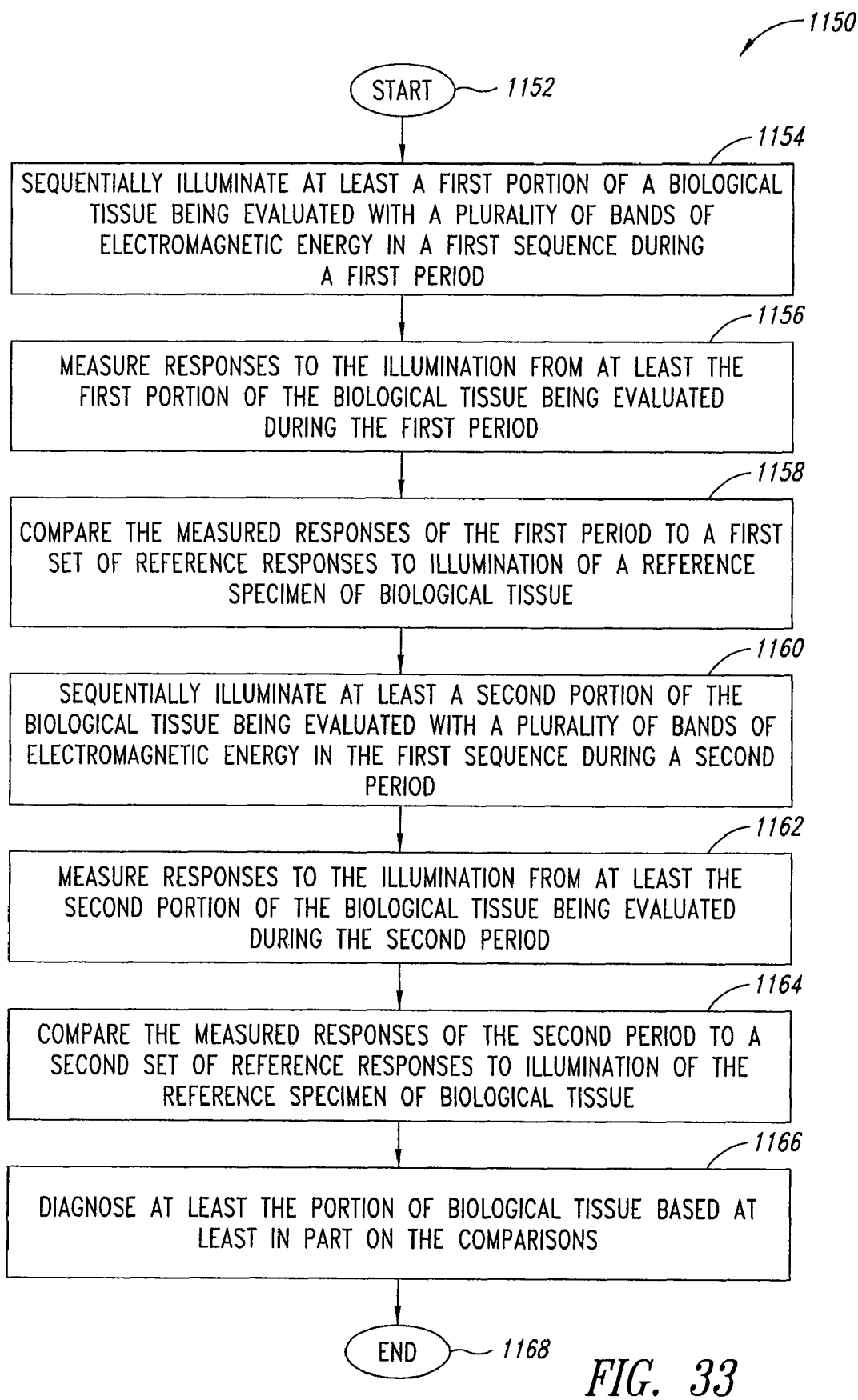
FIG. 33 is a flow diagram showing a method of operating a test device and/or computing system of an evaluation system to perform or facilitate diagnosis based on biological tissue, according to yet another illustrated embodiment.

FIG. 33 shows a method 1150 of operating a test device 14 and/or a computing system 18, according to a yet another illustrated embodiment. The method 1150 may be useful in diagnosing based on a biological tissue specimen or sample.

The method 1150 starts at 1152. For example, the method 1150 may start in response to activation or powering of the test device 14 and/or computing system 18. Alternatively, the method 1150 may start in response to a user input, receipt of data or instructions, or receipt of a signal from a sensor.

At 1154, the test device 14 sequentially illuminates at least a first portion of a biological tissue being evaluated with a plurality of bands of electromagnetic energy, in a first sequence during a first period. At 1156, the sensor 46 (FIG. 4) of the test device 14 measures responses to the illumination from at least the first portion of the biological tissue being evaluated, during the first period.

At 1158, the test device 14 and/or computing system 18 compares the measured or test responses of the first period to a first set of reference responses to illumination of a reference specimen of the biological tissue.

At 1160, the test device 14 sequentially illuminates at least the second portion of the biological tissue being evaluated with a plurality of bands of electromagnetic energy, in the first sequence during a second period. At 1162, the sensor 46 of the test device 14 measures responses to the illumination from at least the second portion of the biological tissue being evaluated, during the second period.

At 1164, the test device 14 and/or computing system 18 compares the measured or test responses of the second period to a second set of reference responses to illumination of the reference specimen of the biological tissue. At 1166, the test device 14 and/or computing system 18 diagnoses the portion of biological tissue, based at least in part on the comparisons.

The method 1150 terminates at 1168. In some embodiments, the method 1150 may return control back to 1152, in lieu of terminating at 1168. In other embodiments, the method 1150 may operate as separate processes or threads, in parallel or concurrently with one another.

Figure 34:
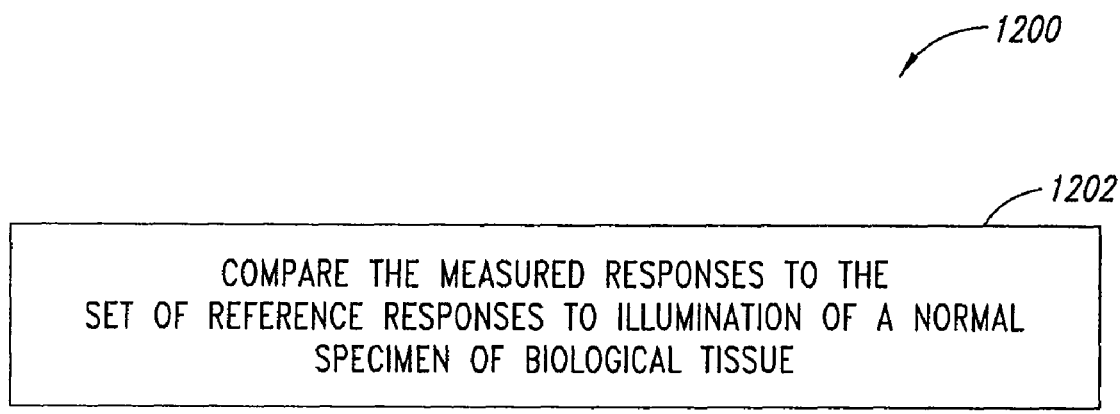
FIG. 34 is a flow diagram showing a method of operating a test device to sample biological tissue for diagnosis, according to one illustrated embodiment.

FIG. 34 shows a method 1200 of operating the test device 14 and/or a computing system 18, according to one illustrated embodiment.

At 1202, the test device 14 and/or computing system 18 compares the measured responses of the first period to the set of reference responses to illumination of a normal specimen of biological tissue.

Figure 35:
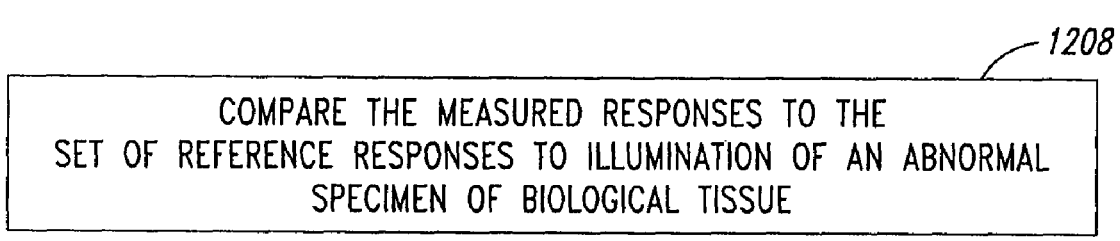
FIG. 35 is a flow diagram showing a method of operating a test device to sample biological tissue for diagnosis, according to another illustrated embodiment.

FIG. 35 shows a method 1206 of operating the test device 14 and/or computing system 18, according to another illustrated embodiment.

At 1218, the test device 14 and/or computing system 18 compares the measured responses of the first period to the set of reference responses to illumination of an abnormal specimen of biological tissue.

Figure 36:
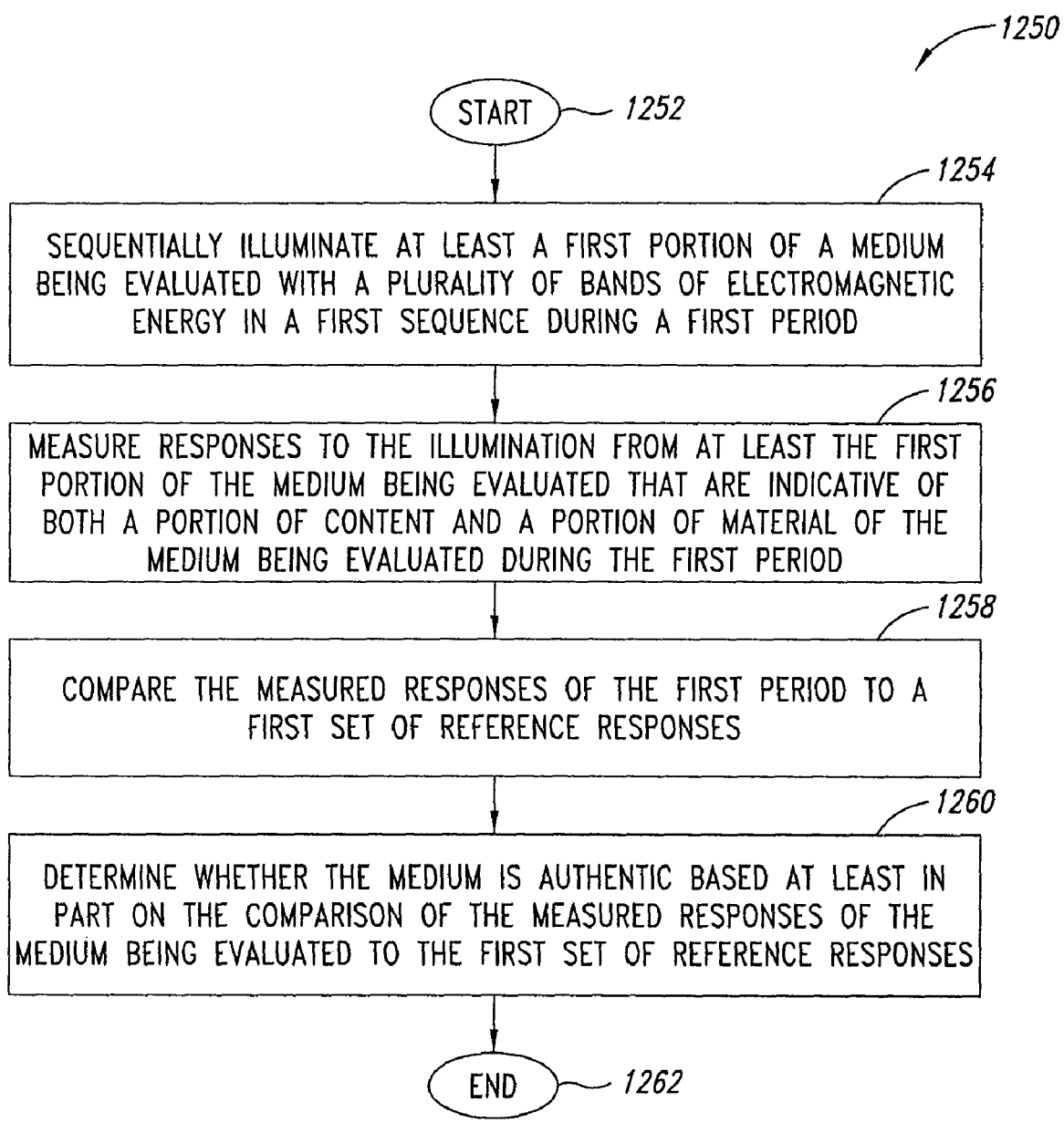
FIG. 36 is a flow diagram showing a method of operating a test device and/or computing system of an evaluation system to useful in authenticating media, according to one illustrated embodiment.

FIG. 36 shows a method 1250 of operating a test device 14 and/or a computing system 18 according to one illustrated embodiment. The method 1250 may be useful in authenticating media, for example identity documents, financial instruments, legal documents, medical documents, financial transaction cards, and/or other media.

The method 1250 starts at 1252. For example, the method 1250 may start in response to activation or powering of the test device 14 and/or computing system 18. Alternatively, the method 1250 may start in response to a user input, receipt of data or instructions, or receipt of a signal from a sensor.

At 1254, the test device 14 sequentially illuminates at least a first portion of a medium being evaluated with a plurality of bands of electromagnetic energy, in a first sequence during a first period. At 1256, the sensor 46 (FIG. 4) of the test device 14 measures responses to the illumination from at least the first portion of the medium being evaluated, during the first period. The response may be indicative of both a portion of content of the media, as well as a portion of material of the medium being evaluated.

At 1258, the test device 14 and/or computing system 18 compares the measured or test responses of the first period to a first set of reference responses. At 1260, the test device 14 and/or computing system 18 determines whether the medium is authentic based at least in part on the comparison of the measured responses to the first set of reference responses. For example, the test device 14 and/or computing system 18 may determine whether the medium being evaluated is identical to the reference medium. Such may be useful to identify works of art or original copies of documents, for example financial instruments such as bonds or share certificates. Alternatively, the test device 14 and/or computing system 18 may determine whether the medium being evaluated is similar to the reference medium. Such may be useful to identify mass produced items, for example, currency or financial transaction cards. As discussed previously, the test device 14 and/or computing system 18 may compare the measured or test response to reference responses until a match is found within some defined threshold. The threshold may be preset or may be determined during operation, and may or may not be user configurable. In other embodiments, the measured or test response is compared to all reference responses in the set of reference responses. In such embodiments, all matches within a defined threshold may be identified and reported to the end user. Alternatively, only the best or closest matching response or responses may be identified and reported to the end user. Such may include one or more indications of confidence in the match, such as a confidence level that indicates a degree of matching. The confidence level may be represented in a variety of ways, for example as a percentage of discrepancies detected or how many standard deviations the match is from being an identical match. Alternatively, the confidence level may indicate the number of times a match with a threshold was found. For example, if a match was found in response to more than one sequence, at more than one location, and/or at more than one viewpoint or angle.

The method 1250 terminates at 1262. In some embodiments, the method 1250 may return control back to 1252, in lieu of terminating at 1262. In other embodiments, the method 1250 may operate as separate processes or threads, in parallel or concurrently with one another.

Figure 37:
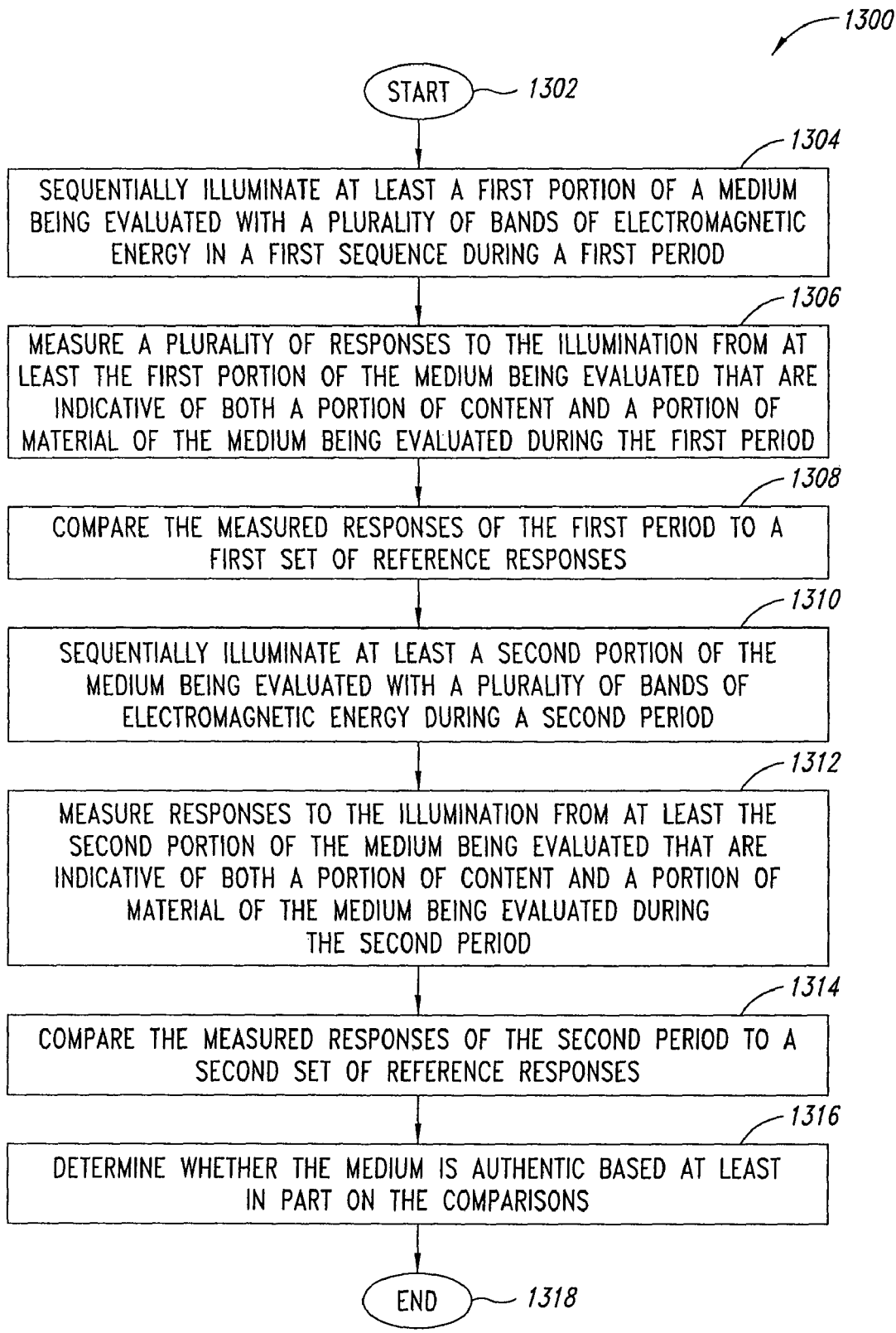
FIG. 37 is a flow diagram showing a method of operating a test device and/or computing system of an evaluation system to useful in authenticating media, according to another illustrated embodiment.

FIG. 37 shows a method 1300 of operating a test device 14 and/or a computing system 18, according to another illustrated embodiment. The method 1300 may be useful in authenticating media, such as identity documents, financial instruments, legal documents, medical documents, financial transaction cards and/or other media.

The method 1300 starts at 1302. For example, the method 1300 may start in response to activation or powering of the test device 14 and/or computing system 18. Alternatively, the method 1300 may start in response to a user input, receipt of data or instructions, or a signal from a sensor.

At 1304, the test device 14 sequentially illuminates at least the first portion of a medium being evaluated with a plurality of bands of electromagnetic energy, in a first sequence during a first period. At 1306, the sensor 46 (FIG. 4) of the test device 14 measures responses to the illumination from at least the first portion of the medium being evaluated, during the first period. The measured or test responses may be indicative of both a portion of content and a portion of material of the medium being evaluated.

At 1308, the test device 14 and/or computing system 18 compares the measured or test responses of the first period to a first set of reference responses.

At 1310, the test device 14 sequentially illuminates at least the second portion of the medium being evaluated with a plurality of bands of electromagnetic energy, during a second period. At 1312, the sensor 46 of the test device 14 measures responses to the illumination from at least the second portion of the medium being evaluated during the second period.

At 1314, the test device 14 and/or computing system 18 compare the measured or test responses of the second period to a second set of reference responses. At 1316, the test device 14 and/or computing system 18 determine whether the medium is authentic based at least in part on the comparisons.

The method 1300 terminates at 1318. In some embodiments, the method 1300 may return control back to 1302, in lieu of terminating at 1318. In other embodiments, the method 1300 may operate as separate processes or threads, in parallel or concurrently with one another.

Figure 38:
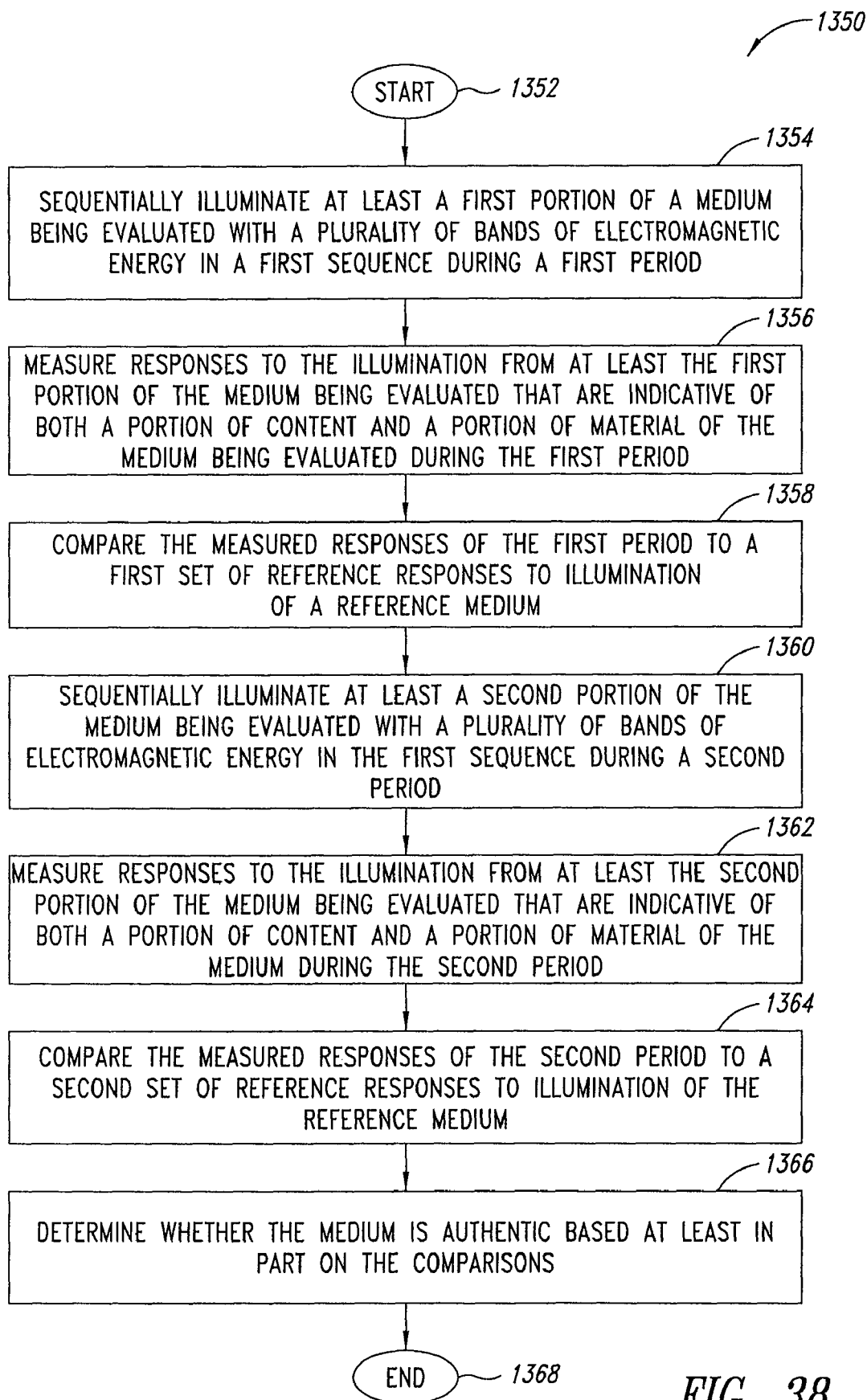
FIG. 38 is a flow diagram showing a method of operating a test device and/or computing system of an evaluation system to useful in authenticating media, according to yet another illustrated embodiment.

FIG. 38 shows a method 1350 of operating a test device 14 and/or a computing system 18, according to a yet another illustrated embodiment. The method 1350 may be useful in authenticating media such as identity documents, financial instruments, legal documents, medical documents, financial transaction cards and/or other media.

The method 1350 starts at 1352. For example, the method 1350 may start in response to activation or powering of the test device 14 and/or computing system 18. Alternatively, the method 1350 may start in response to a user input, receipt of data or instructions, or receipt of a signal from a sensor.

At 1354, the test device 14 sequentially illuminates at least the first portion of a medium being evaluated with a plurality of bands of electromagnetic energy, in a first sequence during a first period. At 1356, the sensor 46 (FIG. 4) of the test device 14 measures responses to the illumination from at least the first portion of the medium being evaluated, during the first period. The measured or test responses may be indicative of both a portion of content and a portion of material of the medium being evaluated.

At 1358, the test device 14 and/or computing system 18 compare the measured or test responses of the first period to a first set of reference responses.

At 1360, the test device 14 sequentially illuminates at least the second portion of the medium being evaluated with a plurality of bands of electromagnetic energy, in the first sequence during a second period. At 1362, the sensor 46 of the test device 14 measures responses to the illumination from at least the second portion of the medium being evaluated during the second period.

At 1364, the test device 14 and/or computing system 18 compares the measured or test responses of the second period to a second set of reference responses to illumination of the medium being evaluated. At 1366, the test device 14 and/or computing system 18 determines whether the medium is authentic based at least in part on the comparisons.

The method 1350 terminates at 1368. In some embodiments, the method 1350 may return control back to 1352, in lieu of terminating at 1368. In other embodiments, the method 1350 may operate as separate processes or threads, in parallel or concurrently with one another.

Figure 39:
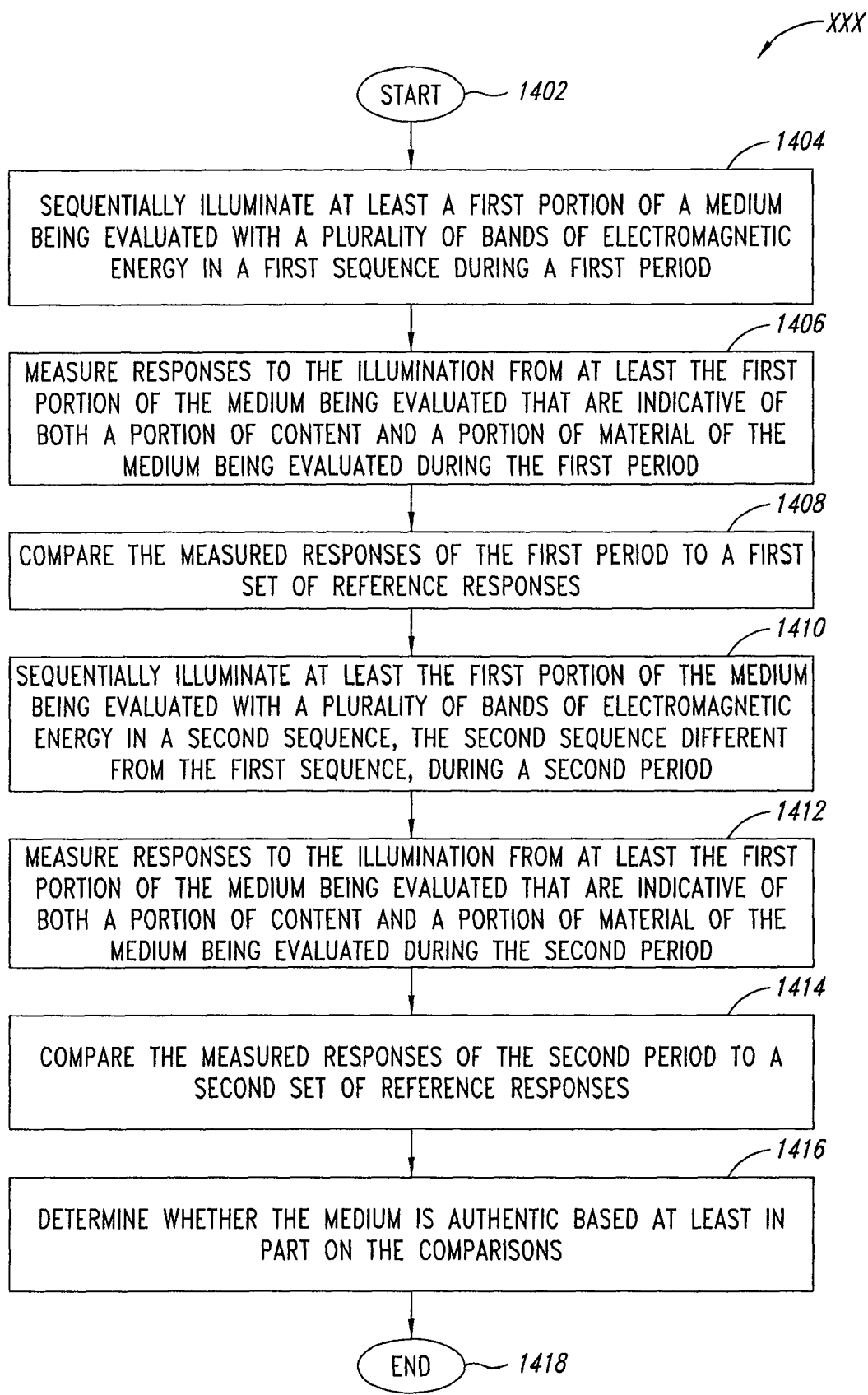
FIG. 39 is a flow diagram showing a method of operating a test device and/or computing system of an evaluation system to useful in authenticating media, according to still another illustrated embodiment.

FIG. 39 shows a method 1400 of operating a test device 14 and/or a computing system 18, according to a still another illustrated embodiment. The method 1400 may be useful in authenticating media, for example identity documents, financial instruments, legal documents, medical documents, financial transaction cards and/or other media.

The method 1400 starts at 1402. For example, the method 1400 may start in response to activation or powering of the test device 14 and/or computing system 18. Alternatively, the method 1400 may start in response to a user input, receipt of data or instructions, or receipt of a signal from a sensor.

At 1404, the test device 14 sequentially illuminates at least the first portion of a medium being evaluated with a plurality of bands of electromagnetic energy, in a first sequence during a first period. At 1406, the sensor 46 (FIG. 4) of the test device 14 measures responses to the illumination from at least the first portion of the medium being, during the first period. The measured or test responses may be indicative of both a portion of content and a portion of material of the medium being evaluated.

At 1408, the test device 14 and/or computing system 18 compares the measured or test responses of the first period to a first set of reference responses.

At 1410, the test device 14 sequentially illuminates at least the first portion of the medium being evaluated with a plurality of bands of electromagnetic energy, in a second sequence, the second sequence different from the first sequence, during a second period. At 1412, the sensor 46 of the test device 14 measures responses to the illumination from at least the first portion of the medium being evaluated. The measured or test responses may be indicative of both a portion of the content and a portion of the material of the medium being evaluated, during the second period.

At 1414, the test device 14 and/or computing system 18 compares the measured responses of the second period to a second set of reference responses. At 1416, the test device 14 and/or computing system 18 determine whether the medium is authentic, based at least in part on the comparisons. As previously noted, employing two or more sequences may enhance security and/or may enhance accuracy of the analysis.

The method 1400 terminates at 1418. In some embodiments, the method 1400 may return control back to 1402, in lieu of terminating at 1418. In other embodiments, the method 1400 may operate as separate processes or threads, in parallel or concurrently with one another.

FIG. 40 shows a method 1450 of operating the test device 14 according to one illustrated embodiment.

At 1452, the control subsystem 54 and/or microprocessor 56 (FIG. 4) of the test device 14 sequentially illuminates at least the first portion of the medium being evaluated with electromagnetic energy from bands within a visible portion, an infrared portion, or an ultraviolet portion of the electromagnetic spectrum. Other embodiments may employ bands from other portions of the electromagnetic spectrum, for example, microwave or X-ray portions.

FIG. 41 shows a method 1456 of operating a test device 14, according to another illustrated embodiment.

At 1458, the control subsystem 54 and/or microprocessor 56 (FIG. 4) of the test device 14 selectively turns respective ones of a plurality of sources 44 On and Off, in an order defined by the sequence, to illuminate the medium.

FIG. 42 shows a method 1462 of operating a test device, according to a yet another illustrated embodiment.

At 1464, control subsystem 54 and/or microprocessor 56 (FIG. 4) of the test device 14 selectively applies current to respective ones of the sources 44, in the order defined by the sequence to illuminate the medium.

FIG. 43 shows a method 1468 of operating the test device 14 according to a further illustrated embodiment.

At 1470, control subsystem 54 and/or microprocessor 56 (FIG. 4) of the test device 14 selectively applies current at a plurality of different drive levels to respective ones of the sources 44, where the order and the drive level are defined by the sequence, to illuminate the medium.

FIG. 44 shows a method 1474 of operating the test device 14 and/or computing system 18, according to one illustrated embodiment. The method 1474 may be used with the methods of FIGS. 36-39.

At 1476, the test device 14 and/or computing system 18 classifies the medium as a media type, based at least in part on the comparisons.

FIG. 45 shows a method 1480 of operating the test device 14 and/or computing system 18 according to one illustrated embodiment. The method 1480 may be used in any of the methods of FIGS. 36-39.

At 1482, the test device 14 and/or computing system 18 compares the measured or test responses to a set of reference responses to illumination of a reference specimen of a reference medium that reflects the spectral characteristics that are associated with authenticate copies of the reference medium. Such an approach may be particularly useful to authenticate mass produced media or copies of original media, for example, currency or financial transaction cards.

FIG. 46 shows a method 1486 of operating a test device 14 and/or computing system 18 according to one illustrated embodiment. The method 1486 may be useful in the methods of FIGS. 36-39.

At 1488, the test device 14 and/or computing system 18 compares the measured responses to a set of reference responses to illumination of the medium during a previous period that occurred before the first period. Thus, the medium being evaluated can be compared against itself to determine if it is the same identical or original medium. Such may be useful to identify works of art or original copies of documents, for example financial instruments such as bonds or share certificates.

FIG. 47 shows a method 1492 of operating a test device 14 according to another illustrated embodiment.

At 1494, the test device 14 sequentially illuminates at least a first portion of a financial instrument. A financial instrument may, for example, take the form of currency, checks, bonds, money orders, and/or securities.

FIG. 48 shows a method 1498 of operating a test device 14 according to another illustrated embodiment.

At 1500, the test device 14 sequentially illuminates at least the first portion of an identity document. The identity document may, for example, take the form of documents, such as passports, identity cards (e.g., national, state, provincial, military, employer, school, organization), driver's licenses, and/or birth or naturalization certificates.

FIG. 49 shows a method 1504 of operating a test device 14 according to one illustrated embodiment.

At 1506, the test device 14 sequentially illuminates at least a first portion of a medium bearing a likeness of an individual identified by an identity document. The likeness may take a variety of forms, for example a photograph or other reproduction of the individual's likeness or image. Thus, the measured or test response will reflect the individual's likeness.

FIG. 50 shows a method 1510 of operating a test device 14, according to one illustrated embodiment.

At 1512, the test device 14 sequentially illuminates at least the first portion of a legal document. The legal document may take the form of a licenses, permits, assignments, deeds, wills, declarations, oaths, agreements, pleadings, or motions.

Figure 51:
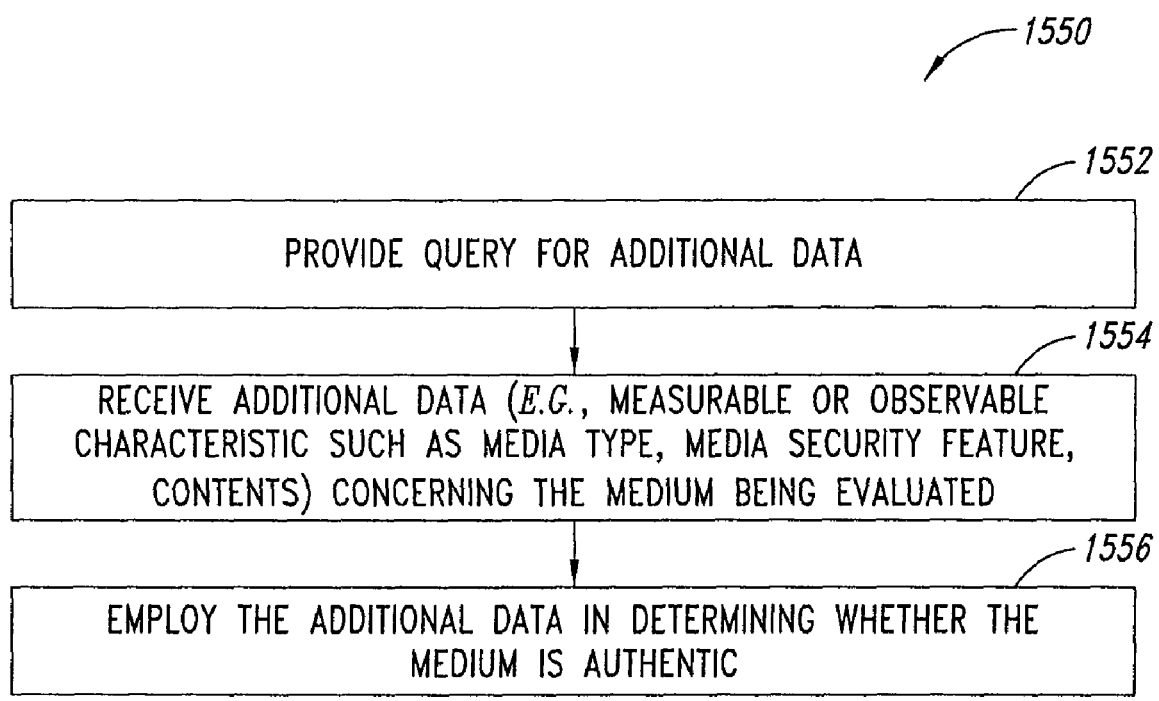
FIG. 51 is a flow diagram showing a method of operating a test device and/or computing system of an evaluation system to determine additional information, that may be useful in the previous methods, according to one illustrated embodiment.

FIG. 51 shows a method 1550 of operating a test device 14 and/or computing system 18, according to another illustrated embodiment. The method 1550 may be employed with one or more of the previously described methods.

At 1552 the test device 14 and/or computing system 18 provides a query for additional data. The query may be made to an end user, for example an end user operating the test device 14, or the computing system 18. The query may be made to a database of information.

The query may take a variety of forms. For example, the query may request information regarding an object, for example the name of the manufacturer, the model, the color, the year of production or release. The query may request information regarding a document, for example a name or title, year of publication or execution, names of parties or those executing the document, number of pages, paragraphs, words or letters, content, security feature, serial number, expiration date, type of material, etc. The query may request information regarding biological tissue, for example date of specimen, identifier for specimen or subject from which the specimen as derived, name of subject, gender, type of tissue, temperature, heart rate, oxygen level, levels of toxics, protein levels, reported conditions such as aches, nausea, dizziness, coughing, swelling, etc.

At 1554, the test device 14 and/or computing system 18 receive additional data. As noted above, the additional data may take any of a variety of forms. The additional data may be a measurable or observable characteristic. For example a measurable or observable characteristic of an object, media or biological tissue.

At 1556, the test device 14 and/or computing system 18 employs the additional data in determining whether the medium is authentic. For example, the test device 14 or computing system 18 may employ the additional data to increase a confidence level in a match, or to find a closest match. Also for example, the test device 14 or computing system 18 may alternatively, or additionally employ the additional data to or to reduce the number of reference samples to which the measured or test response will be compared. This may advantageously reduce processing time and use of computational resources.

While not generally discussed above, the computing system 18 or associated separate accounting system (not shown) may track usage by a financial entity, such as a business (e.g., corporation, partnership, sole proprietorship, limited liability company), a division of a business, a non-profit, a government (e.g., federal, state or provincial, county or parish, city or town), of division of a government (e.g., agency, department)). The financial entity is an entity financially obligated for the various transactions occurring on the evaluation system 10. The financial entity may, for example, be the owner, operator, lessee, or otherwise in control of test devices 14 and/or database 20, 34. Such is accounting methods and structures are discussed in more detail in commonly assigned U.S. provisional patent application Ser. No. 60/834,662, filed Jul. 31, 2006 using Express Mail No. EV448396842US.

Further, while not discussed above, the computing system 18 may authenticate the test device 14 and/or user of the test device 14. For example, the computing system 18 may verify a user identifier and/or device identifier. Additionally, or alternatively, the computing system 18 may verify a password and/or personal identification number (PIN). The computing system 18 may employ other approaches to authenticating the test device 14 and/or user. Additionally, or alternatively, the computing system 18 may determine whether the test device 14 and/or user of the test device 14 has sufficient permission to access the data. The computing system 18 may check one or more permission data structures to determine a level of access granted to the testing device 14 and/or user of the test device 14. Access may, for example, be limited to data related to certain objects. Alternatively, or additionally, data may be limited to authorized personnel with, for example with respect to identification of individuals and/or bodily tissue. Other restrictions may of course apply. Such security methods and structures are discussed in more detail in commonly assigned U.S. provisional patent application Ser. No. 60/834,662, filed Jul. 31, 2006 using Express Mail No. EV448396842US.

As noted above, in some embodiments, the sequence may also define a variety of temperatures for the sources 44, where such temperatures can be controlled, for example by one or more heaters such as resistors (not shown) and/or one or more thermoelectric coolers (not shown). Such is discussed in more detail in commonly assigned U.S. provisional patent application Ser. No. 60/834,662, filed Jul. 31, 2006 using Express Mail No. EV448396842US.

FIG. 52 shows a test device 14 according to one illustrated embodiment, positioned next to a dime to illustrate a possible size of the test device, and with all sources simultaneously illuminated to better illustrate the various wavelengths of the sources. FIG. 53 shows the test device 14 of FIG. 52 with one source illuminated during operation. FIG. 54 shows the test device 14 of FIG. 52 with another source illuminated during operation.

Rather than illuminating a specimen with broadband white light and using a prism to separate wavelengths onto a large array of detectors, the test device illuminates the specimen with multiple light sources of different narrowband spectra and measure the reflected light with a single detector—allowing us to produce devices that are cheaper, smaller, and lighter weight.

The simplest embodiment of the test device 14 includes a single photodiode light sensor (arrow in FIG. 52) and multiple surface-mount light emitting diodes (LEDs), that project different spectra of light (with peak wavelengths at different shades of infrared, red, orange, yellow, green, blue, violet, ultraviolet). In the simplest driving scheme, the LEDs are turned on, one at a time (e.g., FIGS. 53 and 54), to project light onto a specimen. The specimen reflects a portion of the light back to the photodiode of the test device, which converts the light energy to an output voltage level—essentially taking a snapshot of the specimen for each LED. The photodiode voltage levels form a spectral signature for the specimen, which is stored in a small file.

FIG. 55 shows a monitor and displaying a screen of a user interface, according to an illustrated embodiment. FIG. 55 shows the basic form of the test device 14 collecting a spectral signature of a paint sample and sending data to a host computer. FIG. 55 shows one exemplary spectral signature plotted in white on a black background.

The software interface on the computer can be navigated with a mouse or with verbal commands captured with speech recognition algorithms—enabling hands-free control of the device for a user in the field. The test device acquires multiple spectral signatures per second, and plots them in real-time on the screen for the user. A set of proprietary algorithms compares the spectral signature to a database of known signatures, and quantifies the closeness of the match (reported as root mean square). E.g., in FIG. 55, the specimen is identified as paint sample W-F-720 and the signatures are a 99.682% match. New items can be added to the database on-the-fly. As noted above, the database can be stored locally in a mobile device, on a nearby computer, or on a remote server. Proprietary encryption algorithms are used to transmit spectral signatures to a remote server.

Figure 56:
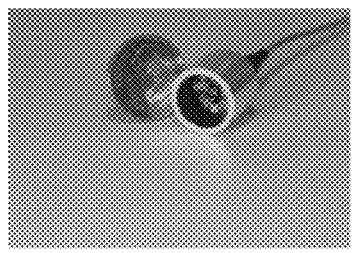
FIG. 56 shows a test device according to an illustrated embodiment, positioned next to a dime to illustrate a possible size.

FIG. 56 shows a test device 14 according to an illustrated embodiment, positioned next to a dime to illustrate a possible size.

Figure 57:
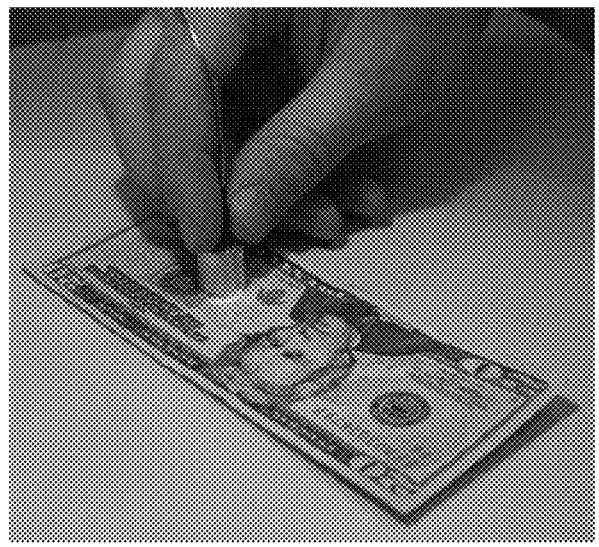
FIG. 57 shows a test device being used to test a piece of currency, according to an illustrated embodiment.

FIG. 57 shows a test device 14 being used to test a piece of currency, according to an illustrated embodiment. Some aspects of testing are discussed in U.S. provisional patent application Ser. No. 60/820,938, filed Jul. 31, 2006.

EXAMPLES

Example 1

ID/Passport Verification

A pattern database of passport photos of every U.S. citizen may be searchable within seconds to confirm their identity. For security purposes, the search patterns for the entire database may be changed, for example, in less than thirty minutes or even on demand. This may reduce or eliminate identification document fraud, and also reduces or eliminates the cracking the security code.

The object evaluation system 10 can verify a passport or other identification documentation as follows:

When a passport application is submitted, a photo is included which will be affixed to a validly issued passport. The photo identifies the person submitting the application. Once the issuing authority determines that a passport is to be issued, the issuing authority will generate and store at least one known reference pattern associated with the photo (the reference object 50 in this example), as well as other identity information relating to the identity of the person to whom the passport is issued, such as the person's name, physical characteristics, address, social security number, etc. (other issuance information can also be included if necessary, such as for example the date of issuance). A data file containing the reference pattern 202 (FIG. 6) and associated identity information is stored in the data structure 200 with a plurality of other reference patterns 202 generated by the issuing authority for other validly issued passports. The issued passport containing the photo is then sent to the person who submitted the application.

At a security checkpoint, for example at an airport terminal, a passport is provided by a traveler for identification purposes. The passport (sampled object 50) is provided to the test device 14 of the system 10. A region is selected within the passport photo (the sampled object 50 in this example) for which a spectrum measuring device of the test device 14 measures the spectral contents, i.e., color information, and outputs information indicative of the same to the computing system 18 or microprocessor 56 operating spatial analysis software.

The spectral content information outputted by the spectrum measuring device is provided as input to the spatial analysis software program, which generates a measured pattern for the sampled passport photo. In some embodiments, the measured pattern may be in the XYZ color space, and/or the measured pattern can be observed from virtually any angle. The measure pattern (or a view key generated therefrom) is compared to the plurality of reference patterns stored in the passport issuing authority's database (or view keys generated therefrom) until a matching reference pattern is found. If a matching reference pattern is not found, then the passport is deemed to be a fraud by the spatial analysis software. If a match is located, identity information associated with the matching reference pattern is analyzed to determine if the identity information for the matching reference pattern substantially corresponds to the identity information associated with the sampled passport photo.

At least a portion of the identity information associated with the sampled passport photo is generally located within the passport, and can be provided to the spatial analysis software for analysis (e.g., by the user entering or scanning the identity information present in the passport), and/or the identity information within the passport can be provided to the human user to perform the comparison. If the identity information associated with the sampled passport photo matches the identity information associated with the matching reference pattern, the passport photo will be deemed an authentic and validly issued passport (i.e., not a forgery) by the spatial analysis software, and the traveler will be permitted to proceed past the security checkpoint.

Further, it should be understood that the materials used to construct the passport (or other identification documentation materials) can be validated against known spectral or color data. The paper and inks can be checked to determine if the passport itself is a forgery, not just the photo or information printed on the document.

Example 2

Document Authentication

The object evaluation system 10 can be used to detect forgeries of a document of value, such as money or bank notes, or other sensitive documents operates as follows:

When a document is validly produced, the producing entity generates and stores at least one reference pattern 202 for the original document (the reference object 50 in this example), as well as other identity information relating to the identity or characteristics of the document, such as the date it was produced, a general title for the document, key terms or monetary value, etc. A data structure 200 containing the reference pattern 202 and identity information associated with the reference pattern 202 is then delivered or made available to an eligible recipient of the original document.

When the recipient is later presented with a document (sampled object 50), the recipient can use the object evaluation system 10 to check the authenticity of the presented document, i.e., to determine whether the presented document is the original document or of the same quality or origin as the original document. It should be understood that if the document is one that is duplicated, such as a dollar bill for example, then only reference patterns for one representative document needs to be used for authentication.

The presented document is provided to a spectrum measuring device of the test device 14. A region is selected within the presented document (the sampled object 50 in this example) for which the spectrum measuring device measures the spectral content and outputs information indicative of the same to the computing system 18 or microprocessor 56 operating spatial analysis software.

The spectral content information outputted by the spectrum measuring device is provided as input to the spatial analysis software, which generates a measured pattern for the sampled document. The measured pattern (or a view key generated therefrom) is compared to the specific reference pattern 202 previously generated for the original document (or a view key generated therefrom). If the measured pattern does not match the reference pattern 202, then the presented document is deemed a forgery by the spectral analysis software. If the measured pattern matches the reference pattern, then the presented document is deemed authentic by the spectral analysis software and the recipient can accept the presented document.

For further authentication, the identity information associated with the original document can also be compared to identity information associated with the presented document to determine if they substantially correspond. At least a portion of the identity information associated with the presented document is generally located within the document, and can be provided to the spatial analysis software for analysis (e.g., by the user entering or scanning the identity information present in the document), and/or the identity information within the presented document can be provided to the human user to perform the comparison.

Example 3

Product Monitoring

The object evaluation system 10 can be used for brand protection to verify the authenticity of a product based on the make of its material (e.g., fabric colors) operates as follows:

When a manufacturer mass produces a product, at least one reference pattern 202 for a representative of the product (the reference object 50 in this example) is generated and stored in the reference pattern data structure 200, as well as identity information associated with the original product, such as the name or style of the product, a serial number, a color description, a size, the manufacturer's name and address, etc.

To determine if the product (sampled object 50) is of the same quality or of the same origin as the original representative product, a distributor or individual consumer can provide the product to be sampled to the object evaluation system 10. A region is selected within the sampled product (the sampled object 50 in this example) for which a spectrum measuring device of the test device 14 measures the spectral content and outputs information indicative of the same to the computing system 18 or microprocessor 56 operating spatial analysis software.

The spectral content information outputted by the spectrum measuring device is provided as input to the computing system 18 or microprocessor 56 executing the spatial analysis software, which generates a measured pattern for the sampled product 50. The measured pattern (or a view key generated therefrom) is compared to the reference patterns 202 in the data structure 200 (or view keys generated therefrom) until a matching reference pattern 202 is found. If a matching reference pattern is not found, then the sampled product 50 is deemed to be a fraud. If a match is located, then the identity information associated with the matching reference pattern is analyzed to determine if the identity information for the matching reference pattern substantially corresponds to the identity information associated with the sampled product. At least a portion of the identity information associated with the sampled product 50 is generally located on a label or tag on the product, or observable by a human user, and can be provided to the computing system 18 or microprocessor 56 executing the spatial analysis software for analysis (e.g., by the user entering or scanning the identity information present in the label or tag or obtained from observation), and/or the identity information associated with the matching reference pattern can be provided to the human user to perform the comparison. If the identity information associated with the sampled product 50 matches the identity information associated with the matching reference pattern, the sampled product 50 will be deemed authentic and the purchase and/or distribution of the sampled product 50 can proceed. If the measured pattern does not match the reference pattern 202, then the sampled product 50 is deemed a knock-off or tampered product.

Thus, the object evaluation system 10 can be utilized for brand protection to verify the authenticity of products based on the make of their fabric colors with the pattern of the original product in database, the system 10 can compare a knock off versus the real product in a matter of minutes by scanning any area of the product for which a database pattern exists. In a preferred embodiment, once the fabric has been scanned, a view key is selected to obtain a pattern file. This pattern file will be compared against a pattern from an authentic fabric sample on our database from the same view key point.

Art forgery is anther area of product verification that the object evaluation system 10 can be used. That is, spectral data can be taken from one or more regions of a valuable piece of art and this spectral data could be used to authenticate copies or unknown works.

Quality Control of Manufacturing Process

The object evaluation system 10 can be also be used for quality control of manufacturing processes to maintain quality control on practically any manufactured good or the packaging for the good. In this regard, the system 10 would operate as follows:

When a manufacturer mass produces a product, a variety of reference patterns 202 can be taken from the product (reference object 50) at different locations or areas within the manufacturing process. To determine if the manufacturing process is operating properly, readings can be taken from the products (sampled objects 50) during actual manufacturing and compared to the reference patterns 202 to determine whether the manufacturing process is operating to predetermined quality control standards. Depending upon the results of the comparison, the manufacturing process can be shut down or modified (if the comparison shows unacceptable quality control) or subsequent parts of the manufacturing process can be actuated. For example, if the product (sampled object 50) was a loaf of bread being baked within an oven, then readings could be taken of the loaf of bread and compared with the reference patterns 202 until the comparisons indicate the loaf of bread is ready to be removed from the oven.

Quality Control/Nondestructive Testing of Manufactured Products

The object evaluation system 10 can also be used for quality control or nondestructive testing or evaluation of manufactured products. Such may be employed to test or evaluate products over the lifetime of such products, for example to detect cracks, stress or strain formation and/or deterioration in products that occurs during use. Such may be useful in the periodic or ad hoc inspection or maintenance of products. Such may be particularly advantageous for inspecting products which are subject to cyclic loading, for example aircraft fuselages, wings and other parts, submarines hulls, or turbines, etc. Such may be particularly advantageous for inspecting products which are subject to environmental factors, for example, ultraviolet radiation, wind, temperature fluctuations, freezing, high temperatures, moisture, lightning strikes, etc.

When a manufacturer mass produces a product, a variety of reference patterns 202 can be taken from the product (reference object 50) at different locations on the product. The references patterns may cover the entire surface of the manufactured product or may cover portions of the product known or suspected of being susceptible to fatigue, cracking, stress and/or strain. The reference patterns 202 may be taken when the product is new, used, or subject to some set of conditions.

From time to time during the life of the product or assembly including the product, samples are taken of the product or portion thereof. For example, the product or portion thereof may be sampled using the test device 14 in the manner discussed above, periodically or in an ad hoc timing. The samples are compared to the reference patterns 202. Differences between the samples and the reference patterns 202 may indicate development of fatigue, cracking, stress and/or strain or other deterioration in the manufactured product. In some embodiments, the reference patterns 202 may represent a product that is new or relatively new and that has not been subject to cyclic loading or other environmental factors. In some embodiments, the reference patterns 202 may represent a product that has been subject to cyclic loading or other environmental factors, but still represents a product that is considered safe and within a defined set of safety tolerances.

Alternatively, or additionally, a match between the samples and the reference patterns 202 may indicate development of fatigue, cracking, stress and/or strain in the manufactured product or other deterioration. In such embodiments, the reference patterns may represent a product that has been subject to cyclic loading or other environmental factors to such a degree that the product is considered unsafe and/or outside of a defined set of safety tolerances.

Depending upon the results of the comparison between the samples and the reference patterns 202, the product or assembly may be taken out of service and destroyed, recycled, rebuilt or repaired.

Some embodiments may employ photonic band gaps created by the particular characteristics of the manufactured product to allow detection of the appearance of fatigue, cracks, strain, stress or other deterioration. For example, a crack that is not visible to the unaided eye may create a photonic band gap that is clearly discernable in the comparison to the reference patterns. Also for example, fatigue, strain, stress or other deterioration that is not otherwise visible to the unaided eye may create a photonic band gap that is clearly discernable in the comparison to the reference patterns. Such may produce a sample that represents the product or portion thereof in three-dimensions, for example, where a crack extends into a surface of the manufactured product.

Some embodiments may employ relatively long wavelengths (e.g., infrared) to penetrate below the surface of the manufactured product. Such may allow detection of below surface optical characteristics indicative of fatigue, cracks, strain, stress or other deterioration. Such may produce a sample that represents the product in three-dimensions.

Figure 58:
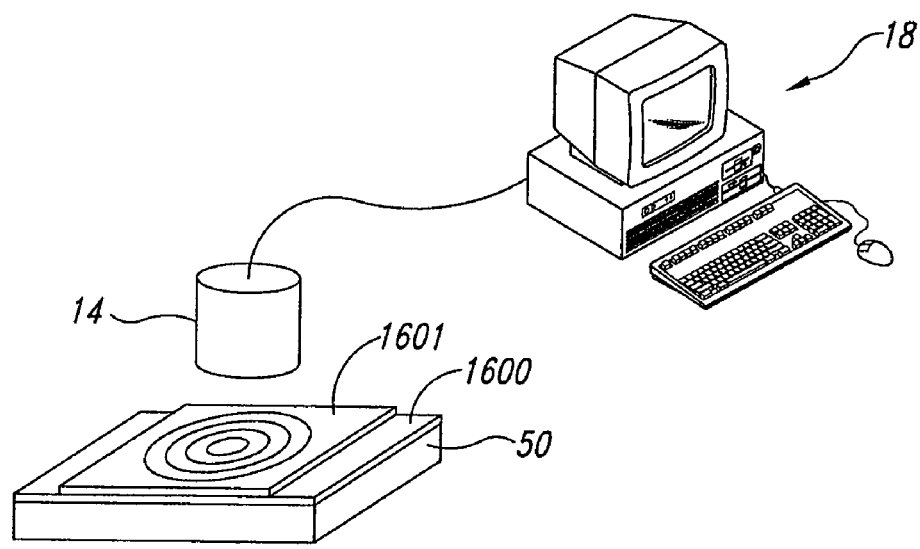
FIG. 58 is a schematic diagram showing a test device being used with an optical filter to perform inspection for fatigue, cracks, stress, strain or other deterioration on a manufactured product such as a portion of an aircraft, according to an illustrated embodiment.

Some embodiments may employ coatings and/or optical filters such as one or more diffraction gratings to enhance the appearance of optical characteristics indicative of fatigue, cracks, strain, stress or other deterioration. For example, FIG. 58 shows a test device 14 being used with a photostress coating 1600 applied to the product 50 and a polarizing film 1601 overlying the photostress coating 1600 to perform inspection for fatigue, cracks, stress, strain or other deterioration on a manufactured product 50 such as a portion of an aircraft, according to an illustrated embodiment. Such materials are commercially available, for example from Vishay Intertechnology, Inc. of Malvern, Pa.

Figure 59:
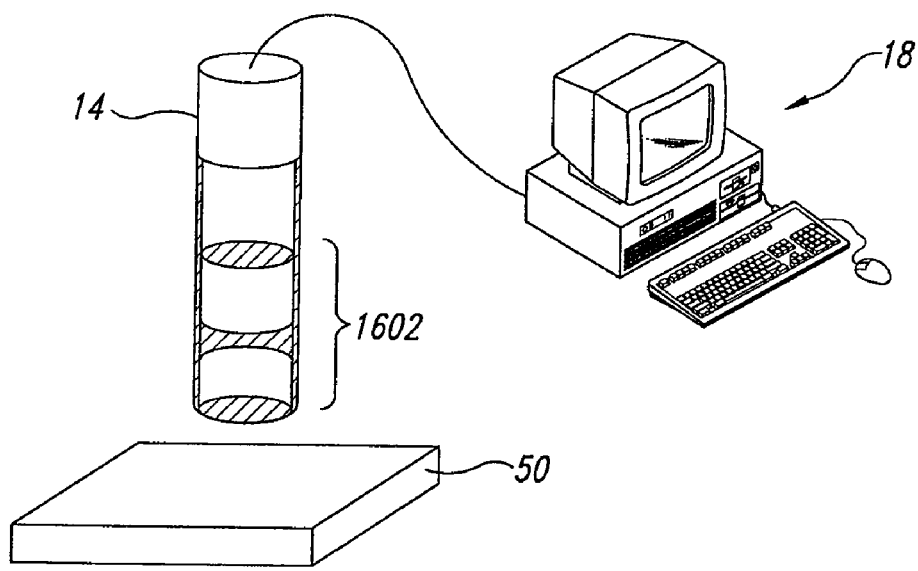
FIG. 59 is a schematic diagram showing a test device being used with a lens system which is partially shown in cross-section, to perform routine inspection for fatigue, cracks, or other deterioration in a product during the life of the product.

Some embodiments may employ magnification to enhance the appearance of optical characteristics indicative of fatigue, cracks, strain, stress or other deterioration. For example, FIG. 59 shows a test device 14 being used with a lens system 1602 (shown in cross-section), to perform routine inspection for fatigue, cracks, or other deterioration in a product during the life of the product. For instance, optical electromagnetic radiation may be provided via one or more lens to the test device 14 from the product being sampled. Such may allow focus on a specific portion of the product.

Some embodiments may employ one or more substances applied to the manufactured product to improve visualization of fatigue, cracks stress, strain or other deterioration. For example, a fine dust or powder may be blown or otherwise applied to the product. Alternatively, a liquid or gel may be flowed or otherwise applied to the product. Such visualization materials may have a size sufficiently small to inhabit a crack or micro-crack. The crack might not otherwise be visible to the unaided eye, or may not be visible even with the visualization material. Such visualization material may have a charge (e.g., static charge) that causes the visualization material to be retained by the crack. Such visualization material may be retained in a crack even after other visualization material is removed from the product, for example by being blown or washed. The visualization material may enhance the ability to discern a crack using the test device 14, since such visualization material would produce a different spectral signature than the manufactured product. In some embodiments, the visualization material may take the form of nanoparticles (e.g., nano-sized particles of gold, silver, carbon).

In some embodiments, the system 10 may be employed to monitor the quality, health or other characteristics of goods, products, for example fluids or products which flow (e.g., grain, powder, gels, etc.). The goods, products, or fluids may, for example, take the form of manufactured goods, products or fluids. For instance, the quality or health of lubricants or fuels may be monitored. Such lubricants or fuels may or may not be refined. Also for instance, the quality or health of fluids such as coolants may be monitored. Such coolants may or may not be refined or otherwise manufactured.

For instance, a spectral response of a lubricant, fuel or coolant may be compared with spectral responses of reference samples of lubricants, fuels or coolants with known characteristics that may be indicative of the quality or health of the lubricant, fuel or coolant. Such characteristics, may for example include, or be indicative of, varying degrees or concentrations of particulates or contaminants, and/or physical or chemical changes. Such may, for instance, be indicative of viscosity or ability to provide suitable levels of lubrication, energy and/or heat transport. Such may allow the monitoring of goods, products or fluids, useful in a variety of circumstances, for instance in machinery which employs lubricants, fuel and/or coolant. In some embodiments, the monitoring may be performed on a periodic or non-periodic basis during routine maintenance or service checks. Such monitoring may include the withdrawal of a sample or specimen of the good, product or fluid, for instance withdrawal of a sample of a lubricant, fuel or coolant. In some embodiments, the monitoring may be performed without the withdrawal of a sample or specimen.

Figure 60:
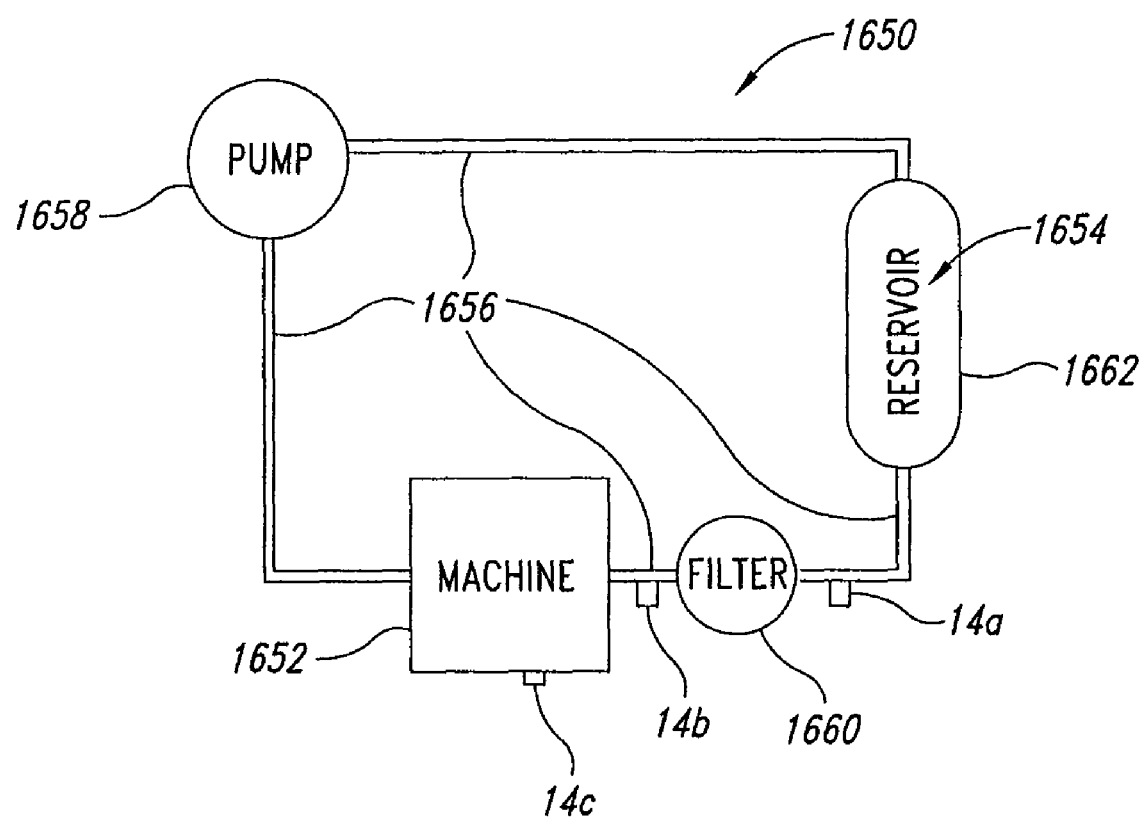
FIG. 60 is a schematic diagram showing a piece of machinery, a supply system to supply material to the piece of machinery and test devices positioned to sample the material supplied to the piece of machinery.

FIG. 60 shows a supply system 1650 that allows monitoring to be performed without the withdrawal of a sample or specimen, according to one illustrated embodiment.

The supply system 1650 may supply one or more components to a piece of machinery 1652. For example, the supply system 1650 may supply one or more fluids 1654 to the piece of machinery 1652. Such fluids 1654 may, for example, take the form of lubricants, fuels, and/or coolants. The supply system 1650 includes conduit 1656 to provide a fluid communicating path to the piece of machinery 1652. The supply system 1650 may optionally include one or more pumps 1658 to move the fluid 1654 through the conduit 1656. The pump 1658 may take any form suitable for the particular fluid 1654 and application, including but not limited compressors, fans, rotary pumps, impeller, etc. The supply system 1650 may optionally include one or more filters 1660 coupled to the conduit 1656 and configured to remove containments from the fluid 1654. The filter 1660 may, or may not, include one or more catalysts. Although FIG. 60 illustrates the filter 1660 positioned immediately following the machinery 1652, other embodiments may position the filter 1660 in other locations in the supply system 1650 and/or may include additional filters at other locations. The supply system 1650 may optionally include a reservoir 1662 to store the fluid 1654.

One or more test devices 14 may be positioned at various locations in the supply system 1650 to monitor the quality or health of the fluid 1654. For example, one test device 14a may be positioned immediately following the filter 1660 to ensure that fluid 1654 coming from the filter 1660 has one or more desired characteristics. Characteristics include, but are not limited to, level or percentage of particulates or impurities, viscosity, heat transfer ability or thermal mass, chemical or physical makeup. The test device 14a may also allow a determination to be made as to whether the filter 1660 is correctly functioning. For example, detecting particulates above a certain range or threshold may indicate that the filter 1660 is clogged or ineffective and needs to be changed or replaced.

Also for example, a test device 14b may be located to immediately following the machinery 1652, for example before the filter 1660. The test device 14b allows a determination to be made as to the quality or health of the machinery 1652. For example, detecting particulates above a certain range or threshold may indicate that the machinery 1652 is not receiving sufficient lubrication or some parts are out alignment and grinding together. Also for example, detecting a change in the physical or chemical attributes may indicative excessive heat which may be indicative of a problem with the machinery 1652, conduit 1656, and/or coolant.

Further, one or more test devices 14c may be positioned in or on the machinery 1652. The test device 14c may monitor material within or on the machinery 1652, for example fluids 1654, for instance lubricants, fuels and/or coolants. Additionally, or alternatively, the test devices 14c may monitor or other aspects of the operation of the machinery 1652 or supply system 1650. Additionally, or alternatively, a test device 14c may be positioned in, on or proximate an active component of the supply system 1650, for example the pump 1658 or a valve or actuator.

The test devices 14a, 14b may be positioned in other locations, may be omitted, and/or additional test devices 14 may be employed. For example, the test device may be located with the machinery 1652 where such test device is able to withstand the rigors (e.g., temperature, vibration, stress, force, pressure) of operation. Portions of the conduit 1656 may be designed, formed or positioned to facilitate the operation of the test devices 14. For example, a portion or all of the conduit 1656 may be transparent or translucent to a particular range or ranges of electromagnetic radiation employed by the test devices 14. Also for example, a portion or all of the conduit may be designed, formed or positioned to adjust a speed of the fluid 1654, for instance, allowing a pooling of the fluid. As a further example, a portion or all of the conduit may be designed, formed or positioned to adjust or provide a desired spatial dimension (e.g., thickness, width) of the fluid suitable for measuring responses.

Such testing may be performed continuously, periodically or intermittently. Such testing may advantageously allow real time results from operating machinery. Such may advantageously eliminate the need for additional equipment (e.g., sample or specimen holders, etc.) which may require special handling or disposal procedures. Monitoring the quality or health of goods, products and/or fluids may be employed in a variety of applications. For example, the monitoring of the quality or health of lubricants, fuels and/or coolants may be employed in applications including but not limited to vehicles such as ships, aircraft, cars, trucks, buses, trolleys, trains, without regard to fuel source, and to other machinery including but not limited to motors, engines, turbines, generators, presses, drills, bores, or any other device with moving parts, whether or not such machinery is used in a vehicle.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems for recognizing, identifying, verifying, authenticating, classifying, and/or diagnosing or otherwise evaluating objects such as, but not limited to, manufactured goods and articles;

media, for example identity documents, financial instruments, legal documents, other documents and other media; and biological tissue, not necessarily the exemplary networked evaluation system generally described above.

For example, images of a test object may be useful for more than simple spectral analysis. For instance, the image information may be employed by other image/pattern recognition algorithms to, for example, identify objects independent of, or in conjunction with the test object's spectral composition. Additionally, the image recognition algorithms can usefully interact with the spectral analysis algorithms. For instance, image analysis may be employed to locate a target area within an image of the test object, and carry-out a detailed spectral analysis of the target art. For example, the test device 14 may capture an image of an identification document, such as a passport, at any orientation, find a target area on the identification document (e.g., 3 mm to the left of the lower right hand corner of a photo carried by the passport), and perform a spectral analysis of that target area, which is known to contain particularly useful spectral information. The target area may advantageously be kept confidential to maintain security of the system. In addition to this interaction between spectral analysis and spatial analysis, there can be more complex analyses performed, for example where a signature form a test object comprises a multi-dimensional dataset of spectral information at multiple points in space on the test object.

A possible advantage may include low manufacturing cost testing. LEDs are mass-produced commodity items and thus are very inexpensive (e.g., fractions of a cent when purchased in bulk). The other components in our system, such as photodiodes are also quite inexpensive, enabling us to produce the Cyclops at a fraction of the cost of competing technologies. The material costs for a simple test device unit can be well under five dollars. Conversely, customers are used to purchasing photospectrometers for hundreds to tens of thousands of dollars.

A possible advantage may include the small size and light weight. One embodiment is the diameter of a dime.

A possible advantage may include high speed. At least one embodiment scans approximately 10 objects per second, and the prototype being developed now is capable of scanning thousands of objects per second.

As noted above, there are numerous applications. For example, authentication. Since the test device reads the spectral signatures that are naturally present in objects, it is not necessary to implant manmade markers (such as RFIDs, barcodes, chemical tracers, or encrypted graphics). Even if such markers are fairly inexpensive per unit, such technology scales poorly—as the amount of objects increases, the cost to implement scales proportionately. A single test device can be used to identify groups of objects of any size, and new objects can be added to the database without any additional cost. Such may be applied to authentication of: currency, passports, and identification cards, branded assets, Pharmaceuticals, fine art, insured goods, and/or shipping crate seals, for example at ports of entry. Also for example, quality control, such as in manufacturing and pharmaceuticals.

The foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to: U.S. Provisional Patent Application Serial Nos. 60/623,881, filed Nov. 1, 2004; 60/732,163, filed Oct. 31, 2005; 60/820,938, filed Jul. 31, 2006; 60/834,662, filed Jul. 31, 2006; 60/834,589, filed Jul. 31, 2006; 60/871,639, filed Dec. 22, 2006; 60/883,312, filed Jan. 3, 2007; 60/890,446, filed Feb. 16, 2007; and U.S. Nonprovisional patent application Ser. No. 11/264,626, filed Nov. 1, 2005, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A method of verification, the method comprising:
during a first period, sequentially illuminating at least a first portion of a medium being evaluated with a plurality of bands of electromagnetic energy in a first sequence;
during the first period, measuring a plurality of responses to the illumination from at least the first portion of the medium being evaluated that is indicative of both a portion of content and a portion of material of the medium being evaluated;
comparing the measured responses of the first period to a first set of reference responses;
after the comparing the measured responses of the first period to the first set of reference responses, varying a sequence of illumination used to determine whether the medium is authentic, the varying the sequence of illumination used to determine whether the medium is authentic including:

during a second period, sequentially illuminating at least the first portion of the medium being evaluated with a plurality of bands of electromagnetic energy in a second sequence, the second sequence different from the first sequence;

during the second period, measuring a plurality of responses to the illumination from at least the first portion of the medium being evaluated; and comparing the measured responses of the second period to a second set of reference responses; and making a determination regarding authenticity of the medium being evaluated based at least in part on the comparison of the measured responses of the first period to the first set of reference responses and based at least in part on the comparison of the measured responses of the second period to the second set of reference responses.

2. The method of claim 1, further comprising:

during a different period from the first period, sequentially illuminating at least a second portion of the medium being evaluated with a plurality of bands of electromagnetic energy;

during the different period, measuring a plurality of responses to the illumination from at least the second portion of the medium being evaluated;

comparing the measured responses of the different period to a third set of reference responses; and determining whether the medium is authentic based at least in part on the comparison of the measured responses of the different period to the third set of reference responses.

3. The method of claim 1, further comprising:

during a different period from the first period, sequentially illuminating at least a second portion of the medium being evaluated with a plurality of bands of electromagnetic energy in the first sequence;

during the different period, measuring a plurality of responses to the illumination from at least the second portion of the medium being evaluated;

comparing the measured responses of the different period to a third set of reference responses to illumination of a reference specimen of a reference medium; and identifying the second portion of the medium being evaluated based at least in part on the comparison of the measured responses of the different period to the third set of reference responses.

4. The method of claim 1 wherein sequentially illuminating at least a first portion of a medium being evaluated with a plurality of bands of electromagnetic energy in a first sequence includes sequentially illuminating at least the first portion of the medium being evaluated with electromagnetic energy from bands within a visible portion, an infrared portion or an ultraviolet portion of the electromagnetic spectrum.

5. The method of claim 1 wherein sequentially illuminating at least a first portion of a medium being evaluated with a plurality of bands of electromagnetic energy in a first sequence includes selectively turning respective ones of a plurality of sources ON and OFF in an order defined by the first sequence.

6. The method of claim 5 wherein selectively turning respective ones of the sources ON and OFF in an order defined by the first sequence includes selectively applying current to respective ones of the sources in the order defined by the first sequence.

7. The method of claim 5 wherein selectively turning respective ones of the sources ON and OFF in an order defined by the first sequence includes selectively applying current at a plurality of different levels to respective ones of the sources, where the order and the level is defined by the first sequence.

8. The method of claim 7 wherein selectively applying current at a plurality of different levels to respective ones of the sources, where the order and the level is defined by the first sequence includes selectively applying current at the plurality of different levels to respective ones of a plurality of light emitting diodes, at least some of the light emitting diodes having an emission spectra at a first current level that differs from an emission spectra of other of the light emitting diodes at the first current level.

9. The method of claim 1, further comprising:

classifying the medium as a media type based at least in part on the comparison to the first set of reference responses.

10. The method of claim 1 wherein comparing the measured responses of the first period to a first set of reference responses includes comparing the measured responses of the first period to a set of reference responses to illumination of a reference specimen of a reference medium.

11. The method of claim 1 wherein comparing the measured responses of the first period to a first set of reference responses includes comparing the measured responses of the first period to a set of reference responses to illumination of the medium during a previous period that occurred before the first period.

12. The method of claim 1 wherein sequentially illuminating at least a first portion of a medium being evaluated with a plurality of bands of electromagnetic energy in a first sequence includes sequentially illuminating at least a first portion of a financial instrument.

13. The method of claim 1 wherein sequentially illuminating at least a first portion of a financial instrument includes sequentially illuminating at least a first portion of at least one of a piece of currency, a check, a bond, money order, a security, a credit card, a debit card or a gift card.

14. The method of claim 1 wherein sequentially illuminating at least a first portion of a medium being evaluated with a plurality of bands of electromagnetic energy in a first sequence includes sequentially illuminating at least a first portion of an identity document.

15. The method of claim 14 wherein sequentially illuminating at least a first portion of an identity document includes sequentially illuminating at least a first portion of at least one of a passport, an identity card, a driver's license, a birth certificate or a permit.

16. The method of claim 14 wherein sequentially illuminating at least a first portion of an identity document includes sequentially illuminating at least a first portion bearing a likeness of an individual identified by the identity document.

17. The method of claim 1 wherein sequentially illuminating at least a first portion of a medium being evaluated with a plurality of bands of electromagnetic energy in a first sequence includes sequentially illuminating at least a first portion of a legal document.

18. The method of claim 17 wherein sequentially illuminating at least a first portion of a legal document includes sequentially illuminating at least a first portion of a license, an assignment, a deed, a will, a declaration, an oath, an agreement, a pleading, or a motion.

19. The method of claim 1, further comprising:

receiving additional data concerning the medium being evaluated, and wherein the making the determination regarding authenticity of the medium being evaluated based at least in part on the comparison of the measured responses of the medium being evaluated to the first set of reference responses is further based at least in part on the additional data.

20. The method of claim 19 wherein receiving additional data concerning the medium being evaluated includes receiving data indicative of at least one of a measurable or observable characteristic of the medium being evaluated.

21. The method of claim 20 wherein receiving data indicative of at least one of a measurable or observable characteristic of the medium being evaluated includes receiving data indicative of at least one of a media type or a media security feature.

22. The method of claim 20, further comprising:
providing a query for the additional data.

* * * * *